US007119165B2

(12) United States Patent
Strittmatter

(10) Patent No.: US 7,119,165 B2
(45) Date of Patent: Oct. 10, 2006

(54) NOGO RECEPTOR-MEDIATED BLOCKADE OF AXONAL GROWTH

(75) Inventor: Stephen M. Strittmatter, Guilford, CT (US)

(73) Assignee: Yale University, New Haven, CT (US)

(*) Notice: Subject to any disclaimer, the term of this patent is extended or adjusted under 35 U.S.C. 154(b) by 595 days.

(21) Appl. No.: 09/972,599

(22) Filed: Oct. 6, 2001

(65) Prior Publication Data

US 2002/0077295 A1 Jun. 20, 2002

Related U.S. Application Data

(63) Continuation-in-part of application No. 09/758,140, filed on Jan. 12, 2001, now abandoned, application No. 09/972,599, and a continuation-in-part of application No. PCT/US01/01040, filed on Jan. 12, 2001.

(60) Provisional application No. 60/236,378, filed on Sep. 29, 2000, provisional application No. 60/207,366, filed on May 26, 2000, provisional application No. 60/175,707, filed on Jan. 12, 2000.

(51) Int. Cl.
*C07K 14/00* (2006.01)
*C07K 5/00* (2006.01)
*A61K 38/00* (2006.01)

(52) U.S. Cl. .................. 530/350; 530/300; 514/2
(58) Field of Classification Search ............... 530/350, 530/300; 514/2
See application file for complete search history.

(56) References Cited

U.S. PATENT DOCUMENTS

| 5,250,414 A | 10/1993 | Schwab et al. ............ 435/7.72 |
| 5,684,133 A | 11/1997 | Schwab et al. ............ 530/350 |
| 5,858,708 A | 1/1999 | Bandman et al. .......... 435/69.1 |
| 6,025,333 A | 2/2000 | Schwab et al. ............ 514/18 |
| 6,475,753 B1 | 11/2002 | Ruben et al. |
| 6,627,741 B1 | 9/2003 | Ruben et al. |
| 6,774,216 B1 | 8/2004 | Ruben et al. |
| 2002/0012965 A1 | 1/2002 | Strittmatter |
| 2002/0055139 A1 | 5/2002 | Holtzman et al. |
| 2003/0124704 A1 | 7/2003 | Strittmatter et al. |
| 2005/0221420 A1 | 10/2005 | Barske et al. |
| 2005/0271655 A1 | 12/2005 | Lee et al. |

FOREIGN PATENT DOCUMENTS

| WO | WO 98/06841 | 2/1998 |
| WO | WO 99/46281 | 9/1999 |
| WO | WO 99/66041 | 12/1999 |
| WO | WO 00/05364 | 2/2000 |
| WO | WO 00/31235 | 6/2000 |
| WO | WO 00/32221 | 6/2000 |
| WO | WO 00/37638 | 6/2000 |
| WO | WO 00/53756 | 9/2000 |
| WO | WO 00/53758 | 9/2000 |
| WO | WO 00/58473 | 10/2000 |
| WO | WO 00/70050 | 11/2000 |
| WO | WO 00/73452 | 12/2000 |
| WO | WO 01/09162 | 2/2001 |
| WO | WO 01/51520 | 7/2001 |
| WO | WO 02/29059 A2 | 4/2002 |
| WO | WO 03/031462 A2 | 4/2003 |
| WO | WO 04/014311 A2 | 2/2004 |
| WO | WO 05/016955 A2 | 2/2005 |

OTHER PUBLICATIONS

Fournier, et al, 2001, Nature, 419: 341-346; Barton, et al, 2003, 22(13): 3291-3302.*
Barton, et al, 2003, 22(13): 3291-3302.*
Huizinga, et al, 2002, Science, 297: 1176-1179.*
Hall, A., 1998, Science, 278, 509-514.*
C. E. Bandtlow, et al., "NI-35/250/Nogo-A: A Neurite Growth Inhibitor Restricting Structural Plasticity and Regeneration of Nerve Fibers in the Adult Vertebrate CNS," *Glia*, 29(2), pp. 175-181 (2000).
M.S. Chen, et al., "Nogo-A is a Myelin-Associated Neurite Outgrowth Inhibitor and an Antigen for monoclonal Antibody IN-1," *Nature*, 403(6768), pp. 434-439 (2000).
A.E. Fournier, et al., "Identification of a Receptor Mediating Nogo-66 Inhibition of Axonal Regeneration," *Nature*, 409(6818), pp. 341-346 (2001).
T. GrandPre, et al., "Identification of the Nogo Inhibitor of Axon Regeneration as a Reticulon Protein," *Nature*, 403(6768), pp. 439-444 (2000).
P. Hu, et al., "*Homo Sapiens* Chromosome 22q11 PAC Clone p215k21 Distal to DGCR Region," *EMBL Database Entry AC006549*, Accession No. AC006549 (1999).
A.B. Huber, et al., "Nogo-A, a Potent Inhibitor of Neurite Outgrowth and Regeneration," *Biol. Chem.*, 381(5-6), pp. 407-419 (2000).
D. Merkler, et al., "Locomotor Recovery in Spinal Cord-Injured Rats Treated with an Antibody Neutralizing the Myelin-Associated Neurite Growth Inhibitor Nogo-A," *J. Neurosci.*, 21(10), pp. 3665-3673 (2001).

(Continued)

Primary Examiner—Eileen B. O'Hara
Assistant Examiner—Sandra Wegert
(74) *Attorney, Agent, or Firm*—Sterne, Kessler, Goldstein & Fox P.L.L.C.

(57) ABSTRACT

Disclosed are NgR proteins and biologically active Nogo (ligand) protein fragments. Also disclosed are compositions and methods for modulating the expression or activity of the Nogo and NgR protein. Also disclosed are peptides which block Nogo-mediated inhibition of axonal extension. The compositions and methods of the invention are useful in the treatment of cranial or cerebral trauma, spinal cord injury, stroke or a demyelinating disease.

50 Claims, 31 Drawing Sheets

OTHER PUBLICATIONS

M. Oudega, et al., "Neutralizing Antibodies Against Neurite Growth Inhibitor NI-35/250 Do Not Promote Regeneration of Sensory Axons in the Adult Rat Spinal Cord," *Neuroscience*, 100(4), pp. 873-883 (2000).

R. Prinjha, et al., "Inhibitor of Neurite Outgrowth in Humans," *Nature*, 430(6768), pp. 383-384 (2000).

O. Raineteau, et al., "Sprouting and Regeneration After Pyramidotomy and Blockade of the Myelin-Associated Neurite Growth Inhibitors N1 35/250 in Adult Rats," *Eur. J. Neurosci.*, 11(4), pp. 1486-1490 (1999).

O. Raineteau, et al., "Functional Switch Between Motor Tracts in the Presence of the mAB IN-1 in the Adult Rat," *Proc. Natl. Acad. Sci. U.S.A.*, 98(12), pp. 6929-6934 (2001).

A.A. Spillmann, et al., "Identification and Characterization of a Bovine Neurite Growth Inhibitor (bNI-22)," *J. Biol. Chem.*, 273(30), pp. 19283-19293 (1998).

M. Tatagiba, et al., "Regeneration of Injured Axons in the Adult Mammalian Central Nervous System," *Neurosurgery*, 40(3), pp. 541-547 (1997).

M. Thallmair, et al., "Neurite Growth Inhibitors Restrict Plasticity and Functional Recovery Following Corticospinal Tract Lesions," *Nat. Neurosci.*, 1(2), pp. 124-131 (1998).

W.J. Z'Graggen, et al., "Functional Recovery and Enhanced Corticofugal Plasticity After Unilateral Pyramidal Tract Lesion and Blockade of Myelin-Associated Neurite Growth Inhibitors in Adult Rats," *J. Neurosci.*, 18(12), pp. 4744-4757 (1998).

International Search Report for International Application No. PCT/US05/35719, ISA/US, Alexandria, VA, mailed Apr. 13, 2006.

Supplementary European Search Report for European Patent Application No. EP 02 80 0939, European Patent Office, mailed on Jun. 28, 2005.

Fournier, A.E., et al., "Characterization of the neuronal receptor mediating Nogo-66 inhibition of axonal regeneration," *J. Neurochem. 78 (Suppl. 1)*: 105, Blackwell Publishing, Abstract No. S08-01 (Sep. 2001).

Fournier, A.E., et al., "Nogo Receptor Domain Analysis," *Society for Neuroscience Abstracts*27:670, Society for Neuroscience, Abstract No. 258.3, presented at the *Society for Neuroscience's 31st Annual Meeting*, San Diego, CA (Nov. 12, 2001).

GrandPre, T.J., et al., "Functional Analysis of Nogo-66 and Nogo Receptor Domains," *Society for Neuroscience Abstracts*27:670, Society for Neuroscience, Abstract No. 258.4, presented at the *Society for Neuroscience's 31st Annual Meeting*, San Diego, CA (Nov. 12, 2001).

Domeniconi, M., et al., "Myelin-Associated Glycoprotein Interacts with the Nogo66 Receptor to Inhibit Neurite Outgrowth," *Neuron* 35:283-290, Cell Press (Jul. 2002).

GrandPré, T., et al., "Nogo-66 receptor antagonist peptide promotes axonal regeneration," *Nature*417:547-551, Nature Publishing Group (May 2002).

International Search Report for International Application No. PCT/US2005/002535, European Patent Office, Netherlands, mailed Oct. 24, 2005.

Li, M., et al., "Effect of soluble Nogo receptor treatment on functional and histological outcome after spinal cord injury in the rat," Biosis Database, Accession No. PREV200400194121, Abstract No. 80.22, *Presented at the 33rd Annual Meeting of the Society of Neuroscience*, New Orleans, LA (Nov. 8-12, 2003).

Li, W., et al., "A Neutralizing Anti-Nogo66 Receptor Monoclonal Antibody Reverses Inhibition of Neurite Outgrowth by Central Nervous System Myelin," *J. Biol. Chem.* 42:43780-43788, The American Society for Biochemistry and Molecular Biology, Inc. (Oct. 2004).

Li, W., et al., "Neutralization of NGR1 May be Sufficient to Promote Rat DRG Neurite Outgrowth in the Presence of CNS Myeline," SFN 2003 Abstract Viewer & Itinerary Planner, Program No. 678.3, *Presented at the 33rd Annual Meeting of the Society of Neuroscience*, New Orleans, LA (Nov. 8-12, 2003).

Oertle, T., et al., "Nogo-A Inhibits Neurite Outgrowth and Cell Spreading with Three Discrete Regions," *J. Neurosci.*23:5393-5406, Society for Neuroscience (Jul. 2003).

\* cited by examiner

Nogo Receptor 473 aa

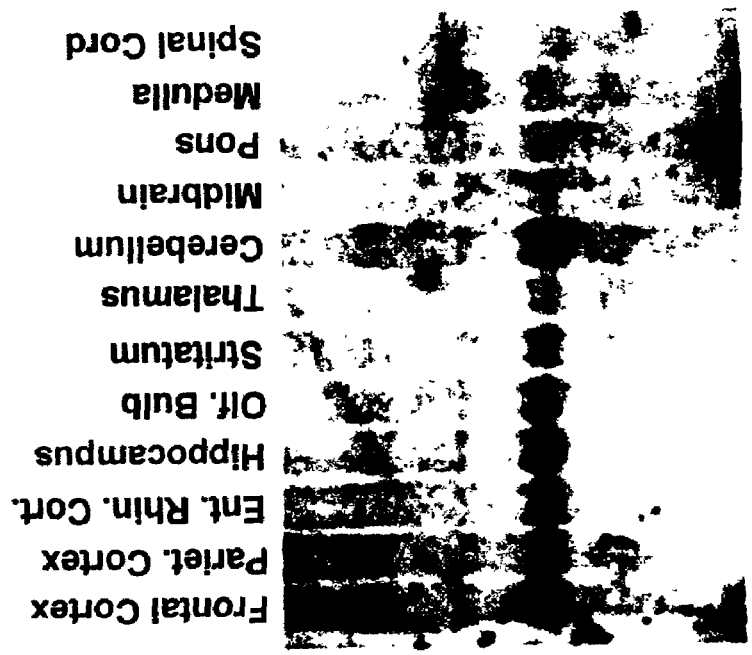
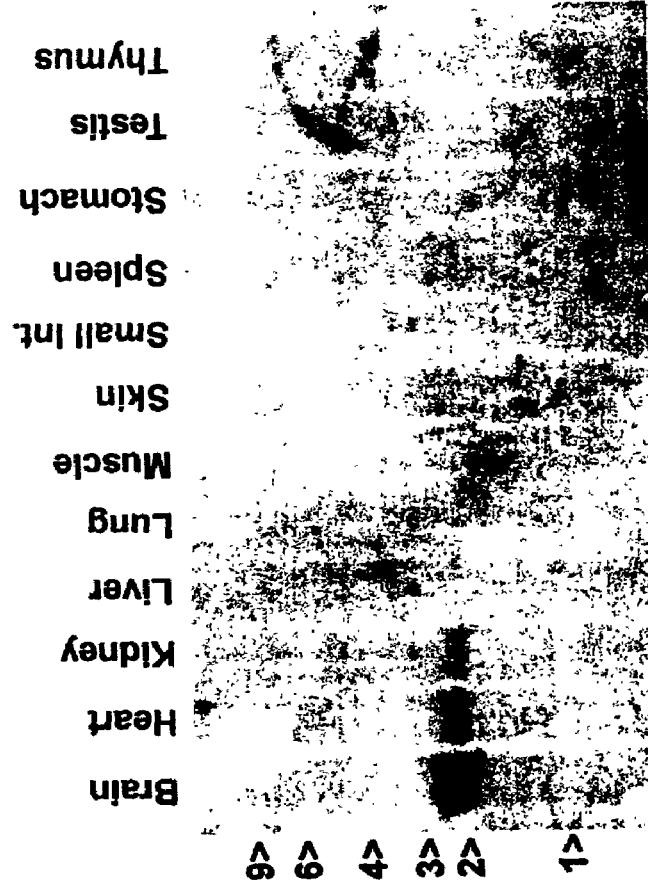
FIG. 8

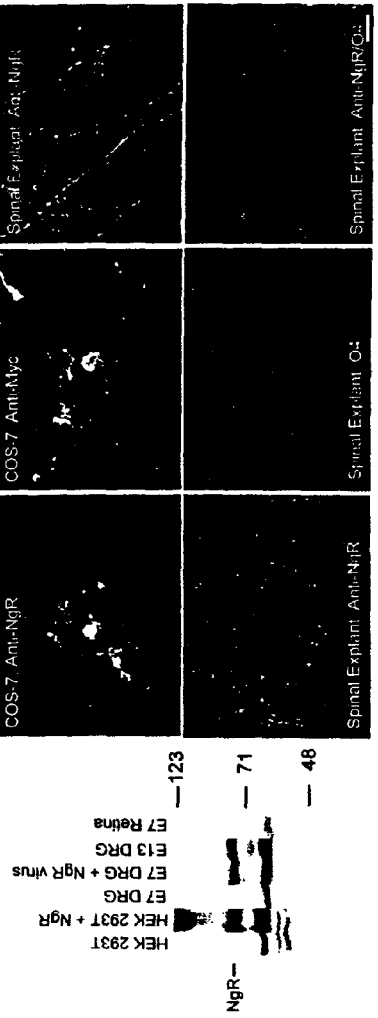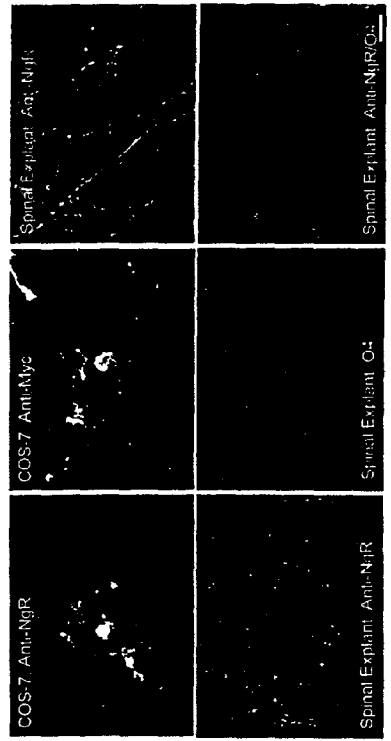

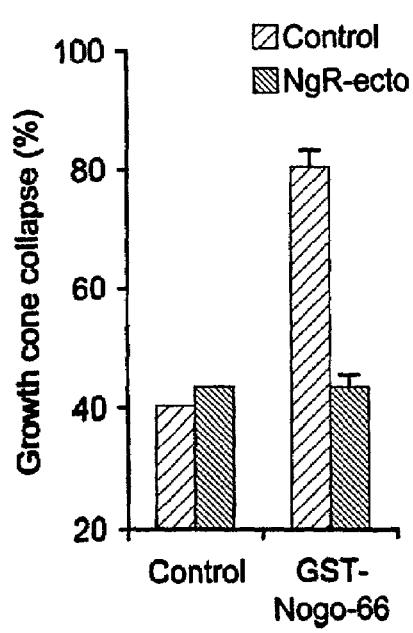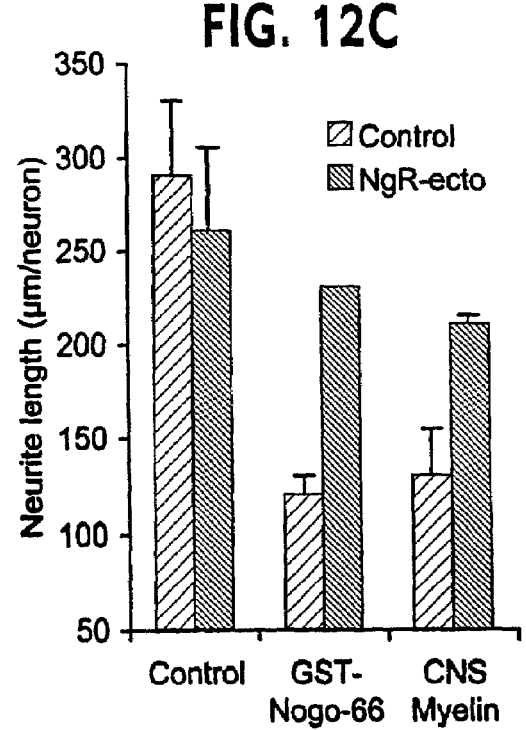
FIG. 12B
FIG. 12C

SEQUENCE LISTING

<160> NUMBER OF SEQ ID NOS: 55

<210> SEQ ID NO 1
<211> LENGTH: 1719
<212> TYPE: DNA
<213> ORGANISM: Homo sapiens
<220> FEATURE:
<221> NAME/KEY: CDS
<222> LOCATION: (166)..(1584)
<223> OTHER INFORMATION: Predicted human Nogo receptor gene

<400> SEQUENCE: 1

```
agcccagcca gagccgggcg gagcggagcg cgccgagcct cgtcccgcgg ccgggccggg      60
gccgggccgt agcggcggcg cctggatgcg gacccggccg cggggagacg ggcgcccgcc     120
ccgaaacgac tttcagtccc cgacgcgccc cgcccaaccc ctacg atg aag agg gcg    177
                                                   Met Lys Arg Ala
                                                     1 tcc gct gga ggg agc cgg ctg ctg gca tgg gtg ctg tgg ctg cag gcc      225
Ser Ala Gly Gly Ser Arg Leu Leu Ala Trp Val Leu Trp Leu Gln Ala
  5                  10                  15                  20 tgg cag gtg gca gcc cca tgc cca ggt gcc tgc gta tgc tac aat gag      273
Trp Gln Val Ala Ala Pro Cys Pro Gly Ala Cys Val Cys Tyr Asn Glu
                 25                  30                  35 ccc aag gtg acg aca agc tgc ccc cag cag ggc ctg cag gct gtg ccc      321
Pro Lys Val Thr Thr Ser Cys Pro Gln Gln Gly Leu Gln Ala Val Pro
```

|     |     |     |     |     |     |     |     |     |     |     |     |     |     |     |     |      |
|---|---|---|---|---|---|---|---|---|---|---|---|---|---|---|---|---|
|     |     |     | 40  |     |     |     | 45  |     |     |     | 50  |     |     |     |     |      |
| gtg | ggc | atc | cct | gct | gcc | agc | cag | cgc | atc | ttc | ctg | cac | ggc | aac | cgc | 369  |
| Val | Gly | Ile | Pro | Ala | Ala | Ser | Gln | Arg | Ile | Phe | Leu | His | Gly | Asn | Arg |      |
|     |     |     | 55  |     |     |     | 60  |     |     |     | 65  |     |     |     |     |      |
| atc | tcg | cat | gtg | cca | gct | gcc | agc | ttc | cgt | gcc | tgc | cgc | aac | ctc | acc | 417  |
| Ile | Ser | His | Val | Pro | Ala | Ala | Ser | Phe | Arg | Ala | Cys | Arg | Asn | Leu | Thr |      |
|     | 70  |     |     |     | 75  |     |     |     | 80  |     |     |     |     |     |     |      |
| atc | ctg | tgg | ctg | cac | tcg | aat | gtg | ctg | gcc | cga | att | gat | gcg | gct | gcc | 465  |
| Ile | Leu | Trp | Leu | His | Ser | Asn | Val | Leu | Ala | Arg | Ile | Asp | Ala | Ala | Ala |      |
| 85  |     |     |     | 90  |     |     |     | 95  |     |     |     | 100 |     |     |     |      |
| ttc | act | ggc | ctg | gcc | ctc | ctg | gag | cag | ctg | gac | ctc | agc | gat | aat | gca | 513  |
| Phe | Thr | Gly | Leu | Ala | Leu | Leu | Glu | Gln | Leu | Asp | Leu | Ser | Asp | Asn | Ala |      |
|     |     |     |     | 105 |     |     |     | 110 |     |     |     | 115 |     |     |     |      |
| cag | ctc | cgg | tct | gtg | gac | cct | gcc | aca | ttc | cac | ggc | ctg | ggc | cgc | cta | 561  |
| Gln | Leu | Arg | Ser | Val | Asp | Pro | Ala | Thr | Phe | His | Gly | Leu | Gly | Arg | Leu |      |
|     |     |     | 120 |     |     |     | 125 |     |     |     | 130 |     |     |     |     |      |
| cac | acg | ctg | cac | ctg | gac | cgc | tgc | ggc | ctg | cag | gag | ctg | ggc | ccg | ggg | 609  |
| His | Thr | Leu | His | Leu | Asp | Arg | Cys | Gly | Leu | Gln | Glu | Leu | Gly | Pro | Gly |      |
|     | 135 |     |     |     | 140 |     |     |     | 145 |     |     |     |     |     |     |      |
| ctg | ttc | cgc | ggc | ctg | gct | gcc | ctg | cag | tac | ctc | tac | ctg | cag | gac | aac | 657  |
| Leu | Phe | Arg | Gly | Leu | Ala | Ala | Leu | Gln | Tyr | Leu | Tyr | Leu | Gln | Asp | Asn |      |
| 150 |     |     |     | 155 |     |     |     | 160 |     |     |     |     |     |     |     |      |
| gcg | ctg | cag | gca | ctg | cct | gat | gac | acc | ttc | cgc | gac | ctg | ggc | aac | ctc | 705  |
| Ala | Leu | Gln | Ala | Leu | Pro | Asp | Asp | Thr | Phe | Arg | Asp | Leu | Gly | Asn | Leu |      |
| 165 |     |     |     |     | 170 |     |     |     | 175 |     |     |     | 180 |     |     |      |
| aca | cac | ctc | ttc | ctg | cac | ggc | aac | cgc | atc | tcc | agc | gtg | ccc | gag | cgc | 753  |
| Thr | His | Leu | Phe | Leu | His | Gly | Asn | Arg | Ile | Ser | Ser | Val | Pro | Glu | Arg |      |
|     |     |     |     | 185 |     |     |     | 190 |     |     |     | 195 |     |     |     |      |
| gcc | ttc | cgt | ggg | ctg | cac | agc | ctc | gac | cgt | ctc | cta | ctg | cac | cag | aac | 801  |
| Ala | Phe | Arg | Gly | Leu | His | Ser | Leu | Asp | Arg | Leu | Leu | Leu | His | Gln | Asn |      |
|     |     |     | 200 |     |     |     | 205 |     |     |     | 210 |     |     |     |     |      |
| cgc | gtg | gcc | cat | gtg | cac | ccg | cat | gcc | ttc | cgt | gac | ctt | ggc | cgc | ctc | 849  |
| Arg | Val | Ala | His | Val | His | Pro | His | Ala | Phe | Arg | Asp | Leu | Gly | Arg | Leu |      |
|     |     | 215 |     |     |     | 220 |     |     |     | 225 |     |     |     |     |     |      |
| atg | aca | ctc | tat | ctg | ttt | gcc | aac | aat | cta | tca | gcg | ctg | ccc | act | gag | 897  |
| Met | Thr | Leu | Tyr | Leu | Phe | Ala | Asn | Asn | Leu | Ser | Ala | Leu | Pro | Thr | Glu |      |
|     | 230 |     |     |     | 235 |     |     |     | 240 |     |     |     |     |     |     |      |
| gcc | ctg | gcc | ccc | ctg | cgt | gcc | ctg | cag | tac | ctg | agg | ctc | aac | gac | aac | 945  |
| Ala | Leu | Ala | Pro | Leu | Arg | Ala | Leu | Gln | Tyr | Leu | Arg | Leu | Asn | Asp | Asn |      |
| 245 |     |     |     | 250 |     |     |     | 255 |     |     |     | 260 |     |     |     |      |
| ccc | tgg | gtg | tgt | gac | tgc | cgg | gca | cgc | cca | ctc | tgg | gcc | tgg | ctg | cag | 993  |
| Pro | Trp | Val | Cys | Asp | Cys | Arg | Ala | Arg | Pro | Leu | Trp | Ala | Trp | Leu | Gln |      |
|     |     |     |     | 265 |     |     |     | 270 |     |     |     | 275 |     |     |     |      |
| aag | ttc | cgc | ggc | tcc | tcc | tcc | gag | gtg | ccc | tgc | agc | ctc | ccg | caa | cgc | 1041 |
| Lys | Phe | Arg | Gly | Ser | Ser | Ser | Glu | Val | Pro | Cys | Ser | Leu | Pro | Gln | Arg |      |
|     |     |     | 280 |     |     |     | 285 |     |     |     | 290 |     |     |     |     |      |
| ctg | gct | ggc | cgt | gac | ctc | aaa | cgc | cta | gct | gcc | aat | gac | ctg | cag | ggc | 1089 |
| Leu | Ala | Gly | Arg | Asp | Leu | Lys | Arg | Leu | Ala | Ala | Asn | Asp | Leu | Gln | Gly |      |
|     |     | 295 |     |     |     | 300 |     |     |     | 305 |     |     |     |     |     |      |
| tgc | gct | gtg | gcc | acc | ggc | cct | tac | cat | ccc | atc | tgg | acc | ggc | agg | gcc | 1137 |
| Cys | Ala | Val | Ala | Thr | Gly | Pro | Tyr | His | Pro | Ile | Trp | Thr | Gly | Arg | Ala |      |
|     | 310 |     |     |     | 315 |     |     |     | 320 |     |     |     |     |     |     |      |
| acc | gat | gag | gag | ccg | ctg | ggg | ctt | ccc | aag | tgc | tgc | cag | cca | gat | gcc | 1185 |
| Thr | Asp | Glu | Glu | Pro | Leu | Gly | Leu | Pro | Lys | Cys | Cys | Gln | Pro | Asp | Ala |      |
| 325 |     |     |     | 330 |     |     |     | 335 |     |     |     | 340 |     |     |     |      |
| gct | gac | aag | gcc | tca | gta | ctg | gag | cct | gga | aga | cca | gct | tcg | gca | ggc | 1233 |
| Ala | Asp | Lys | Ala | Ser | Val | Leu | Glu | Pro | Gly | Arg | Pro | Ala | Ser | Ala | Gly |      |
|     |     |     |     | 345 |     |     |     | 350 |     |     |     | 355 |     |     |     |      |
| aat | gcg | ctg | aag | gga | cgc | gtg | ccg | ccc | ggt | gac | agc | ccg | ccg | ggc | aac | 1281 |

```
                                                                                  -continued Asn Ala Leu Lys Gly Arg Val Pro Pro Gly Asp Ser Pro Pro Gly Asn
                360                 365                 370 ggc tct ggc cca cgg cac atc aat gac tca ccc ttt ggg act ctg cct      1329
Gly Ser Gly Pro Arg His Ile Asn Asp Ser Pro Phe Gly Thr Leu Pro
            375                 380                 385 ggc tct gct gag ccc ccg ctc act gca gtg cgg ccc gag ggc tcc gag      1377
Gly Ser Ala Glu Pro Pro Leu Thr Ala Val Arg Pro Glu Gly Ser Glu
        390                 395                 400 cca cca ggg ttc ccc acc tcg ggc cct cgc cgg agg cca ggc tgt tca      1425
Pro Pro Gly Phe Pro Thr Ser Gly Pro Arg Arg Arg Pro Gly Cys Ser
405                 410                 415                 420 cgc aag aac cgc acc cgc agc cac tgc cgt ctg ggc cag gca ggc agc      1473
Arg Lys Asn Arg Thr Arg Ser His Cys Arg Leu Gly Gln Ala Gly Ser
                425                 430                 435 ggg ggt ggc ggg act ggt gac tca gaa ggc tca ggt gcc cta ccc agc      1521
Gly Gly Gly Gly Thr Gly Asp Ser Glu Gly Ser Gly Ala Leu Pro Ser
            440                 445                 450 ctc acc tgc agc ctc acc ccc ctg ggc ctg gcg ctg gtg ctg tgg aca      1569
Leu Thr Cys Ser Leu Thr Pro Leu Gly Leu Ala Leu Val Leu Trp Thr
        455                 460                 465 gtg ctt ggg ccc tgc tgaccccag cggacacaag agcgtgctca gcagccaggt      1624
Val Leu Gly Pro Cys
    470 gtgtgtacat acgggtctc tctccacgcc gccaagccag ccgggcggcc gacccgtggg     1684 gcaggccagg ccaggtcctc cctgatggac gcctg                               1719

<210> SEQ ID NO 2
<211> LENGTH: 473
<212> TYPE: PRT
<213> ORGANISM: Homo sapiens

<400> SEQUENCE: 2

Met Lys Arg Ala Ser Ala Gly Gly Ser Arg Leu Leu Ala Trp Val Leu
  1               5                  10                  15

Trp Leu Gln Ala Trp Gln Val Ala Ala Pro Cys Pro Gly Ala Cys Val
                 20                  25                  30

Cys Tyr Asn Glu Pro Lys Val Thr Thr Ser Cys Pro Gln Gln Gly Leu
             35                  40                  45

Gln Ala Val Pro Val Gly Ile Pro Ala Ala Ser Gln Arg Ile Phe Leu
         50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Thr Phe Arg Asp
                165                 170                 175

Leu Gly Asn Leu Thr His Leu Phe Leu His Gly Asn Arg Ile Ser Ser
            180                 185                 190
```

```
Val Pro Glu Arg Ala Phe Arg Gly Leu His Ser Leu Asp Arg Leu Leu
    195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470

<210> SEQ ID NO 3
<211> LENGTH: 1866
<212> TYPE: DNA
<213> ORGANISM: Mus musculus
<220> FEATURE:
<221> NAME/KEY: CDS
<222> LOCATION: (178)..(1596)
<223> OTHER INFORMATION: Mouse Nogo receptor cDNA

<400> SEQUENCE: 3
agccgcagcc cgcgagccca gcccggcccg gtagagcgga gcgccggagc ctcgtcccgc      60
ggccgggccg ggaccgggcc ggagcagcgg cgcctggatg cggaccccgg ccgcgcgaga     120
cgggcgcccg ccccgaagcc gcttccagtg cccgacgcgc ccgctcgac cccgaag        177 yatg aag agg gcg tcc tcc gga gga agc agg ctg ctg gca tgg gtg tta     225
Met Lys Arg Ala Ser Ser Gly Gly Ser Arg Leu Leu Ala Trp Val Leu
  1               5                  10                  15 tgg cta cag gcc tgg agg gta gca aca cca tgc cct ggt gct tgt gtg     273
Trp Leu Gln Ala Trp Arg Val Ala Thr Pro Cys Pro Gly Ala Cys Val
             20                  25                  30
```

```
                                                            -continued tgc tac aat gag ccc aag gta aca aca agc tgc ccc cag cag ggt ctg      321
Cys Tyr Asn Glu Pro Lys Val Thr Thr Ser Cys Pro Gln Gln Gly Leu
             35                  40                  45 cag gct gtg ccc act ggc atc cca gcc tct agc cag cga atc ttc ctg      369
Gln Ala Val Pro Thr Gly Ile Pro Ala Ser Ser Gln Arg Ile Phe Leu
 50                  55                  60 cat ggc aac cga atc tct cac gtg cca gct gcg agc ttc cag tca tgc      417
His Gly Asn Arg Ile Ser His Val Pro Ala Ala Ser Phe Gln Ser Cys
 65                  70                  75                  80 cga aat ctc act atc ctg tgg ctg cac tct aat gcg ctg gct cgg atc      465
Arg Asn Leu Thr Ile Leu Trp Leu His Ser Asn Ala Leu Ala Arg Ile
                 85                  90                  95 gat gct gct gcc ttc act ggt ctg acc ctc ctg gag caa cta gat ctt      513
Asp Ala Ala Ala Phe Thr Gly Leu Thr Leu Leu Glu Gln Leu Asp Leu
            100                 105                 110 agt gat aat gca cag ctt cat gtc gtg gac cct acc acg ttc cac ggc      561
Ser Asp Asn Ala Gln Leu His Val Val Asp Pro Thr Thr Phe His Gly
        115                 120                 125 ctg ggc cac ctg cac aca ctg cac cta gac cga tgt ggc ctg cgg gag      609
Leu Gly His Leu His Thr Leu His Leu Asp Arg Cys Gly Leu Arg Glu
130                 135                 140 ctg ggt ccc ggc cta ttc cgt gga cta gca gct ctg cag tac ctc tac      657
Leu Gly Pro Gly Leu Phe Arg Gly Leu Ala Ala Leu Gln Tyr Leu Tyr
145                 150                 155                 160 cta caa gac aac aat ctg cag gca ctc cct gac aac acc ttt cga gac      705
Leu Gln Asp Asn Asn Leu Gln Ala Leu Pro Asp Asn Thr Phe Arg Asp
                165                 170                 175 ctg ggc aac ctc acg cat ctc ttt ctg cat ggc aac cgt atc ccc agt      753
Leu Gly Asn Leu Thr His Leu Phe Leu His Gly Asn Arg Ile Pro Ser
            180                 185                 190 gtg cct gag cac gct ttc cgt ggc ctg cac agt ctt gac cgc ctc ctc      801
Val Pro Glu His Ala Phe Arg Gly Leu His Ser Leu Asp Arg Leu Leu
        195                 200                 205 ttg cac cag aac cat gtg gct cgt gtg cac cca cat gcc ttc cgg gac      849
Leu His Gln Asn His Val Ala Arg Val His Pro His Ala Phe Arg Asp
210                 215                 220 ctt ggc cgc ctc atg acc ctc tac ctg ttt gcc aac aac ctc tcc atg      897
Leu Gly Arg Leu Met Thr Leu Tyr Leu Phe Ala Asn Asn Leu Ser Met
225                 230                 235                 240 ctg cct gca gag gtc cta atg ccc ctg agg tct ctg cag tac ctg cga      945
Leu Pro Ala Glu Val Leu Met Pro Leu Arg Ser Leu Gln Tyr Leu Arg
                245                 250                 255 ctc aat gac aac ccc tgg gtg tgt gac tgc cgg gca cgt cca ctc tgg      993
Leu Asn Asp Asn Pro Trp Val Cys Asp Cys Arg Ala Arg Pro Leu Trp
            260                 265                 270 gcc tgg ctg cag aag ttc cga ggt tcc tca tca gag gtg ccc tgc aac     1041
Ala Trp Leu Gln Lys Phe Arg Gly Ser Ser Ser Glu Val Pro Cys Asn
        275                 280                 285 ctg ccc caa cgc ctg gca gac cgt gat ctt aag cgc ctc gct gcc agt     1089
Leu Pro Gln Arg Leu Ala Asp Arg Asp Leu Lys Arg Leu Ala Ala Ser
290                 295                 300 gac cta gag ggc tgt gct gtg gct tca gga ccc ttc cgt ccc atc cag     1137
Asp Leu Glu Gly Cys Ala Val Ala Ser Gly Pro Phe Arg Pro Ile Gln
305                 310                 315                 320 acc agt cag ctc act gat gag gag ctg ctg agc ctc ccc aag tgc tgc     1185
Thr Ser Gln Leu Thr Asp Glu Glu Leu Leu Ser Leu Pro Lys Cys Cys
                325                 330                 335 cag cca gat gct gca gac aaa gcc tca gta ctg gaa ccc ggg agg cca     1233
Gln Pro Asp Ala Ala Asp Lys Ala Ser Val Leu Glu Pro Gly Arg Pro
```

-continued

```
                340                 345                 350
gct tct gcc gga aac gcc ctc aag gga cgt gtg cct ccc ggt gac act      1281
Ala Ser Ala Gly Asn Ala Leu Lys Gly Arg Val Pro Pro Gly Asp Thr
            355                 360                 365 cca cca ggc aat ggc tca ggc cct cgg cac atc aat gac tct cca ttt      1329
Pro Pro Gly Asn Gly Ser Gly Pro Arg His Ile Asn Asp Ser Pro Phe
        370                 375                 380 gga act ttg ccc agc tct gca gag ccc cca ctg act gcc ctg cgg cct      1377
Gly Thr Leu Pro Ser Ser Ala Glu Pro Pro Leu Thr Ala Leu Arg Pro
385                 390                 395                 400 ggg ggt tcc gag cca cca gga ctt ccc acc act ggt ccc cgc agg agg      1425
Gly Gly Ser Glu Pro Pro Gly Leu Pro Thr Thr Gly Pro Arg Arg Arg
                405                 410                 415 cca ggt tgt tcc cgg aag aat cgc acc cgc agc cac tgc cgt ctg ggc      1473
Pro Gly Cys Ser Arg Lys Asn Arg Thr Arg Ser His Cys Arg Leu Gly
            420                 425                 430 cag gcg gga agt ggg gcc agt gga aca ggg gac gca gag ggt tca ggg      1521
Gln Ala Gly Ser Gly Ala Ser Gly Thr Gly Asp Ala Glu Gly Ser Gly
        435                 440                 445 gct ctg cct gct ctg gcc tgc agc ctt gct cct ctg ggc ctt gca ctg      1569
Ala Leu Pro Ala Leu Ala Cys Ser Leu Ala Pro Leu Gly Leu Ala Leu
450                 455                 460 gta ctt tgg aca gtg ctt ggg ccc tgc tgaccagcca ccagccacca            1616
Val Leu Trp Thr Val Leu Gly Pro Cys
465                 470 ggtgtgtgta catatggggt ctccctccac gccgccagcc agagccaggg acaggctctg    1676
aggggcaggc caggccctcc ctgacagatg cctccccacc agcccacccc catctccacc    1736
ccatcatgtt tacagggttc cggggtggc ggttggttca aaccccaac ttccacccgg      1796 atcgcggcat atagacatat gaaatttatt ttacttgcgt aaaatatcgg atgacgtgga    1856
ataaacagct                                                           1866
```

<210> SEQ ID NO 4
<211> LENGTH: 473
<212> TYPE: PRT
<213> ORGANISM: Mus musculus

<400> SEQUENCE: 4

```
Met Lys Arg Ala Ser Ser Gly Gly Ser Arg Leu Leu Ala Trp Val Leu
  1               5                  10                  15

Trp Leu Gln Ala Trp Arg Val Ala Thr Pro Cys Pro Gly Ala Cys Val
                 20                  25                  30

Cys Tyr Asn Glu Pro Lys Val Thr Thr Ser Cys Pro Gln Gln Gly Leu
             35                  40                  45

Gln Ala Val Pro Thr Gly Ile Pro Ala Ser Ser Gln Arg Ile Phe Leu
         50                  55                  60

His Gly Asn Arg Ile Ser His Val Pro Ala Ala Ser Phe Gln Ser Cys
 65                  70                  75                  80

Arg Asn Leu Thr Ile Leu Trp Leu His Ser Asn Ala Leu Ala Arg Ile
                 85                  90                  95

Asp Ala Ala Ala Phe Thr Gly Leu Thr Leu Leu Glu Gln Leu Asp Leu
            100                 105                 110

Ser Asp Asn Ala Gln Leu His Val Val Asp Pro Thr Thr Phe His Gly
        115                 120                 125

Leu Gly His Leu His Thr Leu His Leu Asp Arg Cys Gly Leu Arg Glu
    130                 135                 140

Leu Gly Pro Gly Leu Phe Arg Gly Leu Ala Ala Leu Gln Tyr Leu Tyr
```

```
                145                 150                 155                 160
Leu Gln Asp Asn Asn Leu Gln Ala Leu Pro Asp Asn Thr Phe Arg Asp
                    165                 170                 175
Leu Gly Asn Leu Thr His Leu Phe Leu His Gly Asn Arg Ile Pro Ser
                180                 185                 190
Val Pro Glu His Ala Phe Arg Gly Leu His Ser Leu Asp Arg Leu Leu
            195                 200                 205
Leu His Gln Asn His Val Ala Arg Val His Pro His Ala Phe Arg Asp
        210                 215                 220
Leu Gly Arg Leu Met Thr Leu Tyr Leu Phe Ala Asn Asn Leu Ser Met
225                 230                 235                 240
Leu Pro Ala Glu Val Leu Met Pro Leu Arg Ser Leu Gln Tyr Leu Arg
                245                 250                 255
Leu Asn Asp Asn Pro Trp Val Cys Asp Cys Arg Ala Arg Pro Leu Trp
                260                 265                 270
Ala Trp Leu Gln Lys Phe Arg Gly Ser Ser Glu Val Pro Cys Asn
            275                 280                 285
Leu Pro Gln Arg Leu Ala Asp Arg Asp Leu Lys Arg Leu Ala Ala Ser
        290                 295                 300
Asp Leu Glu Gly Cys Ala Val Ala Ser Gly Pro Phe Arg Pro Ile Gln
305                 310                 315                 320
Thr Ser Gln Leu Thr Asp Glu Glu Leu Leu Ser Leu Pro Lys Cys Cys
                325                 330                 335
Gln Pro Asp Ala Ala Asp Lys Ala Ser Val Leu Glu Pro Gly Arg Pro
            340                 345                 350
Ala Ser Ala Gly Asn Ala Leu Lys Gly Arg Val Pro Pro Gly Asp Thr
        355                 360                 365
Pro Pro Gly Asn Gly Ser Gly Pro Arg His Ile Asn Asp Ser Pro Phe
    370                 375                 380
Gly Thr Leu Pro Ser Ser Ala Glu Pro Pro Leu Thr Ala Leu Arg Pro
385                 390                 395                 400
Gly Gly Ser Glu Pro Pro Gly Leu Pro Thr Thr Gly Pro Arg Arg Arg
                405                 410                 415
Pro Gly Cys Ser Arg Lys Asn Arg Thr Arg Ser His Cys Arg Leu Gly
            420                 425                 430
Gln Ala Gly Ser Gly Ala Ser Gly Thr Gly Asp Ala Glu Gly Ser Gly
        435                 440                 445
Ala Leu Pro Ala Leu Ala Cys Ser Leu Ala Pro Leu Gly Leu Ala Leu
    450                 455                 460
Val Leu Trp Thr Val Leu Gly Pro Cys
465                 470

<210> SEQ ID NO 5
<211> LENGTH: 4053
<212> TYPE: DNA
<213> ORGANISM: Homo sapiens
<220> FEATURE:
<221> NAME/KEY: CDS
<222> LOCATION: (135)..(3710)
<223> OTHER INFORMATION: Human DNA encoding for Nogo protein (KIAA0886,
      GenBank Accession No. AB020693)

<400> SEQUENCE: 5
caccacagta ggtccctcgg ctcagtcggc ccagccctc tcagtcctcc ccaaccccca        60
caaccgcccg cggtctctgag acgcggcccc ggcggcggcg gcagcagctg cagcatcatc      120
```

```
tccaccctcc agcc atg gaa gac ctg gac cag tct cct ctg gtc tcg tcc       170
              Met Glu Asp Leu Asp Gln Ser Pro Leu Val Ser Ser
              1               5                   10 tcg gac agc cca ccc cgg ccg cag ccc gcg ttc aag tac cag ttc gtg       218
Ser Asp Ser Pro Pro Arg Pro Gln Pro Ala Phe Lys Tyr Gln Phe Val
        15                  20                  25 agg gag ccc gag gac gag gag gaa gaa gag gag gag gaa gag gag gac       266
Arg Glu Pro Glu Asp Glu Glu Glu Glu Glu Glu Glu Glu Glu Glu Asp
30                  35                  40 gag gac gaa gac ctg gag gag ctg gag gtg ctg gag agg aag ccc gcc       314
Glu Asp Glu Asp Leu Glu Glu Leu Glu Val Leu Glu Arg Lys Pro Ala
45                  50                  55                  60 gcc ggg ctg tcc gcg gcc cca gtg ccc acc gcc cct gcc gcc ggc gcg       362
Ala Gly Leu Ser Ala Ala Pro Val Pro Thr Ala Pro Ala Ala Gly Ala
                65                  70                  75 ccc ctg atg gac ttc gga aat gac ttc gtg ccg ccg gcg ccc cgg gga       410
Pro Leu Met Asp Phe Gly Asn Asp Phe Val Pro Pro Ala Pro Arg Gly
            80                  85                  90 ccc ctg ccg gcc gct ccc ccc gtc gcc ccg gag cgg cag ccg tct tgg       458
Pro Leu Pro Ala Ala Pro Pro Val Ala Pro Glu Arg Gln Pro Ser Trp
        95                  100                 105 gac ccg agc ccg gtg tcg tcg acc gtg ccc gcg cca tcc ccg ctg tct       506
Asp Pro Ser Pro Val Ser Ser Thr Val Pro Ala Pro Ser Pro Leu Ser
    110                 115                 120 gct gcc gca gtc tcg ccc tcc aag ctc cct gag gac gac gag cct ccg       554
Ala Ala Ala Val Ser Pro Ser Lys Leu Pro Glu Asp Asp Glu Pro Pro
125                 130                 135                 140 gcc cgg cct ccc cct cct ccc ccg gcc agc gtg agc ccc cag gca gag       602
Ala Arg Pro Pro Pro Pro Pro Ala Ser Val Ser Pro Gln Ala Glu
                145                 150                 155 ccc gtg tgg acc ccg cca gcc ccg gct ccc gcc gcg ccc ccc tcc acc       650
Pro Val Trp Thr Pro Pro Ala Pro Ala Pro Ala Ala Pro Pro Ser Thr
            160                 165                 170 ccg gcc gcg ccc aag cgc agg ggc tcc tcg ggc tca gtg gat gag acc       698
Pro Ala Ala Pro Lys Arg Arg Gly Ser Ser Gly Ser Val Asp Glu Thr
        175                 180                 185 ctt ttt gct ctt cct gct gca tct gag cct gta ata cgc tcc tct gca       746
Leu Phe Ala Leu Pro Ala Ala Ser Glu Pro Val Ile Arg Ser Ser Ala
    190                 195                 200 gaa aat atg gac ttg aag gag cag cca ggt aac act att tcg gct ggt       794
Glu Asn Met Asp Leu Lys Glu Gln Pro Gly Asn Thr Ile Ser Ala Gly
205                 210                 215                 220 caa gag gat ttc cca tct gtc ctg ctt gaa act gct gct tct ctt cct       842
Gln Glu Asp Phe Pro Ser Val Leu Leu Glu Thr Ala Ala Ser Leu Pro
                225                 230                 235 tct ctg tct cct ctc tca gcc gct tct ttc aaa gaa cat gaa tac ctt       890
Ser Leu Ser Pro Leu Ser Ala Ala Ser Phe Lys Glu His Glu Tyr Leu
            240                 245                 250 ggt aat ttg tca aca gta tta ccc act gaa gga aca ctt caa gaa aat       938
Gly Asn Leu Ser Thr Val Leu Pro Thr Glu Gly Thr Leu Gln Glu Asn
        255                 260                 265 gtc agt gaa gct tct aaa gag gtc tca gag aag gca aaa act cta ctc       986
Val Ser Glu Ala Ser Lys Glu Val Ser Glu Lys Ala Lys Thr Leu Leu
    270                 275                 280 ata gat aga gat tta aca gag ttt tca gaa tta gaa tac tca gaa atg      1034
Ile Asp Arg Asp Leu Thr Glu Phe Ser Glu Leu Glu Tyr Ser Glu Met
285                 290                 295                 300 gga tca tcg ttc agt gtc tct cca aaa gca gaa tct gcc gta ata gta      1082
Gly Ser Ser Phe Ser Val Ser Pro Lys Ala Glu Ser Ala Val Ile Val
                305                 310                 315
```

```
                                                                -continued gca aat cct agg gaa gaa ata atc gtg aaa aat aaa gat gaa gaa gag      1130
Ala Asn Pro Arg Glu Glu Ile Ile Val Lys Asn Lys Asp Glu Glu Glu
        320                 325                 330 aag tta gtt agt aat aac atc ctt cat aat caa caa gag tta cct aca      1178
Lys Leu Val Ser Asn Asn Ile Leu His Asn Gln Gln Glu Leu Pro Thr
    335                 340                 345 gct ctt act aaa ttg gtt aaa gag gat gaa gtt gtg tct tca gaa aaa      1226
Ala Leu Thr Lys Leu Val Lys Glu Asp Glu Val Val Ser Ser Glu Lys
350                 355                 360 gca aaa gac agt ttt aat gaa aag aga gtt gca gtg gaa gct cct atg      1274
Ala Lys Asp Ser Phe Asn Glu Lys Arg Val Ala Val Glu Ala Pro Met
365                 370                 375                 380 agg gag gaa tat gca gac ttc aaa cca ttt gag cga gta tgg gaa gtg      1322
Arg Glu Glu Tyr Ala Asp Phe Lys Pro Phe Glu Arg Val Trp Glu Val
                385                 390                 395 aaa gat agt aag gaa gat agt gat atg ttg gct gct gga ggt aaa atc      1370
Lys Asp Ser Lys Glu Asp Ser Asp Met Leu Ala Ala Gly Gly Lys Ile
        400                 405                 410 gag agc aac ttg gaa agt aaa gtg gat aaa aaa tgt ttt gca gat agc      1418
Glu Ser Asn Leu Glu Ser Lys Val Asp Lys Lys Cys Phe Ala Asp Ser
    415                 420                 425 ctt gag caa act aat cac gaa aaa gat agt gag agt agt aat gat gat      1466
Leu Glu Gln Thr Asn His Glu Lys Asp Ser Glu Ser Ser Asn Asp Asp
430                 435                 440 act tct ttc ccc agt acg cca gaa ggt ata aag gat cgt tca gga gca      1514
Thr Ser Phe Pro Ser Thr Pro Glu Gly Ile Lys Asp Arg Ser Gly Ala
445                 450                 455                 460 tat atc aca tgt gct ccc ttt aac cca gca gca act gag agc att gca      1562
Tyr Ile Thr Cys Ala Pro Phe Asn Pro Ala Ala Thr Glu Ser Ile Ala
                465                 470                 475 aca aac att ttt cct ttg tta gga gat cct act tca gaa aat aag acc      1610
Thr Asn Ile Phe Pro Leu Leu Gly Asp Pro Thr Ser Glu Asn Lys Thr
        480                 485                 490 gat gaa aaa aaa ata gaa gaa aag aag gcc caa ata gta aca gag aag      1658
Asp Glu Lys Lys Ile Glu Glu Lys Lys Ala Gln Ile Val Thr Glu Lys
    495                 500                 505 aat act agc acc aaa aca tca aac cct ttt ctt gta gca gca cag gat      1706
Asn Thr Ser Thr Lys Thr Ser Asn Pro Phe Leu Val Ala Ala Gln Asp
510                 515                 520 tct gag aca gat tat gtc aca aca gat aat tta aca aag gtg act gag      1754
Ser Glu Thr Asp Tyr Val Thr Thr Asp Asn Leu Thr Lys Val Thr Glu
525                 530                 535                 540 gaa gtc gtg gca aac atg cct gaa ggc ctg act cca gat tta gta cag      1802
Glu Val Val Ala Asn Met Pro Glu Gly Leu Thr Pro Asp Leu Val Gln
                545                 550                 555 gaa gca tgt gaa agt gaa ttg aat gaa gtt act ggt aca aag att gct      1850
Glu Ala Cys Glu Ser Glu Leu Asn Glu Val Thr Gly Thr Lys Ile Ala
        560                 565                 570 tat gaa aca aaa atg gac ttg gtt caa aca tca gaa gtt atg caa gag      1898
Tyr Glu Thr Lys Met Asp Leu Val Gln Thr Ser Glu Val Met Gln Glu
    575                 580                 585 tca ctc tat cct gca gca cag ctt tgc cca tca ttt gaa gag tca gaa      1946
Ser Leu Tyr Pro Ala Ala Gln Leu Cys Pro Ser Phe Glu Glu Ser Glu
590                 595                 600 gct act cct tca cca gtt ttg cct gac att gtt atg gaa gca cca ttg      1994
Ala Thr Pro Ser Pro Val Leu Pro Asp Ile Val Met Glu Ala Pro Leu
605                 610                 615                 620 aat tct gca gtt cct agt gct ggt gct tcc gtg ata cag ccc agc tca      2042
Asn Ser Ala Val Pro Ser Ala Gly Ala Ser Val Ile Gln Pro Ser Ser
```

```
                    625                 630                 635
tca cca tta gaa gct tct tca gtt aat tat gaa agc ata aaa cat gag          2090
Ser Pro Leu Glu Ala Ser Ser Val Asn Tyr Glu Ser Ile Lys His Glu
            640                 645                 650 cct gaa aac ccc cca cca tat gaa gag gcc atg agt gta tca cta aaa          2138
Pro Glu Asn Pro Pro Pro Tyr Glu Glu Ala Met Ser Val Ser Leu Lys
        655                 660                 665 aaa gta tca gga ata aag gaa gaa att aaa gag cct gaa aat att aat          2186
Lys Val Ser Gly Ile Lys Glu Glu Ile Lys Glu Pro Glu Asn Ile Asn
    670                 675                 680 gca gct ctt caa gaa aca gaa gct cct tat ata tct att gca tgt gat          2234
Ala Ala Leu Gln Glu Thr Glu Ala Pro Tyr Ile Ser Ile Ala Cys Asp
685                 690                 695                 700 tta att aaa gaa aca aag ctt tct gct gaa cca gct ccg gat ttc tct          2282
Leu Ile Lys Glu Thr Lys Leu Ser Ala Glu Pro Ala Pro Asp Phe Ser
                705                 710                 715 gat tat tca gaa atg gca aaa gtt gaa cag cca gtg cct gat cat tct          2330
Asp Tyr Ser Glu Met Ala Lys Val Glu Gln Pro Val Pro Asp His Ser
            720                 725                 730 gag cta gtt gaa gat tcc tca cct gat tct gaa cca gtt gac tta ttt          2378
Glu Leu Val Glu Asp Ser Ser Pro Asp Ser Glu Pro Val Asp Leu Phe
        735                 740                 745 agt gat gat tca ata cct gac gtt cca caa aaa caa gat gaa act gtg          2426
Ser Asp Asp Ser Ile Pro Asp Val Pro Gln Lys Gln Asp Glu Thr Val
    750                 755                 760 atg ctt gtg aaa gaa agt ctc act gag act tca ttt gag tca atg ata          2474
Met Leu Val Lys Glu Ser Leu Thr Glu Thr Ser Phe Glu Ser Met Ile
765                 770                 775                 780 gaa tat gaa aat aag gaa aaa ctc agt gct ttg cca cct gag gga gga          2522
Glu Tyr Glu Asn Lys Glu Lys Leu Ser Ala Leu Pro Pro Glu Gly Gly
                785                 790                 795 aag cca tat ttg gaa tct ttt aag ctc agt tta gat aac aca aaa gat          2570
Lys Pro Tyr Leu Glu Ser Phe Lys Leu Ser Leu Asp Asn Thr Lys Asp
            800                 805                 810 acc ctg tta cct gat gaa gtt tca aca ttg agc aaa aag gag aaa att          2618
Thr Leu Leu Pro Asp Glu Val Ser Thr Leu Ser Lys Lys Glu Lys Ile
        815                 820                 825 cct ttg cag atg gag gag ctc agt act gca gtt tat tca aat gat gac          2666
Pro Leu Gln Met Glu Glu Leu Ser Thr Ala Val Tyr Ser Asn Asp Asp
    830                 835                 840 tta ttt att tct aag gaa gca cag ata aga gaa act gaa acg ttt tca          2714
Leu Phe Ile Ser Lys Glu Ala Gln Ile Arg Glu Thr Glu Thr Phe Ser
845                 850                 855                 860 gat tca tct cca att gaa att ata gat gag ttc cct aca ttg atc agt          2762
Asp Ser Ser Pro Ile Glu Ile Ile Asp Glu Phe Pro Thr Leu Ile Ser
                865                 870                 875 tct aaa act gat tca ttt tct aaa tta gcc agg gaa tat act gac cta          2810
Ser Lys Thr Asp Ser Phe Ser Lys Leu Ala Arg Glu Tyr Thr Asp Leu
            880                 885                 890 gaa gta tcc cac aaa agt gaa att gct aat gcc ccg gat gga gct ggg          2858
Glu Val Ser His Lys Ser Glu Ile Ala Asn Ala Pro Asp Gly Ala Gly
        895                 900                 905 tca ttg cct tgc aca gaa ttg ccc cat gac ctt tct ttg aag aac ata          2906
Ser Leu Pro Cys Thr Glu Leu Pro His Asp Leu Ser Leu Lys Asn Ile
    910                 915                 920 caa ccc aaa gtt gaa gag aaa atc agt ttc tca gat gac ttt tct aaa          2954
Gln Pro Lys Val Glu Glu Lys Ile Ser Phe Ser Asp Asp Phe Ser Lys
925                 930                 935                 940 aat ggg tct gct aca tca aag gtg ctc tta ttg cct cca gat gtt tct          3002
```

```
Asn Gly Ser Ala Thr Ser Lys Val Leu Leu Pro Pro Asp Val Ser
            945                 950                 955 gct ttg gcc act caa gca gag ata gag agc ata gtt aaa ccc aaa gtt     3050
Ala Leu Ala Thr Gln Ala Glu Ile Glu Ser Ile Val Lys Pro Lys Val
        960                 965                 970 ctt gtg aaa gaa gct gag aaa aaa ctt cct tcc gat aca gaa aaa gag     3098
Leu Val Lys Glu Ala Glu Lys Lys Leu Pro Ser Asp Thr Glu Lys Glu
    975                 980                 985 gac aga tca cca tct gct ata ttt tca gca gag ctg agt aaa act tca     3146
Asp Arg Ser Pro Ser Ala Ile Phe Ser Ala Glu Leu Ser Lys Thr Ser
990                 995                 1000 gtt gtt gac ctc ctg tac tgg aga gac att aag aag act gga gtg gtg     3194
Val Val Asp Leu Leu Tyr Trp Arg Asp Ile Lys Lys Thr Gly Val Val
1005                1010                1015                1020 ttt ggt gcc agc cta ttc ctg ctg ctt tca ttg aca gta ttc agc att     3242
Phe Gly Ala Ser Leu Phe Leu Leu Leu Ser Leu Thr Val Phe Ser Ile
                1025                1030                1035 gtg agc gta aca gcc tac att gcc ttg gcc ctg ctc tct gtg acc atc     3290
Val Ser Val Thr Ala Tyr Ile Ala Leu Ala Leu Leu Ser Val Thr Ile
            1040                1045                1050 agc ttt agg ata tac aag ggt gtg atc caa gct atc cag aaa tca gat     3338
Ser Phe Arg Ile Tyr Lys Gly Val Ile Gln Ala Ile Gln Lys Ser Asp
        1055                1060                1065 gaa ggc cac cca ttc agg gca tat ctg gaa tct gaa gtt gct ata tct     3386
Glu Gly His Pro Phe Arg Ala Tyr Leu Glu Ser Glu Val Ala Ile Ser
    1070                1075                1080 gag gag ttg gtt cag aag tac agt aat tct gct ctt ggt cat gtg aac     3434
Glu Glu Leu Val Gln Lys Tyr Ser Asn Ser Ala Leu Gly His Val Asn
1085                1090                1095                1100 tgc acg ata aag gaa ctc agg cgc ctc ttc tta gtt gat gat tta gtt     3482
Cys Thr Ile Lys Glu Leu Arg Arg Leu Phe Leu Val Asp Asp Leu Val
                1105                1110                1115 gat tct ctg aag ttt gca gtg ttg atg tgg gta ttt acc tat gtt ggt     3530
Asp Ser Leu Lys Phe Ala Val Leu Met Trp Val Phe Thr Tyr Val Gly
            1120                1125                1130 gcc ttg ttt aat ggt ctg aca cta ctg att ttg gct ctc att tca ctc     3578
Ala Leu Phe Asn Gly Leu Thr Leu Leu Ile Leu Ala Leu Ile Ser Leu
        1135                1140                1145 ttc agt gtt cct gtt att tat gaa cgg cat cag gca cag ata gat cat     3626
Phe Ser Val Pro Val Ile Tyr Glu Arg His Gln Ala Gln Ile Asp His
    1150                1155                1160 tat cta gga ctt gca aat aag aat gtt aaa gat gct atg gct aaa atc     3674
Tyr Leu Gly Leu Ala Asn Lys Asn Val Lys Asp Ala Met Ala Lys Ile
1165                1170                1175                1180 caa gca aaa atc cct gga ttg aag cgc aaa gct gaa tgaaaacgcc          3720
Gln Ala Lys Ile Pro Gly Leu Lys Arg Lys Ala Glu
                1185                1190 caaataatt agtaggagtt catctttaaa ggggatattc atttgattat acggggagg     3780 gtcagggaag aacgaacctt gacgttgcag tgcagtttca cagatcgttg ttagatcttt   3840 attttagcc atgcactgtt gtgaggaaaa attacctgtc ttgactgcca tgtgttcatc    3900
atcttaagta ttgtaagctg ctatgtatgg atttaaaccg taatcatatc tttttcctat   3960
ctgaggcact ggtggaataa aaaacctgta tattttactt tgttgcagat agtcttgccg   4020
catcttggca agttgcagag atggtggagc tag                                4053

<210> SEQ ID NO 6
<211> LENGTH: 1192
<212> TYPE: PRT
```

-continued

<213> ORGANISM: Homo sapiens

<400> SEQUENCE: 6

Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro Glu
            20                  25                  30

Asp Glu Glu Glu Glu Glu Glu Glu Glu Asp Glu Asp Glu Asp
                35                  40                  45

Leu Glu Glu Leu Glu Val Leu Glu Arg Lys Pro Ala Ala Gly Leu Ser
        50                  55                  60

Ala Ala Pro Val Pro Thr Ala Pro Ala Ala Gly Ala Pro Leu Met Asp
65                  70                  75                  80

Phe Gly Asn Asp Phe Val Pro Ala Pro Arg Gly Pro Leu Pro Ala
                85                  90                  95

Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
            115                 120                 125

Ser Pro Ser Lys Leu Pro Glu Asp Asp Glu Pro Pro Ala Arg Pro Pro
    130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
            180                 185                 190

Pro Ala Ala Ser Glu Pro Val Ile Arg Ser Ser Ala Glu Asn Met Asp
        195                 200                 205

Leu Lys Glu Gln Pro Gly Asn Thr Ile Ser Ala Gly Gln Glu Asp Phe
210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
            260                 265                 270

Ser Lys Glu Val Ser Glu Lys Ala Lys Thr Leu Leu Ile Asp Arg Asp
    275                 280                 285

Leu Thr Glu Phe Ser Glu Leu Glu Tyr Ser Glu Met Gly Ser Ser Phe
290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Lys Leu Val Ser
                325                 330                 335

Asn Asn Ile Leu His Asn Gln Gln Glu Leu Pro Thr Ala Leu Thr Lys
            340                 345                 350

Leu Val Lys Glu Asp Glu Val Val Ser Ser Glu Lys Ala Lys Asp Ser
        355                 360                 365

Phe Asn Glu Lys Arg Val Ala Val Glu Ala Pro Met Arg Glu Glu Tyr
    370                 375                 380

Ala Asp Phe Lys Pro Phe Glu Arg Val Trp Glu Val Lys Asp Ser Lys
385                 390                 395                 400

```
Glu Asp Ser Asp Met Leu Ala Ala Gly Gly Lys Ile Glu Ser Asn Leu
            405                 410                 415
Glu Ser Lys Val Asp Lys Lys Cys Phe Ala Asp Ser Leu Glu Gln Thr
            420                 425                 430
Asn His Glu Lys Asp Ser Glu Ser Ser Asn Asp Asp Thr Ser Phe Pro
            435                 440                 445
Ser Thr Pro Glu Gly Ile Lys Asp Arg Ser Gly Ala Tyr Ile Thr Cys
    450                 455                 460
Ala Pro Phe Asn Pro Ala Ala Thr Glu Ser Ile Ala Thr Asn Ile Phe
465                 470                 475                 480
Pro Leu Leu Gly Asp Pro Thr Ser Glu Asn Lys Thr Asp Glu Lys Lys
                485                 490                 495
Ile Glu Glu Lys Lys Ala Gln Ile Val Thr Glu Lys Asn Thr Ser Thr
            500                 505                 510
Lys Thr Ser Asn Pro Phe Leu Val Ala Ala Gln Asp Ser Glu Thr Asp
    515                 520                 525
Tyr Val Thr Thr Asp Asn Leu Thr Lys Val Thr Glu Glu Val Val Ala
    530                 535                 540
Asn Met Pro Glu Gly Leu Thr Pro Asp Leu Val Gln Glu Ala Cys Glu
545                 550                 555                 560
Ser Glu Leu Asn Glu Val Thr Gly Thr Lys Ile Ala Tyr Glu Thr Lys
                565                 570                 575
Met Asp Leu Val Gln Thr Ser Glu Val Met Gln Glu Ser Leu Tyr Pro
            580                 585                 590
Ala Ala Gln Leu Cys Pro Ser Phe Glu Ser Glu Ala Thr Pro Ser
    595                 600                 605
Pro Val Leu Pro Asp Ile Val Met Glu Ala Pro Leu Asn Ser Ala Val
    610                 615                 620
Pro Ser Ala Gly Ala Ser Val Ile Gln Pro Ser Ser Pro Leu Glu
625                 630                 635                 640
Ala Ser Ser Val Asn Tyr Glu Ser Ile Lys His Glu Pro Glu Asn Pro
                645                 650                 655
Pro Pro Tyr Glu Glu Ala Met Ser Val Ser Leu Lys Lys Val Ser Gly
            660                 665                 670
Ile Lys Glu Glu Ile Lys Glu Pro Glu Asn Ile Asn Ala Ala Leu Gln
    675                 680                 685
Glu Thr Glu Ala Pro Tyr Ile Ser Ile Ala Cys Asp Leu Ile Lys Glu
    690                 695                 700
Thr Lys Leu Ser Ala Glu Pro Ala Pro Asp Phe Ser Asp Tyr Ser Glu
705                 710                 715                 720
Met Ala Lys Val Glu Gln Pro Val Pro Asp His Ser Glu Leu Val Glu
                725                 730                 735
Asp Ser Ser Pro Asp Ser Glu Pro Val Asp Leu Phe Ser Asp Asp Ser
            740                 745                 750
Ile Pro Asp Val Pro Gln Lys Gln Asp Glu Thr Val Met Leu Val Lys
    755                 760                 765
Glu Ser Leu Thr Glu Thr Ser Phe Glu Ser Met Ile Glu Tyr Glu Asn
    770                 775                 780
Lys Glu Lys Leu Ser Ala Leu Pro Pro Glu Gly Gly Lys Pro Tyr Leu
785                 790                 795                 800
Glu Ser Phe Lys Leu Ser Leu Asp Asn Thr Lys Asp Thr Leu Leu Pro
                805                 810                 815
Asp Glu Val Ser Thr Leu Ser Lys Lys Glu Lys Ile Pro Leu Gln Met
```

-continued

```
                  820                 825                 830
Glu Glu Leu Ser Thr Ala Val Tyr Ser Asn Asp Asp Leu Phe Ile Ser
        835                 840                 845
Lys Glu Ala Gln Ile Arg Glu Thr Glu Thr Phe Ser Asp Ser Ser Pro
850                 855                 860
Ile Glu Ile Ile Asp Glu Phe Pro Thr Leu Ile Ser Ser Lys Thr Asp
865                 870                 875                 880
Ser Phe Ser Lys Leu Ala Arg Glu Tyr Thr Asp Leu Glu Val Ser His
                885                 890                 895
Lys Ser Glu Ile Ala Asn Ala Pro Asp Gly Ala Gly Ser Leu Pro Cys
                900                 905                 910
Thr Glu Leu Pro His Asp Leu Ser Leu Lys Asn Ile Gln Pro Lys Val
            915                 920                 925
Glu Glu Lys Ile Ser Phe Ser Asp Asp Phe Ser Lys Asn Gly Ser Ala
930                 935                 940
Thr Ser Lys Val Leu Leu Pro Pro Asp Val Ser Ala Leu Ala Thr
945                 950                 955                 960
Gln Ala Glu Ile Glu Ser Ile Val Lys Pro Lys Val Leu Val Lys Glu
                965                 970                 975
Ala Glu Lys Lys Leu Pro Ser Asp Thr Glu Lys Glu Asp Arg Ser Pro
            980                 985                 990
Ser Ala Ile Phe Ser Ala Glu Leu Ser Lys Thr Ser Val Val Asp Leu
        995                 1000                1005
Leu Tyr Trp Arg Asp Ile Lys Lys Thr Gly Val Val Phe Gly Ala Ser
        1010                1015                1020
Leu Phe Leu Leu Leu Ser Leu Thr Val Phe Ser Ile Val Ser Val Thr
1025                1030                1035                1040
Ala Tyr Ile Ala Leu Ala Leu Leu Ser Val Thr Ile Ser Phe Arg Ile
                1045                1050                1055
Tyr Lys Gly Val Ile Gln Ala Ile Gln Lys Ser Asp Glu Gly His Pro
            1060                1065                1070
Phe Arg Ala Tyr Leu Glu Ser Glu Val Ala Ile Ser Glu Glu Leu Val
        1075                1080                1085
Gln Lys Tyr Ser Asn Ser Ala Leu Gly His Val Asn Cys Thr Ile Lys
        1090                1095                1100
Glu Leu Arg Arg Leu Phe Leu Val Asp Asp Leu Val Asp Ser Leu Lys
1105                1110                1115                1120
Phe Ala Val Leu Met Trp Val Phe Thr Tyr Val Gly Ala Leu Phe Asn
                1125                1130                1135
Gly Leu Thr Leu Leu Ile Leu Ala Leu Ile Ser Leu Phe Ser Val Pro
                1140                1145                1150
Val Ile Tyr Glu Arg His Gln Ala Gln Ile Asp His Tyr Leu Gly Leu
            1155                1160                1165
Ala Asn Lys Asn Val Lys Asp Ala Met Ala Lys Ile Gln Ala Lys Ile
        1170                1175                1180
Pro Gly Leu Lys Arg Lys Ala Glu
1185                1190

<210> SEQ ID NO 7
<211> LENGTH: 75
<212> TYPE: DNA
<213> ORGANISM: Artificial Sequence
<220> FEATURE:
<223> OTHER INFORMATION: Description of Artificial Sequence: cDNA
      encoding receptor binding inhibitor Pep 1
```

-continued

```
<400> SEQUENCE: 7
tttaggatat acaagggtgt gatccaagct atccagaaat cagatgaagg ccacccattc        60
agggcatatc tggaa                                                         75

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Pep1- Nogo
      protein inhibitor

<400> SEQUENCE: 8

Phe Arg Ile Tyr Lys Gly Val Ile Gln Ala Ile Gln Lys Ser Asp Glu
 1               5                  10                  15

Gly His Pro Phe Arg Ala Tyr Leu Glu
             20                  25

<210> SEQ ID NO 9
<211> LENGTH: 75
<212> TYPE: DNA
<213> ORGANISM: Artificial Sequence
<220> FEATURE:
<223> OTHER INFORMATION: Description of Artificial Sequence: cDNA
      encoding receptor binding inhibitor Pep2

<400> SEQUENCE: 9
atccagaaat cagatgaagg ccacccattc agggcatatc tggaatctga agttgctata        60
tctgaggagt tggtt                                                         75

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Pep2- Nogo
      protein inhibitor

<400> SEQUENCE: 10

Ile Gln Lys Ser Asp Glu Gly His Pro Phe Arg Ala Tyr Leu Glu Ser
 1               5                  10                  15

Glu Val Ala Ile Ser Glu Glu Leu Val
             20                  25

<210> SEQ ID NO 11
<211> LENGTH: 75
<212> TYPE: DNA
<213> ORGANISM: Artificial Sequence
<220> FEATURE:
<223> OTHER INFORMATION: Description of Artificial Sequence: cDNA
      encoding receptor binding inhibitor Pep3

<400> SEQUENCE: 11
agggcatatc tggaatctga agttgctata tctgaggagt tggttcagaa gtacagtaat        60
tctgctcttg gtcat                                                         75

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Pep3- Nogo
      protein inhibitor
```

-continued

<400> SEQUENCE: 12

Arg Ala Tyr Leu Glu Ser Glu Val Ala Ile Ser Glu Glu Leu Val Gln
 1               5                   10                  15

Lys Tyr Ser Asn Ser Ala Leu Gly His
            20                  25

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: cDNA
      encoding receptor binding inhibitor Pep4

<400> SEQUENCE: 13
tctgaggagt tggttcagaa gtacagtaat tctgctcttg gtcatgtgaa ctgcacgata       60
aaggaactca ggcgc                                                       75

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Pep4- Nogo
      protein inhibitor

<400> SEQUENCE: 14

Ser Glu Glu Leu Val Gln Lys Tyr Ser Asn Ser Ala Leu Gly His Val
 1               5                   10                  15

Asn Cys Thr Ile Lys Glu Leu Arg Arg
            20                  25

<210> SEQ ID NO 15
<211> LENGTH: 75
<212> TYPE: DNA
<213> ORGANISM: Artificial Sequence
<220> FEATURE:
<223> OTHER INFORMATION: Description of Artificial Sequence: cDNA
      encoding receptor binding inhibitor Pep5

<400> SEQUENCE: 15
gctcttggtc atgtgaactg cacgataaag gaactcaggc gcctcttctt agttgatgat       60
ttagttgatt ctctg                                                       75

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Pep5- Nogo
      protein inhibitor

<400> SEQUENCE: 16

Ala Leu Gly His Val Asn Cys Thr Ile Lys Glu Leu Arg Arg Leu Phe
 1               5                   10                  15

Leu Val Asp Asp Leu Val Asp Ser Leu
            20                  25

<210> SEQ ID NO 17
<211> LENGTH: 120
<212> TYPE: DNA
<213> ORGANISM: Artificial Sequence
<220> FEATURE:

```
<223> OTHER INFORMATION: Description of Artificial Sequence: cDNA
      encoding receptor binding inhibitor Pep2-41

<400

```
                  50                  55                  60

Ser Leu
 65

<210> SEQ ID NO 21
<211> LENGTH: 198
<212> TYPE: DNA
<213> ORGANISM: Homo sapiens
<220> FEATURE:
<223> OTHER INFORMATION: Nucleotide sequence encoding amino acids
      1055-1120 of human NogoA

<400> SEQUENCE: 21
aggatataca agggtgtgat ccaagctatc cagaaatcag atgaaggcca cccattcagg      60
gcatatctgg aatctgaagt tgctatatct gaggagttgg ttcagaagta cagtaattct    120
gctcttggtc atgtgaactg cacgataaag gaactcaggc gcctcttctt agttgatgat    180
ttagttgatt ctctgaag                                                  198

<210> SEQ ID NO 22
<211> LENGTH: 66
<212> TYPE: PRT
<213> ORGANISM: Homo sapiens

<400> SEQUENCE: 22

Arg Ile Tyr Lys Gly Val Ile Gln Ala Ile Gln Lys Ser Asp Glu Gly
 1               5                  10                  15

His Pro Phe Arg Ala Tyr Leu Glu Ser Glu Val Ala Ile Ser Glu Glu
            20                  25                  30

Leu Val Gln Lys Tyr Ser Asn Ser Ala Leu Gly His Val Asn Cys Thr
        35                  40                  45

Ile Lys Glu Leu Arg Arg Leu Phe Leu Val Asp Asp Leu Val Asp Ser
    50                  55                  60

Leu Lys
 65

<210> SEQ ID NO 23
<211> LENGTH: 75
<212> TYPE: DNA
<213> ORGANISM: Homo sapiens
<220> FEATURE:
<223> OTHER INFORMATION: Nucleotide sequence encoding amino acids
      1055-1079 of human NogoA

<400> SEQUENCE: 23
aggatataca agggtgtgat ccaagctatc cagaaatcag atgaaggcca cccattcagg      60
gcatatctgg aatct                                                      75

<210> SEQ ID NO 24
<211> LENGTH: 25
<212> TYPE: PRT
<213> ORGANISM: Homo sapiens

<400> SEQUENCE: 24

Arg Ile Tyr Lys Gly Val Ile Gln Ala Ile Gln Lys Ser Asp Glu Gly
 1               5                  10                  15

His Pro Phe Arg Ala Tyr Leu Glu Ser
            20                  25

<210> SEQ ID NO 25
<211> LENGTH: 90
```

```
<212> TYPE: DNA
<213> ORGANISM: Homo sapiens
<220> FEATURE:
<223> OTHER INFORMATION: Nucleotide sequence encoding amino acids
      1055-1084 of human NogoA

<400> SEQUENCE: 25
aggatataca agggtgtgat ccaagctatc cagaaatcag atgaaggcca cccattcagg    60
gcatatctgg aatctgaagt tgctatatct                                     90

<210> SEQ ID NO 26
<211> LENGTH: 31
<212> TYPE: PRT
<213> ORGANISM: Homo sapiens

<400> SEQUENCE: 26

Arg Ile Tyr Lys Gly Val Ile Gln Ala Ile Gln Lys Ser Asp Glu Gly
  1               5                  10                  15

His Pro Phe Arg Ala Tyr Leu Glu Ser Glu Ser Val Ala Ile Ser
             20                  25                  30

<210> SEQ ID NO 27
<211> LENGTH: 105
<212> TYPE: DNA
<213> ORGANISM: Homo sapiens
<220> FEATURE:
<223> OTHER INFORMATION: Nucleotide sequence encoding amino acids
      1055-1089 of human NogoA

<400> SEQUENCE: 27
aggatataca agggtgtgat ccaagctatc cagaaatcag atgaaggcca cccattcagg    60
gcatatctgg aatctgaagt tgctatatct gaggagttgg ttcag                   105

<210> SEQ ID NO 28
<211> LENGTH: 36
<212> TYPE: PRT
<213> ORGANISM: Homo sapiens

<400> SEQUENCE: 28

Arg Ile Tyr Lys Gly Val Ile Gln Ala Ile Gln Lys Ser Asp Glu Gly
  1               5                  10                  15

His Pro Phe Arg Ala Tyr Leu Glu Ser Glu Ser Val Ala Ile Ser Glu
             20                  25                  30

Glu Leu Val Gln
         35

<210> SEQ ID NO 29
<211> LENGTH: 105
<212> TYPE: DNA
<213> ORGANISM: Homo sapiens
<220> FEATURE:
<223> OTHER INFORMATION: Nucleotide sequence encoding amino acids
      1060-1094 of human NogoA

<400> SEQUENCE: 29
gtgatccaag ctatccagaa atcagatgaa ggccacccat caggggcata tctggaatct    60
gaagttgcta tatctgagga gttggttcag aagtacagta attct                   105

<210> SEQ ID NO 30
<211> LENGTH: 36
<212> TYPE: PRT
<213> ORGANISM: Homo sapiens
```

```
<400> SEQUENCE: 30

Val Ile Gln Ala Ile Gln Lys Ser Asp Glu Gly His Pro Phe Arg Ala
 1               5                  10                  15

Tyr Leu Glu Ser Glu Ser Val Ala Ile Ser Glu Glu Leu Val Gln Lys
                20                  25                  30

Tyr Ser Asn Ser
            35

<210> SEQ ID NO 31
<211> LENGTH: 90
<212> TYPE: DNA
<213> ORGANISM: Homo sapiens
<220> FEATURE:
<223> OTHER INFORMATION: Nucleotide sequence encoding amino acids
      1065-1094 of human NogoA

<400> SEQUENCE: 31
cagaaatcag atgaaggcca cccattcagg gcatatctgg aatctgaagt tgctatatct      60
gaggagttgg ttcagaagta cagtaattct                                      90

<210> SEQ ID NO 32
<211> LENGTH: 31
<212> TYPE: PRT
<213> ORGANISM: Homo sapiens

<400> SEQUENCE: 32

Gln Lys Ser Asp Glu Gly His Pro Phe Arg Ala Tyr Leu Glu Ser Glu
 1               5                  10                  15

Ser Val Ala Ile Ser Glu Glu Leu Val Gln Lys Tyr Ser Asn Ser
                20                  25                  30

<210> SEQ ID NO 33
<211> LENGTH: 75
<212> TYPE: DNA
<213> ORGANISM: Homo sapiens
<220> FEATURE:
<223> OTHER INFORMATION: Nucleotide sequence encoding amino acids
      1070-1094 of human NogoA

<400> SEQUENCE: 33
ggccacccat tcagggcata tctggaatct gaagttgcta tatctgagga gttggttcag      60
aagtacagta attct                                                      75

<210> SEQ ID NO 34
<211> LENGTH: 26
<212> TYPE: PRT
<213> ORGANISM: Homo sapiens

<400> SEQUENCE: 34

Gly His Pro Phe Arg Ala Tyr Leu Glu Ser Glu Ser Val Ala Ile Ser
 1               5                  10                  15

Glu Glu Leu Val Gln Lys Tyr Ser Asn Ser
                20                  25

<210> SEQ ID NO 35
<211> LENGTH: 75
<212> TYPE: DNA
<213> ORGANISM: Homo sapiens
<220> FEATURE:
<223> OTHER INFORMATION: Nucleotide sequence encoding amino acids
      1085-1109 of human NogA

<400> SEQUENCE: 35
```

```
gaggagttgg ttcagaagta cagtaattct gctcttggtc atgtgaactg cacgataaag    60
gaactcaggc gcctc                                                      75

<210> SEQ ID NO 36
<211> LENGTH: 25
<212> TYPE: PRT
<213> ORGANISM: Homo sapiens

<400> SEQUENCE: 36

Glu Glu Leu Val Gln Lys Tyr Ser Asn Ser Ala Leu Gly His Val Asn
 1               5                  10                  15

Cys Thr Ile Lys Glu Leu Arg Arg Leu
            20                  25

<210> SEQ ID NO 37
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 37
tgggatccga acaaaaactc atctcagaag aggatctgtc tagccagcga atcttcctgc    60
atggc                                                                 65

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 38
ttctcgaggt cagcagggcc caagcactgt cc                                   32

<210> SEQ ID NO 39
<211> LENGTH: 62
<212> TYPE: DNA
<213> ORGANISM: Artificial Sequence
<220> FEATURE:
<223> OTHER INFORMATION: Description of Artificial Sequence: Primer

<400> SEQUENCE: 39
tgggatccga acaaaaactc atctcagaag aggatctgct agagggctgt gctgtggctt    60
ca                                                                    62

<210> SEQ ID NO 40
<211> LENGTH: 63
<212> TYPE: DNA
<213> ORGANISM: Artificial Sequence
<220> FEATURE:
<223> OTHER INFORMATION: Description of Artificial Sequence: Primer

<400> SEQUENCE: 40
tgggatccga acaaaaactc atctcagaag aggatctgcc atgccctggt gcttgtgtgt    60
gct                                                                   63

<210> SEQ ID NO 41
<211> LENGTH: 34
<212> TYPE: DNA
<213> ORGANISM: Artificial Sequence
<220> FEATURE:
```

<223> OTHER INFORMATION: Description of Artificial Sequence: Primer

<400> SEQUENCE: 41
ttgcggccgc tgaagccaca gcacagccct ctag                    34

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 42
ttgcggccgc tgagggttca ggggctctgc ctgct                   35

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 43
ggctgggatg ccagtgggca cagc                               24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 44
ctcctggagc aactagatct tagt                               24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 45
ggtcagacca gtgaaggcag cagc                               24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 46
gctctgcagt acctctacct acaa                               24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 47
tgctagtcca cggaataggc cggg                               24

```
<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 48
agtcttgacc gcctcctctt gcac                                    24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 49
gtgcaggcca cggaaagcgt gctc                                    24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 50
tctctgcagt acctgcgact caat                                    24

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 51
gtggcttcag gacccttccg tcccatc                                 27

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 52
gtcattgagt cgcaggtact gcagagacct                              30

<210> SEQ ID NO 53
<211> LENGTH: 137
<212> TYPE: PRT
<213> ORGANISM: Homo sapiens
<220> FEATURE:
<223> OTHER INFORMATION: Residues 306-442 of human NogoR1

<400> SEQUENCE: 53

Leu Gln Gly Cys Ala Val Ala Thr Gly Pro Tyr His Pro Ile Trp Thr
 1               5                  10                  15

Gly Arg Ala Thr Asp Glu Glu Pro Leu Gly Leu Pro Lys Cys Cys Gln
                20                  25                  30

Pro Asp Ala Ala Asp Lys Ala Ser Val Leu Glu Pro Gly Arg Pro Ala
            35                  40                  45

Ser Ala Gly Asn Ala Leu Lys Gly Arg Val Pro Pro Gly Asp Ser Pro
```

```
             50                  55                  60
Pro Gly Asn Gly Ser Gly Pro Arg His Ile Asn Asp Ser Pro Phe Gly
 65                  70                  75                  80

Thr Leu Pro Gly Ser Ala Glu Pro Pro Leu Thr Ala Val Arg Pro Glu
                 85                  90                  95

Gly Ser Glu Pro Pro Gly Phe Pro Thr Ser Gly Pro Arg Arg Arg Pro
                100                 105                 110

Gly Cys Ser Arg Lys Asn Arg Thr Arg Ser His Cys Arg Leu Gly Gln
                115                 120                 125

Ala Gly Ser Gly Gly Gly Thr Gly
                130                 135

<210> SEQ ID NO 54
<211> LENGTH: 168
<212> TYPE: PRT
<213> ORGANISM: Homo sapiens
<220> FEATURE:
<223> OTHER INFORMATION: Residues 306-473 of human NogoR1

<400> SEQUENCE: 54

Leu Gln Gly Cys Ala Val Ala Thr Gly Pro Tyr His Pro Ile Trp Thr
  1               5                  10                  15

Gly Arg Ala Thr Asp Glu Glu Pro Leu Gly Leu Pro Lys Cys Cys Gln
                 20                  25                  30

Pro Asp Ala Ala Asp Lys Ala Ser Val Leu Glu Pro Gly Arg Pro Ala
                 35                  40                  45

Ser Ala Gly Asn Ala Leu Lys Gly Arg Val Pro Pro Gly Asp Ser Pro
     50                  55                  60

Pro Gly Asn Gly Ser Gly Pro Arg His Ile Asn Asp Ser Pro Phe Gly
 65                  70                  75                  80

Thr Leu Pro Gly Ser Ala Glu Pro Pro Leu Thr Ala Val Arg Pro Glu
                 85                  90                  95

Gly Ser Glu Pro Pro Gly Phe Pro Thr Ser Gly Pro Arg Arg Arg Pro
                100                 105                 110

Gly Cys Ser Arg Lys Asn Arg Thr Arg Ser His Cys Arg Leu Gly Gln
                115                 120                 125

Ala Gly Ser Gly Gly Gly Thr Gly Asp Ser Glu Gly Ser Gly Ala
                130                 135                 140

Leu Pro Ser Leu Thr Cys Ser Leu Thr Pro Leu Gly Leu Ala Leu Val
145                 150                 155                 160

Leu Trp Thr Val Leu Gly Pro Cys
                165

<210> SEQ ID NO 55
<211> LENGTH: 283
<212> TYPE: PRT
<213> ORGANISM: Homo sapiens
<220> FEATURE:
<223> OTHER INFORMATION: Residues 27-309 of human NogoR1

<400> SEQUENCE: 55

Cys Pro Gly Ala Cys Val Cys Tyr Asn Glu Pro Lys Val Thr Thr Ser
  1               5                  10                  15

Cys Pro Gln Gln Gly Leu Gln Ala Val Pro Val Gly Ile Pro Ala Ala
                 20                  25                  30

Ser Gln Arg Ile Phe Leu His Gly Asn Arg Ile Ser His Val Pro Ala
                 35                  40                  45
```

-continued

```
Ala Ser Phe Arg Ala Cys Arg Asn Leu Thr Ile Leu Trp Leu His Ser
    50                  55                  60
Asn Val Leu Ala Arg Ile Asp Ala Ala Ala Phe Thr Gly Leu Ala Leu
65                  70                  75                  80
Leu Glu Gln Leu Asp Leu Ser Asp Asn Ala Gln Leu Arg Ser Val Asp
                85                  90                  95
Pro Ala Thr Phe His Gly Leu Gly Arg Leu His Thr Leu His Leu Asp
                100                 105                 110
Arg Cys Gly Leu Gln Glu Leu Gly Pro Gly Leu Phe Arg Gly Leu Ala
            115                 120                 125
Ala Leu Gln Tyr Leu Tyr Leu Gln Asp Asn Ala Leu Gln Ala Leu Pro
    130                 135                 140
Asp Asp Thr Phe Arg Asp Leu Gly Asn Leu Thr His Leu Phe Leu His
145                 150                 155                 160
Gly Asn Arg Ile Ser Ser Val Pro Glu Arg Ala Phe Arg Gly Leu His
                165                 170                 175
Ser Leu Asp Arg Leu Leu Leu His Gln Asn Arg Val Ala His Val His
                180                 185                 190
Pro His Ala Phe Arg Asp Leu Gly Arg Leu Met Thr Leu Tyr Leu Phe
    195                 200                 205
Ala Asn Asn Leu Ser Ala Leu Pro Thr Glu Ala Leu Ala Pro Leu Arg
    210                 215                 220
Ala Leu Gln Tyr Leu Arg Leu Asn Asp Asn Pro Trp Val Cys Asp Cys
225                 230                 235                 240
Arg Ala Arg Pro Leu Trp Ala Trp Leu Gln Lys Phe Arg Gly Ser Ser
            245                 250                 255
Ser Glu Val Pro Cys Ser Leu Pro Gln Arg Leu Ala Gly Arg Asp Leu
            260                 265                 270
Lys Arg Leu Ala Ala Asn Asp Leu Gln Gly Cys
    275                 280
```

NOGO RECEPTOR-MEDIATED BLOCKADE OF AXONAL GROWTH

CROSS-REFERENCE TO RELATED APPLICATIONS

This application is a continuation-in-part of U.S. application Ser. No. 09/758,140, filed Jan. 12, 2001 now abandoned, which claims benefit from U.S. Provisional Patent Applications 60/175,707 filed Jan. 12, 2000; 60/207,366 filed May 26, 2000; 60/236,378 filed Sep. 29, 2000 which are herein incorporated by reference in their entirety. This application is also a continuation-in-part of international application PCT/US01/01040, filed Jan. 12, 2001.

U.S. GOVERNMENT SUPPORT

This invention was partially made with government support under National Institute of Health Grant RO1-NS 33020, RO1-NS39962 and RO1-NS42304.

FIELD OF THE INVENTION

The invention relates to neurology and molecular biology. More particularly, the invention relates to CNS neurons and axonal growth

BACKGROUND OF THE INVENTION

Axons and dendrites of neurons are long cellular extensions from neurons. At the distal tip of an extending axon or neurite is a specialized region, known as the growth cone. Growth cones are responsible for sensing the local environment and moving toward the neuron's target cell. Growth cones are hand shaped, with several long filopodia that differentially adhere to surfaces in the embryo. Growth cones can be sensitive to several guidance cues, for example, surface adhesiveness, growth factors, neurotransmitters and electric fields. The guidance of growth at the cone depends on various classes of adhesion molecules, intercellular signals, as well as factors which stimulate and inhibit growth cones. The growth cone located at the end of a growing neurite advances at various rates, but typically at the speed of one to two millimeters per day. The cone consists of a broad and flat expansion, with numerous long microspikes or filopodia that extend like spikes. These filopodia are continually active. While some filopodia retract back into the growth cone, others continue to elongate through the substratum. The elongations between different filopodia form lamellipodia.

The growth cone can explore the area that is ahead of it and on either side with its lamellipodia and filopodia. When an elongation comes in contact with a surface that is unfavorable, it withdraws. When an elongation comes into contact with a favorable surface, it continues to extend and can manipulate the growth cone moving in that direction. Hence, the growth cone can be guided by small variations in surface properties of the substrata. When the growth cone reaches an appropriate target cell a synaptic connection is created.

Damaged neurons do not regenerate in the central nervous system (CNS) following injury due to trauma and disease. The absence of axon regeneration following injury can be attributed to the presence of axon growth inhibitors. These inhibitors are predominantly associated with myelin and constitute an important barrier to regeneration. Axon growth inhibitors are present in CNS-derived myelin and the plasma membrane of oligodendrocytes, which synthesize myelin in the CNS (Schwab et al., (1993) Ann. Rev. Neurosci. 16, 565–595).

CNS myelin is an elaborate extension of the oligodendrocyte cell membrane. A single oligodendrocyte myelinates as many as thirty different CNS axonal segments. Oligodendrocyte membrane extensions wrap around the axons in a concentric fashion to form the myelin sheath. Tightly compacted mature myelin consists of parallel layers of bimolecular lipids apposed to layers of hydrated protein. Active myelin synthesis starts in utero and continues for the first two years of human life. Slower synthesis continues through childhood and adolescence while turnover of mature myelin continues at a slower rate throughout adult life. Both developing and mature forms of myelin are susceptible to injury from disease or physical trauma resulting in degradation of the myelin surrounding axons.

Myelin-associated inhibitors appear to be a primary contributor to the failure of CNS axon regeneration in vivo after an interruption of axonal continuity, while other non-myelin associated axon growth inhibitors in the CNS may play a lesser role. These inhibitors block axonal regeneration following neuronal injury due to trauma, stroke, or viral infection.

Numerous myelin-derived axon growth inhibitors have been characterized (see, for review, David et al., (1999) WO9953945; Bandman et al., (1999) U.S. Pat. No. 5,858, 708; Schwab, (1996) Neurochem. Res. 21, 755–761). Several components of CNS white matter, NI35, NI250 (Nogo) and Myelin-associated glycoprotein (MAG), which have inhibitory activity for axonal extension, have been also been described (Schwab et al., (1990) WO9005191; Schwab et al., (1997) U.S. Pat. No. 5,684,133). In particular, Nogo is a 250 kDa myelin-associated axon growth inhibitor which has been cloned and characterized (Nagase et al., (1998) DNA Res. 5, 355–364; Schwab, (1990) Exp. Neurol. 109, 2–5). The Nogo cDNA was first identified through random analysis of brain cDNA and had no suggested function (Nagase et al., (1998) DNA Res. 5, 355–364).

Schwab and colleagues published the sequence of six peptides randomly derived from a proteolytic digest of presumed bovine NI250 (Nogo) protein (Spillmann et al., (1998) J. Biol. Chem. 273, 19283–19293). A probable fill-length cDNA sequence for this protein was recently deposited in the GenBank. This 4.1 kilobase human cDNA clone, KIAA0886, is derived from the Kazusa DNA Research Institute effort to sequence random high molecular weight brain-derived cDNA (Nagase et al., (1998) DNA Res. 31, 355–364). This novel cDNA clone encodes a 135 kDa protein that includes all six of the peptide sequences derived from bovine Nogo.

The human Nogo-A sequence shares high homology over its carboxyl third with the Reticulon (Rtn) protein family. Rtn1 has also been termed neuro-endocrine specific protein (NSP) because it is expressed exclusively in neuro-endocrine cells (Van de Velde et al., (1994) J. Cell. Sci. 107, 2403–2416). All Rtn proteins share a 200 amino acid residue region of sequence similarity at the carboxyl terminus of the protein (Van de Velde et al., (1994) J. Cell. Sci. 107, 2403–2416; Roebroek et al, (1996) Genomics 32, 191–199; Roebroek et al., (1998) Genomics 51, 98–106; Moreira et al., (1999) Genomics 58, 73–81; Morris et al., (1991) Biochim. Biophys. Acta 1450, 68–76). Related sequences have been recognized in the fly and worm genomes (Moreira et al., (1999) Genomics 58, 73–81). This region is approximately 70% identical across the Rtn family. Amino terminal regions are not related to one another and are derived from various alternative RNA splicing events.

From analysis of sequences deposited in the GenBank and by homology with published Rtn1 isoforms, three forms of the Nogo protein are predicted (Nogo-A, Nogo-B, Nogo-C). Nogo-B of 37 kDa might possibly correspond to NI35, and explain the antigenic relatedness of the NI35 and NI250 (Nogo-A) axon outgrowth inhibiting activity. Nogo-C-Myc exhibits an electrophoretic mobility of 25 kDa by SDS-PAGE and has been described previously as Rtn4 and vp2015. The ability of Nogo-A protein to inhibit axonal regeneration has been recognized only recently (GrandPré et al., (2000) Nature 403, 439–444; Chen et al., (2000) Nature 403, 434–439; Prinjha et al., (2000) Nature 403, 483–484).

The absence of re-extension of axons across lesions in the CNS following injury has been attributed as a cause of the permanent deleterious effects associated with trauma, stroke and demyelinating disorders. Modulation of NI250 has been described as a means for treatment of regeneration for neurons damaged by trauma, infarction and degenerative disorders of the CNS (Schwab et al., (1994) WO9417831; Tatagiba et al., (1997) Neurosurgery 40, 541–546) as well as malignant tumors in the CNS such as glioblastoma (Schwab et al., (1993) U.S. Pat. No. 5,250,414; Schwab et al., (2000) U.S. Pat. No. 6,025,333).

Antibodies which recognize NI250 have been reported to be useful in the diagnosis and treatment of nerve damage resulting from trauma, infarction and degenerative disorders of the CNS (Schnell & Schwab, (1990) Nature 343, 269–272; Schwab et al., (1997) U.S. Pat. No. 5,684,133). In axons which become myelinated, there is a correlation with the development of myelin and the appearance of Nogo. After Nogo is blocked by antibodies, neurons can again extend across lesions caused by nerve damage (Varga et al., (1995) Proc. Natl. Acad. Sci. USA 92, 10959–10963).

The mechanism of action whereby Nogo inhibits axonal growth has not yet been elucidated. Identification and characterization of this mechanism of action and the biochemical pathways associated with the effects of Nogo would be useful in treatment of disease states associated with axonal injury and axonal demyelination.

SUMMARY OF THE INVENTION

Genes encoding murine and human receptors for Nogo (NgR) have been discovered. Various domains in the NgR polypeptide have been identified, and certain of their functions have been discovered. In addition, important aspects of the interaction of specific regions of the Nogo polypeptide (ligand) with NgR have been discovered. Based on these and other discoveries, the invention features molecules and methods useful for decreasing Nogo-dependent inhibition of axonal growth in CNS neurons.

The invention includes a NgR-derived polypeptide that contains amino acid residues 27–309 of SEQ ID NO:2 (human NgR NTLRRCT domain), while containing fewer than 115 consecutive amino acids from amino acids 310–445 of SEQ ID NO:2 (human NgR CTS domain). The NgR NTLRRCT domain optionally includes up to 20 conservative amino acid substitutions. In some embodiments, the encoded polypeptide contains fewer than 50 consecutive amino acids from amino acids from the NgR CTS domain. While the polypeptide may include a functional GPI domain, a functional GPI domain may be absent, e.g., when a soluble polypeptide is desired. The invention also includes a nucleic acid encoding a NgR-derived polypeptide; a vector, e.g., operably linked to an expression control sequence, containing the nucleic acid; and a transformed host cell containing the vector. The invention also includes a method of producing a NgR-derived polypeptide. The method includes introducing a nucleic acid encoding the above-described polypeptide into a host cell, culturing the host cell under conditions suitable for expression of said polypeptide, and recovering the polypeptide.

The invention also includes an antibody that binds to an epitope in the CTS domain of NgR. The antibody can be polyclonal or monoclonal.

The invention also includes a method of inhibiting binding of a Nogo polypeptide to a NgR. The method includes contacting the Nogo polypeptide with an effective amount of the above-described NgR-derived polypeptide.

The invention also includes a method of inhibiting binding of a Nogo polypeptide to a NgR, comprising contacting the NgR with an antibody that binds to the amino acid sequence consisting of SEQ ID NO:2 (NgR polypeptide).

The invention also includes a method of decreasing inhibition of axonal growth by a CNS neuron. The method includes contacting the neuron with an effective amount of: (a) an above-described NgR-derived polypeptide; or (b) an antibody that binds to the amino acid sequence set forth as SEQ ID NO:2 (NgR). In some embodiments of the invention, the antibody binds to an epitope within the amino acid sequence consisting of amino acids 310–445 of SEQ ID NO:2 (CTS domain of NgR).

The invention also includes a method of treating a central nervous system disease, disorder or injury, e.g., spinal cord injury. The method includes administering to a mammal, e.g., a human, an effective amount of: (a) an agent that inhibits binding of a Nogo polypeptide to a NgR; or (b) an agent that inhibits NgR-dependent signal transduction in a central nervous system neuron. Exemplary agents for inhibiting binding of a Nogo polypeptide to a NgR include: (a) an above-described NgR-derived polypeptide; and (b) an antibody that binds to the NgR polypeptide (SEQ ID NO:2). In some embodiments, the antibody binds to an epitope within the CTS domain of NgR (amino acids 310–445 of SEQ ID NO:2).

The invention also includes a method for identifying a molecule that inhibits binding of a Nogo polypeptide to a NgR. The method includes: (a) providing a NgR polypeptide; (b) contacting the NgR polypeptide with a candidate molecule; and (c) detecting a decrease in binding of the Nogo polypeptide to the NgR in the presence of the candidate molecule, as compared to the binding of the Nogo polypeptide to the NgR in the presence of the candidate molecule.

The method also includes pharmaceutical compositions. In some embodiments the composition contains an above-described NgR-derived polypeptide and a pharmaceutically acceptable carrier. In other embodiments, the composition contains an antibody that binds to an epitope in the NgR CTS domain, and a pharmaceutically acceptable carrier.

The invention also includes a polypeptide that contains the amino acid sequence IYKGVIQAI or EELV, or both, with the polypeptide containing a total of 40 amino acids or fewer ("Nogo ligand-derived polypeptide"). In some embodiments, the Nogo ligand-derived polypeptide includes amino acid residues 2 to 34 of SEQ ID NO:21. In some embodiments, the Nogo ligand-derived polypeptide includes a heterologous amino acid sequence not present in NogoA, wherein the heterologous amino acid sequence contains at least five amino acid residues. The invention also includes a nucleic acid encoding a Nogo ligand-derived polypeptide; a vector, e.g., operably linked to an expression control sequence, containing the nucleic acid; and a transformed host cell containing the vector.

The invention also includes an antibody that binds to an above-described Nogo ligand-derived polypeptide. The antibody can be polyclonal or monoclonal. The invention also includes a composition that contains an above-described NgR-derived polypeptide and a pharmaceutically acceptable carrier or an antibody that binds to an epitope in the NgR CTS domain, and a pharmaceutically acceptable carrier.

The invention also includes an alternative method of inhibiting binding of a Nogo polypeptide to a NgR. The alternative method includes contacting the Nogo polypeptide with an effective amount of an above-described Nogo ligand-derived polypeptide.

The invention also includes an alternative method of decreasing inhibition of axonal growth by a CNS neuron. The alternative method includes contacting the neuron with an effective amount of an above-described Nogo ligand-derived polypeptide.

The invention also includes an alternative method of treating a central nervous system disease, disorder or injury, e.g., a spinal cord injury. The alternative method includes administering to a mammal, e.g., a human, an effective amount of an above-described Nogo ligand-derived polypeptide.

The invention also includes a method of identifying a molecule that decreases Nogo-dependent inhibition of axonal growth. The method includes: (a) providing a polypeptide containing a target sequence consisting of IYKGVIQAI or EELV, or both; (b) contacting the polypeptide with a candidate molecule; and (c) detecting binding of the candidate molecule to a target sequence in the polypeptide.

The invention also includes embodiments wherein SEQ ID NO:4 (murine NgR) is substituted for SEQ ID NO:2 (human NgR). Those of skill in the art will recognize where the human sequence is preferable over the murine sequence and visa versa.

(a) is a graph displaying the results of chick E12 dorsal root ganglion growth cone collapse assays. These assays were performed and quantified as in GrandPré et al., (2000) Nature 403, 439–444. Assays were conducted with no addition (Control), 15 nM GST-Nogo or 15 nM GST-Nogo plus 1 µM Pep2-41 (Nogo+Pep). The values are means±s.e.m. calculated from four determinations. (b) is a graph displaying the results of binding experiments where binding of 10 nM AP-Nogo to chick E12 dorsal root ganglion neurons was measured as described in FIG. 4 with the addition of the indicated concentrations of Pep2-41.

Figure 4A:
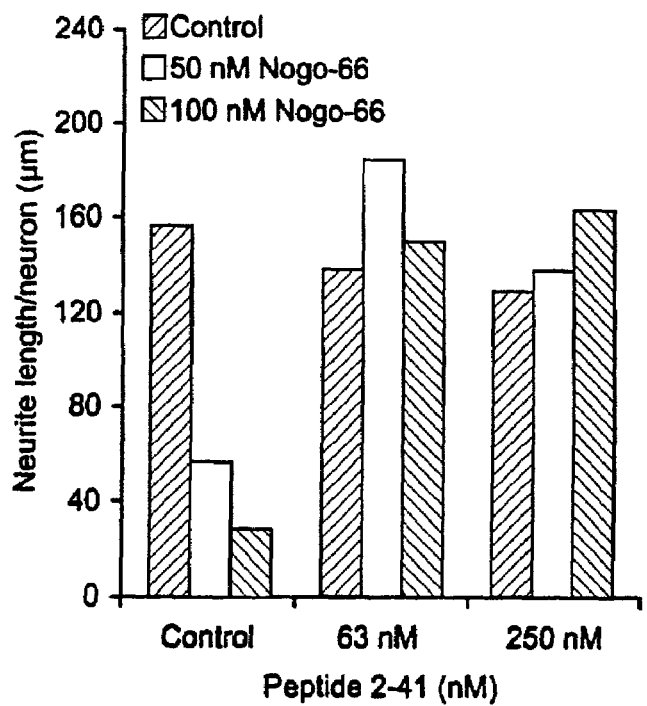
Figure 4B:
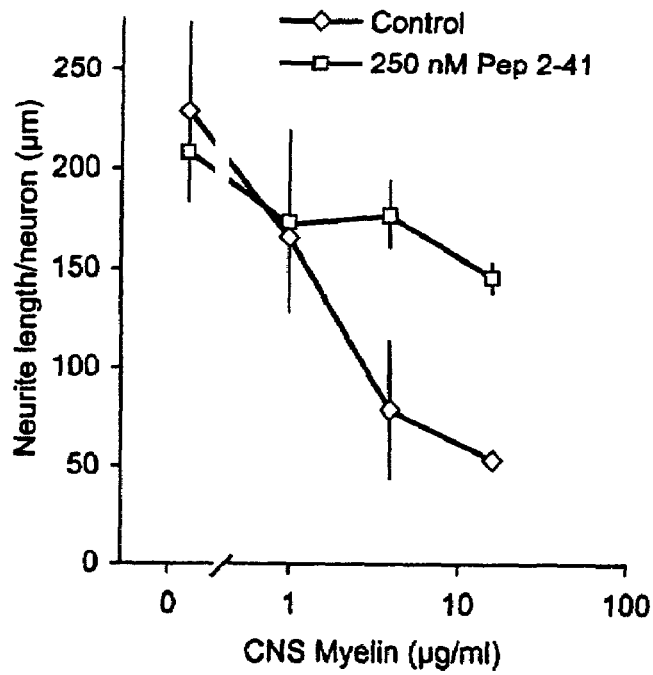

FIG. 4—Nogo Pep2-41 prevents both Nogo & CNS myelin inhibition of neurite outgrowth This figure is a graph which displays the results of outgrowth assays where neurons were cultured in the presence of the indicated concentrations of Pep2-41, purified GST-Nogo (GST-Nogo-66) protein and crude CNS myelin protein. Chick E13 dorsal root ganglion neurons were cultured under standard conditions. For outgrowth assays, neurons were cultured in the presence of the indicated concentrations of Pep2-41, purified GST-Nogo (GST-Nogo-66) protein and crude CNS myelin protein. This demonstrates that Pep2-41 can reverse the inhibition of neurite outgrowth by either GST-Nogo or total CNS myelin.

FIG. 5—Ligand binding assay for axonal Nogo receptors (a) is a photograph of a gel and an immunoblot where the His-AP-Nogo (66 amino acid) protein was expressed in HEK293T cells, and purified from conditioned medium on a Nickel-containing resin via the His tag. Purified protein was subjected to SDS-PAGE and stained for total protein with CBB or immunoblotted with anti-Nogo antibodies (anti-Nogo). Molecular weight markers of 200, 116, 97, 65 and 45 kDa are shown at left, and the migration of AP-Nogo at right. (b) is a photograph of dissociated chick E12 dorsal root ganglion neurons that were incubated with 10 nM AP-Nogo or 10 nM AP-Nogo+160 nM GST-Nogo for sixty minutes at 23° C. The cells were washed, fixed and incubated at 60° C. in order to inactivate endogenous AP. Bound AP-Nogo was detected by incubation with nitro blue tetrazolium. Note the intense neuronal staining by AP-Nogo that is displaced by unlabeled ligand. (c) is a graph displaying experimental data where the potency of AP-Nogo and GST-Nogo in E12 chick dorsal root ganglion growth cone collapse assays was assessed as described in the Example section. The $EC_{50}$ of AP-Nogo was determined to be 1 nM or less. The means±s.e.m. calculated from five to eight determinations are illustrated. (d) is a graph displaying experimental data where the binding of 10 nM AP-Nogo to chick E12 dorsal root ganglion neurons was assessed alone, or in the presence of 100 nM GST-Nogo or in the presence of 4 μM Pep2, which was quantified from experiments as in (b) by the method described in the Example section. The means±s.e.m. calculated from eight determinations are shown. (e) is a graph displaying experimental data where AP-Nogo binding to dorsal root ganglion neurons was measured as a function of AP-Nogo concentration. This is one of six experiments with similar results. (f) is a graph summarizing the data from (e) replotted for Scatchard analysis. The apparent $K_d$ for AP-Nogo binding to E12 chick dorsal root ganglion neurons is 3 nM.

Figure 6:
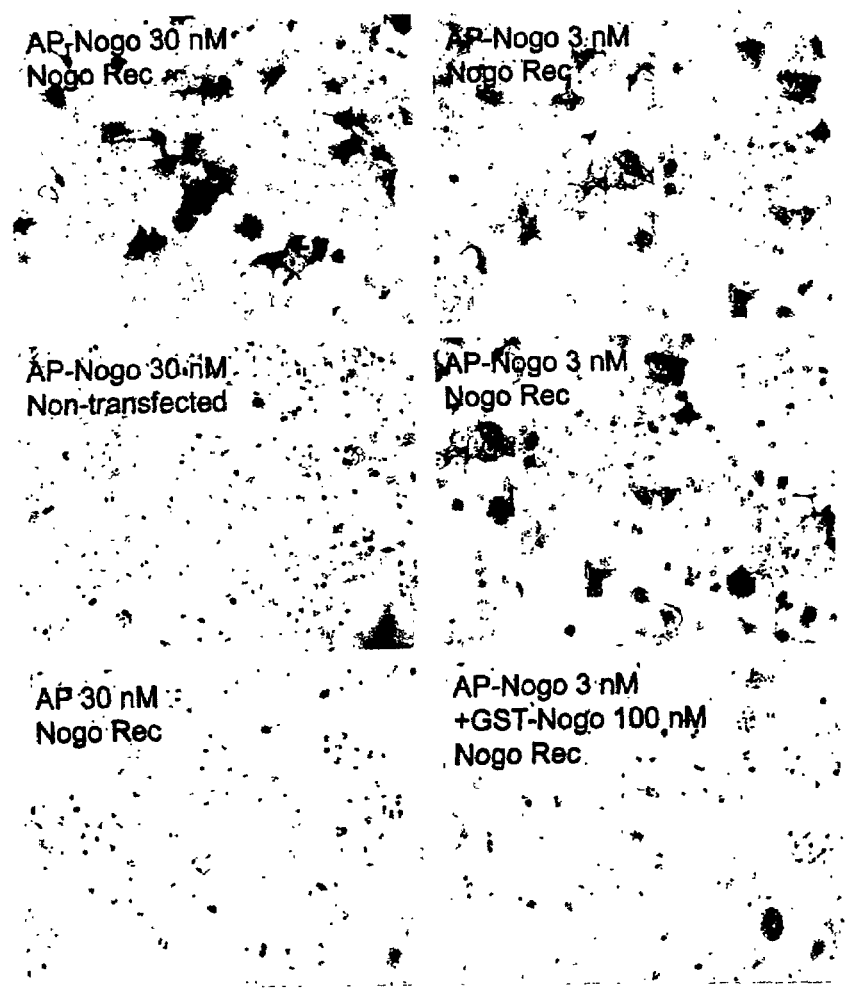

FIG. 6—Nogo binding to COS-7 expressing the Nogo receptor

This figure is a photograph of COS-7 cells that were transfected with an expression vector encoding the murine NgR. Two days after transfection, binding of AP-Nogo or AP was assessed as described in the Example section for dorsal root ganglion neurons. Note the selective binding of AP-Nogo to NgR expressing cells. Binding is greatly reduced in the presence of excess Nogo peptide not fused to AP.

Figure 7:
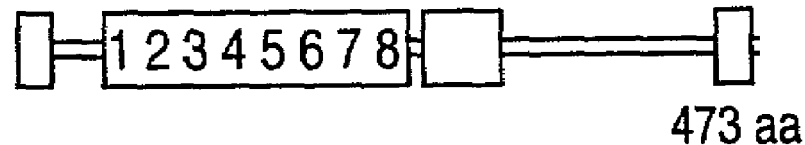

FIG. 7—Structure of the Nogo receptor

This schematic diagram illustrates the major structural features of the NgR.

FIG. 8—Distribution of NgR mRNA.

This figure is a photograph of Northern blot of NgR mRNA for polyA+ RNA samples from the indicated murine tissues on the left and for total RNA samples from various rat brain regions on the right. The migration of RNA size markers is shown at left.

FIG. 9—Nogo-66 Receptor Immunohistology (a) is a photograph of an immunoblot where membrane fractions (10 μg protein) from the indicated cells or chick tissues were analyzed by anti-Nogo-66 receptor immunoblot (molecular weight markers in kDa are at right). (b) is a photograph of COS-7 cells expressing Myc-Nogo-66 receptor or chick E5 spinal cord explants (eight days in vitro) stained with anti-Nogo-66 receptor, anti-Myc or the oligodendrocyte-specific O4 antibody. The bottom three panels show double label immunohistochemistry of the same field (scale bar, 40 μm for the top three panels and 80 μm for the bottom three panels). (c) is a photograph of paraformaldehyde-fixed vibratome sections of adult brain or spinal cord stained with the anti-Nogo-66 receptor preparation. This demonstrates staining of axonal profiles (arrows) in both the pons and spinal cord. Staining is dramatically reduced in the presence of 10 μg/ml GST-Nogo-66 receptor antigen.

FIG. 10—Nogo-66 Receptor mediates growth cone collapse by Nogo-66

(a) is a schematic diagram of different Nogo-66 receptor deletion mutants. These mutants were assessed for level of expression by immunoblot and for AP-Nogo binding. Note that the leucine rich repeats and the leucine rich repeat carboxy terminal are required for Nogo binding but the remainder of the protein is not. The second protein was tested after purification and immobilization. (b) is a diagram of the predicted three dimensional structure for the first seven leucine rich repeats of the Nogo-66 receptor. This is derived from computer modeling based on the predicted structure of the related leucine rich repeats of the leutropin receptor (Jiang et al., (1995) Structure 3, 1341–1353). Modeling is performed by Swiss-Model at The Expert Protein Analysis System (ExPASy) proteomics server of the Swiss Institute of Bioinformatics (SIB) (www.expasy.ch/spdbv). Those regions with beta sheet and alpha helix secondary structure are also indicated.

Figure 11B:
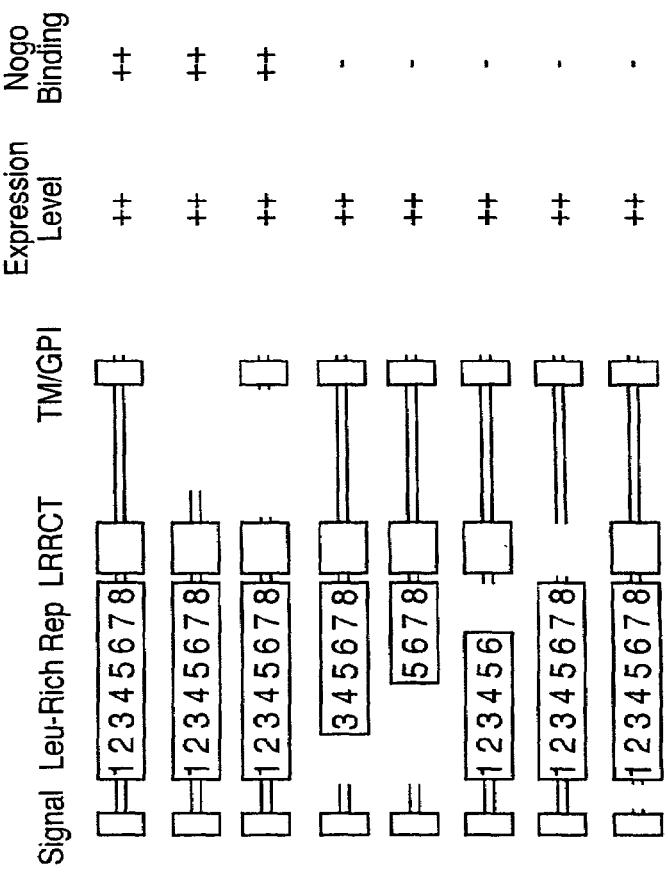
Figure 11A:

FIG. 11—Structure-function analysis of Nogo-66 receptor (a) is a schematic diagram of different Nogo-66 receptor deletion mutants. These mutants were assessed for level of expression by immunoblot and for AP-Nogo binding. Note that the leucine rich repeats and the leucine rich repeat carboxy terminal are required for Nogo binding but the remainder of the protein is not. The second protein was tested after purification and immobilization. (b) is a diagram of the predicted three dimensional structure for the first seven leucine rich repeats of the Nogo-66 receptor. This is derived from computer modeling based on the predicted structure of the related leucine rich repeats of the leutropin receptor (Jiang et al., (1995) Structure 3, 1341–1353). Modeling is performed by Swiss-Model at www.expasy.ch/spdbv. Those regions with beta sheet and alpha helix secondary structure are also indicated.

Figure 12A:
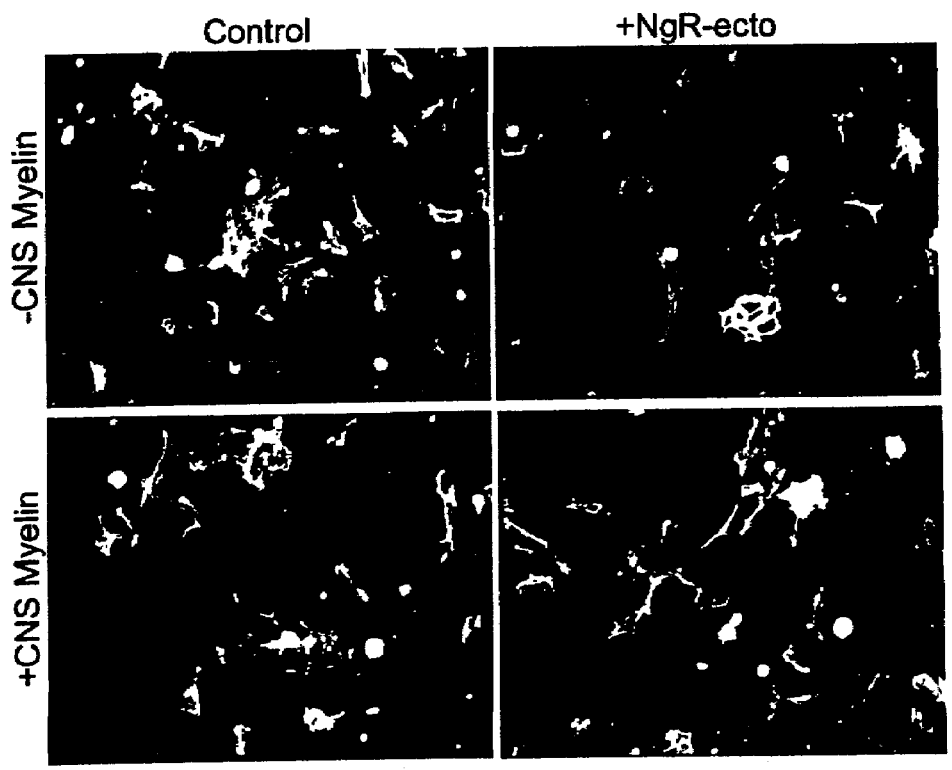

FIG. 12—Soluble NgR blocks Nogo-66

Chick E13 DRG neurons cultured under standard conditions. In growth cone collapse assays, conditioned medium from HEK 293T cells secreting the 1–348 amino acid ectodomain fragment of the murine NgR or control conditioned medium was added together with 100 nM Nogo-66. In the bottom left panel, the data in the graph demonstrates that Nogo-induced collapse is blocked by the soluble receptor fragment. For outgrowth assays, neurons were cultured in the presence of control or NgR ectodomain conditioned medium together with Nogo-66 protein (50 nM) or central nervous system myelin (15 μg total protein/ml). The top four panels show photographs demonstrating that central nervous system myelin inhibits outgrowth and that this is blocked by the presence the NgR ectodomain protein. Outgrowth is quantitated in the graph in the bottom right panel.

Figure 13:
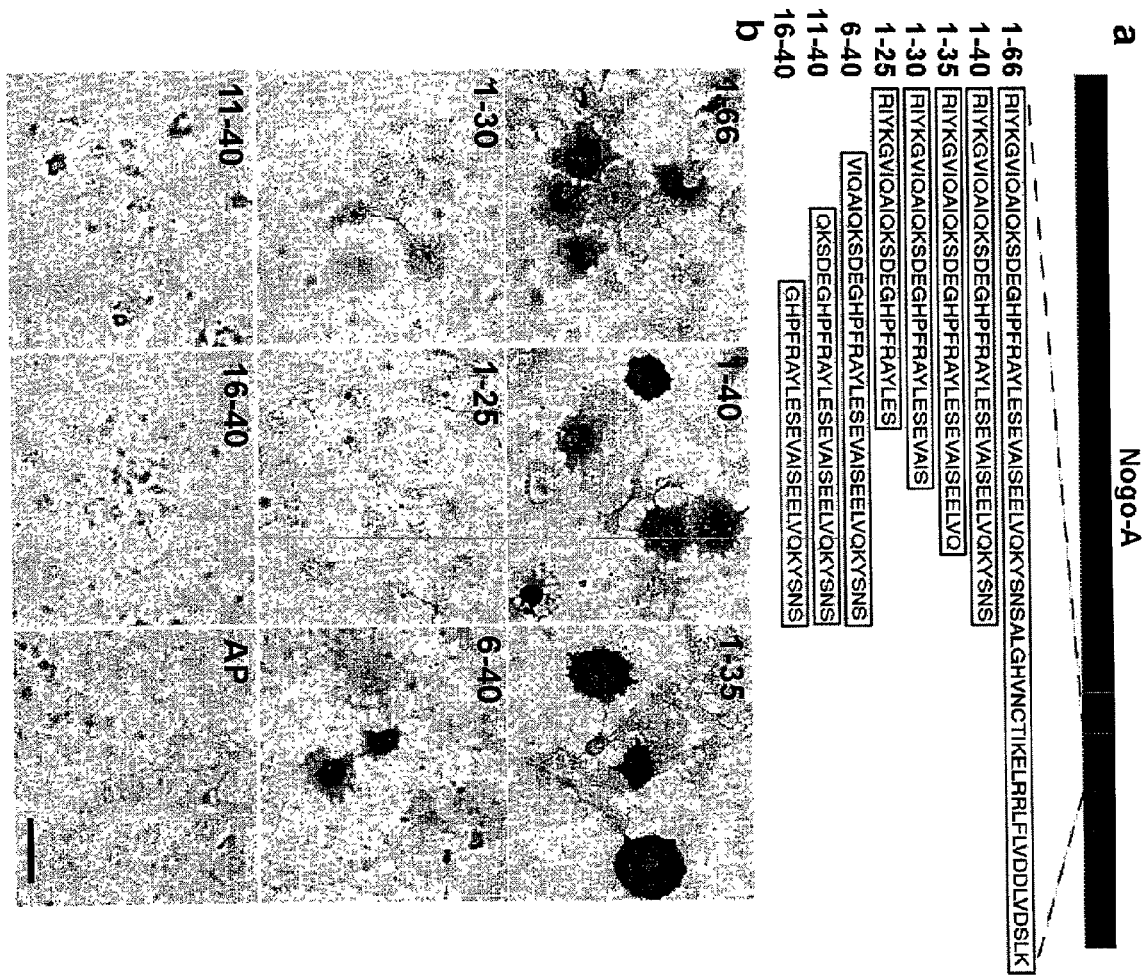

FIG. 13—Regions in the luminal/extracellular domain of Nogo necessary for NgR binding (a) graphically depicts the amino acid sequences of peptides derived from the luminal/extracelluar domain of Nogo that were recombinantly attached to DNA encoding alkaline phosphatase (AP) and expressed to make AP fusion proteins. (b) shows the binding of the above AP fusion proteins to COS-7 cells expressing NgR. Conditioned medium from 293T cells expressing the AP fusion proteins or AP alone was applied to COS-7 cells transfected with mouse NgR (mNgR). Binding was visualized after application of substrates NBT and BCIP. Scale bar, 100 um.

Figure 14:
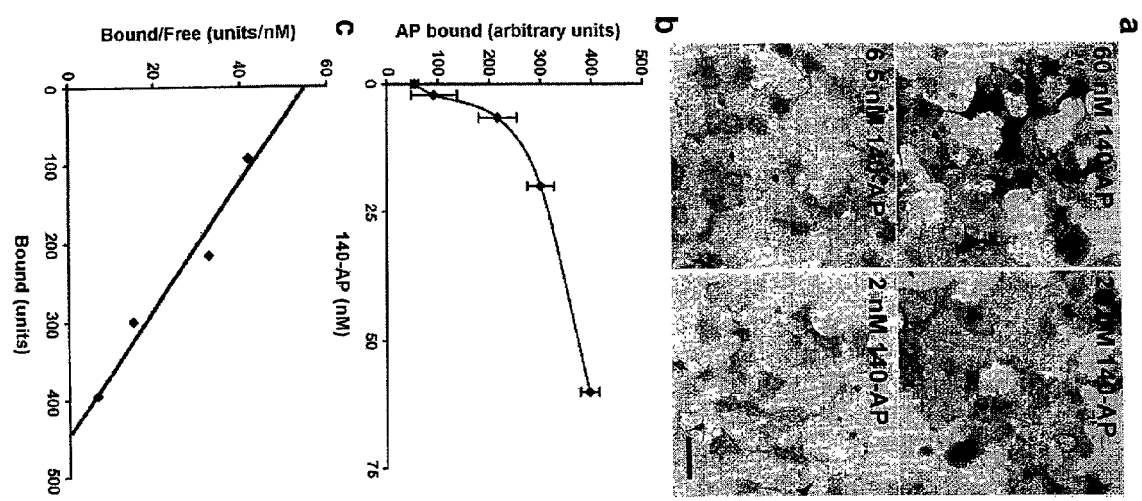

FIG. 14—Residues 1–40 of the luminal/extracellular domain of Nogo bind NgR (a) shows the binding of the fusion protein containing AP and the 1-40 peptide described in FIG. 5a [hereinafter "140-AP"] to COS-7 cells expressing mouse NgR. Scale bar, 100 um. (b) graphically depicts the binding of 140-AP to COS-7 cells expressing mNgR as measured as a function of 140-AP concentration. (c) graphically depicts data derived from the above 140-AP binding assay replotted as bound/free v. bound. The Kd of 140-AP binding to mNgR in this assay is 8 nM.

Figure 15:
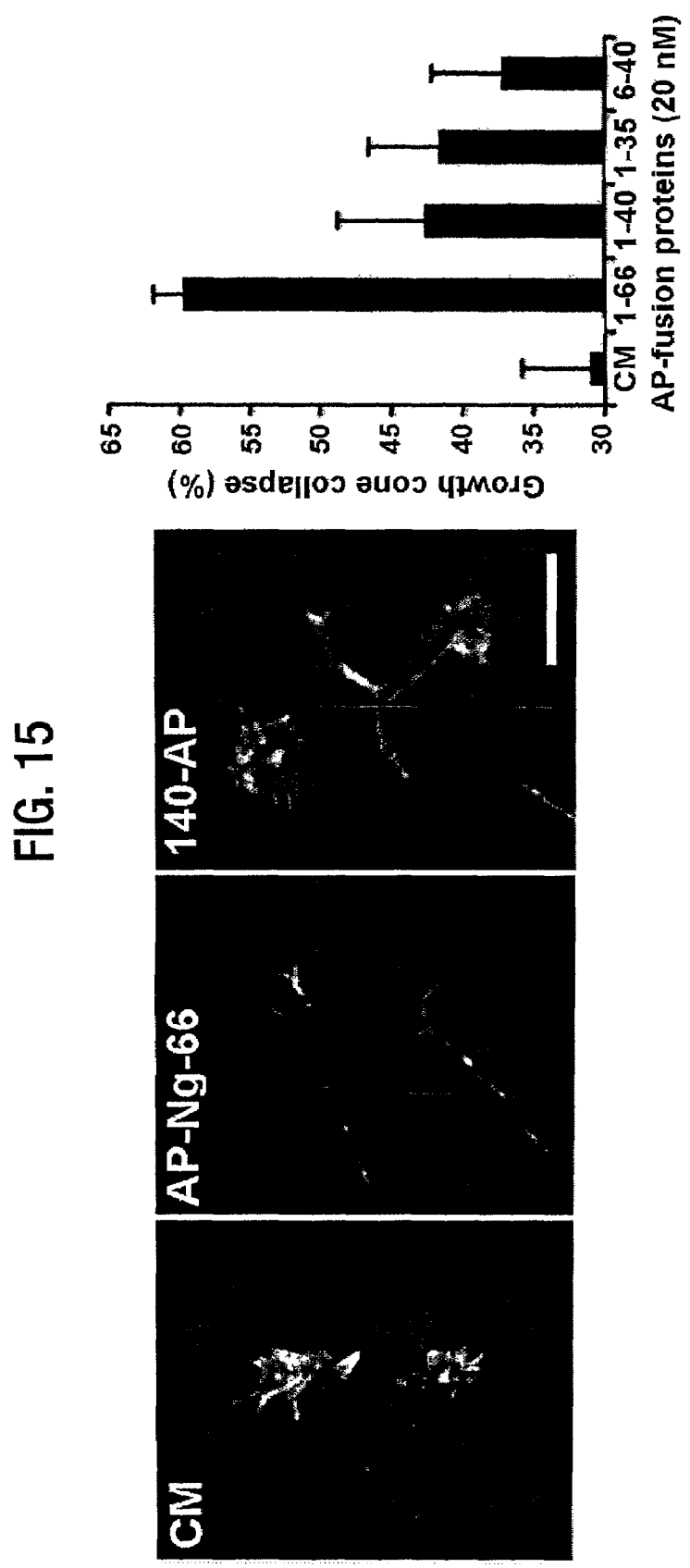

FIG. 15—Growth cone collapsing activity AP-fused peptides (a) shows E12 chick DRG growth cone morphology following 30 minute exposure to 140-AP and AP-Nogo-66 fusion proteins. Scale bar, 25 um. (b) graphically depicts the quantification of growth cone collapse in E12 chick DRG cultures after exposure to condition medium containing 20 nM AP fusion proteins comprising AP fused to the following peptides as described in FIG. 13a: 1-66, 1-40, 1-35 and 6-40. As a control, condition medium containing no AP fusion protein was used.

Figure 16:
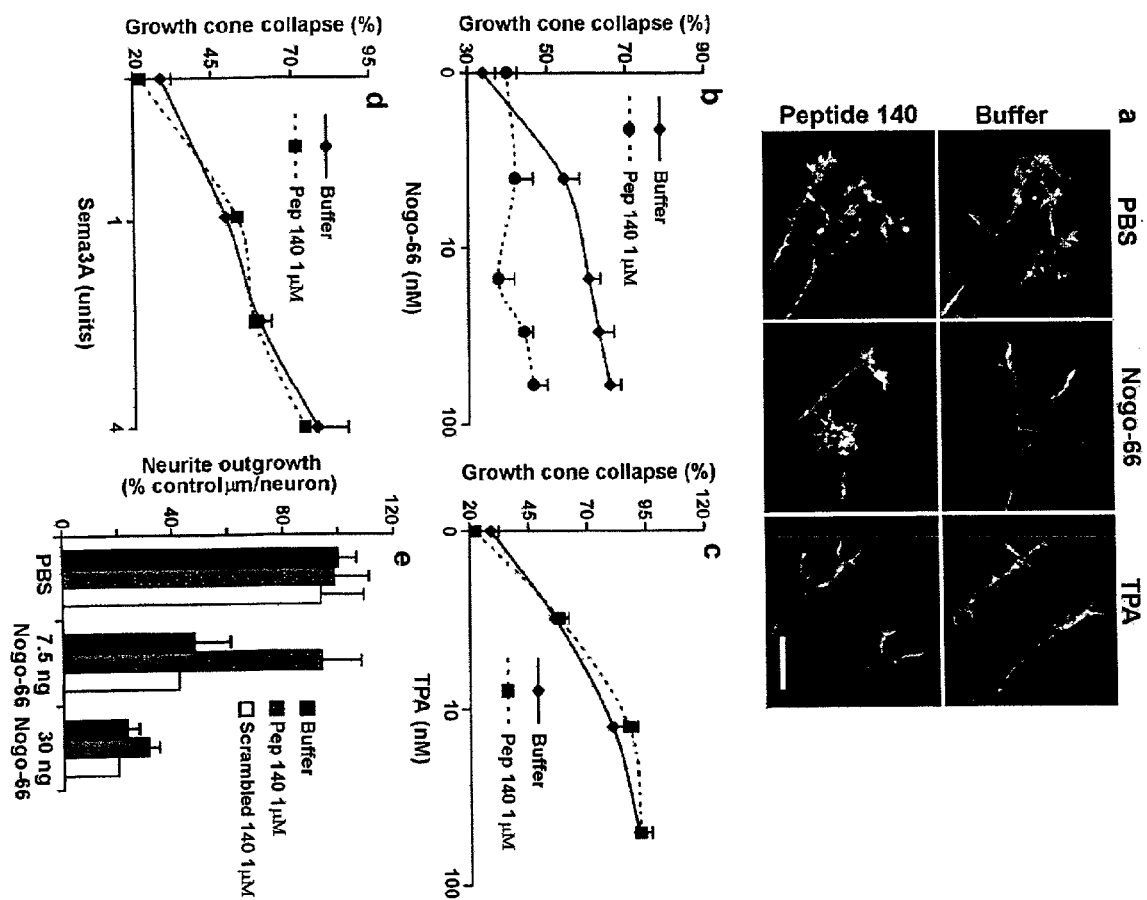

FIG. 16—Peptide 140 neutralizes Nogo-66 inhibitory activity (a) shows E12 chick DRG growth cone morphology after treatment with a synthetic peptide encoding amino acids #1055–1094, acetylated at the C-terminus and amidated at the N-terminus of the human NogoA protein [hereinafter, "peptide 140"], the luminal/extracellular space encoded by SEQ ID NO:22. The cultures were pretreated with 1 uM peptide 140 or buffer followed by a 30 minute exposure to 30 nM GST-Nogo-66 or 12.5 nM TPA. The amino acid sequence of peptide 140 corresponds to a sequence within the luminal/extracellular region of the hNogo protein. Scale bar 25 um. Growth cones were visualized by rhodamine-phalloidin staining. (b)–(d) graphically depicts the amount of E12 chick DRG growth cone collapse after the cells have been pretreated with 1 uM peptide 140, or buffer before a 30 minute exposure to various concentrations of GST-Nogo-66, TPA or Sema3A. (e) graphically depicts, as compared to a control, the percentage of neurite outgrowth in dissociated E12 chick DRG cultures grown for 5–7 hours in the presence of substrate coated with GST-Nogo-66 or phosphate buffered saline (PBS) following treatment with peptide 140, a scrambled version of peptide 140 (i.e., acetyl-SYVKEYAPI-FAGKSRGEIKYQSIEIHEAQVRSDELVQSLN-amide) or buffer.

Figure 17:
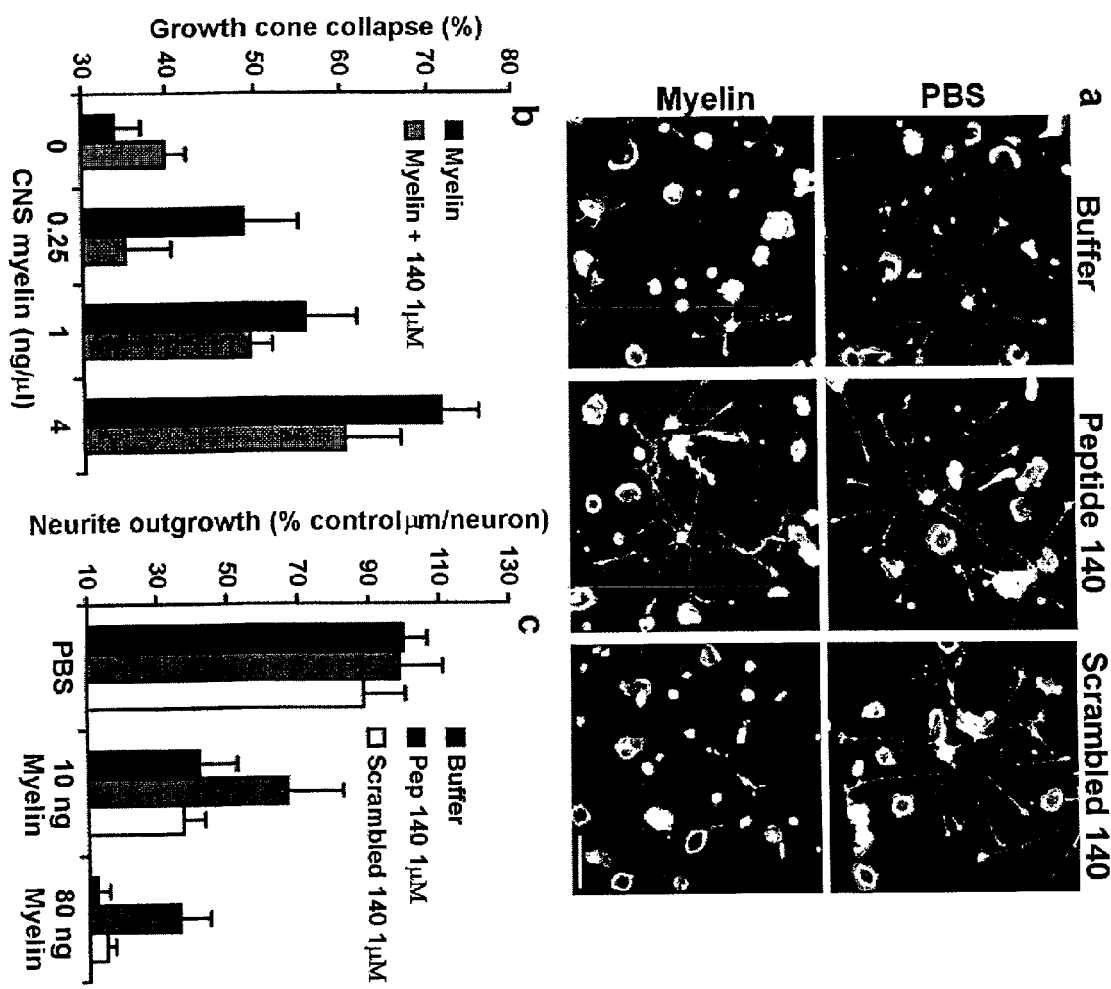

FIG. 17—Peptide 140 paritally blocks CNS myelin inhibitory activity (a) shows dissociated E12 chick DRG cultures grown on bound substrate coating (CNS myelin or PBS) following treatment with 1 uM peptide 140, a scrambled version of peptide 140 or buffer. Scale bar 75 um. (b) graphically depicts the percentage of E12 chick DRG growth cone collapse in explant cultures pretreated with peptide 140 or buffer and then exposed to CNS myelin or PBS for 30 minutes before fixation. (c) graphically depicts the percentage of neurite outgrowth for E12 chick dissociated DRG neurite outgrowth grown for 5–7 hours on bound substrate coating (CNS myelin or PBS) following application of peptide 140, scrambled peptide 140 or buffer.

Figure 18:
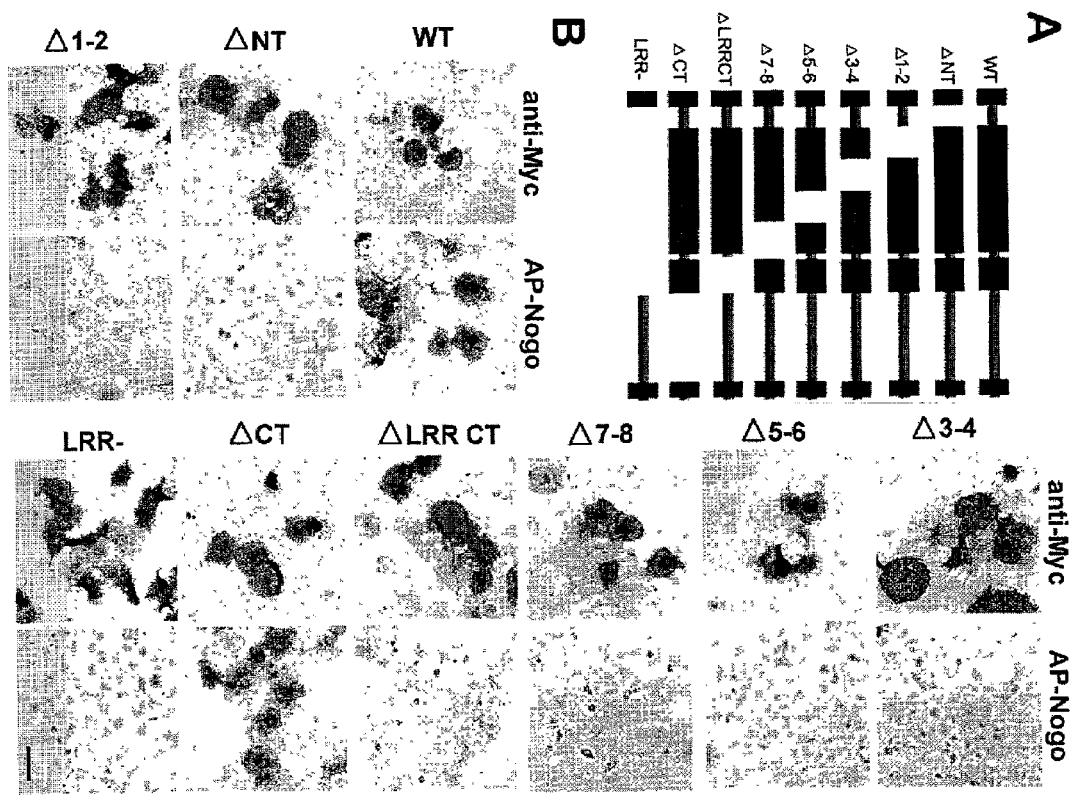

FIG. 18. Nogo binding to NgR Deletion Mutants: LRRNT LRR1-8 and LRRCT required for binding (A) WTNGR (wt) and the NgR deletion mutants used in this study are illustrated. NgR mutants include deletions to the amino terminus (ΔNT), LRR domains 1 and 2 (Δ1–2), LRR domains 3 and 4 (Δ3–4), LRR domains 5 and 6 (Δ5–6), LRR domains 7 and 8 (Δ7–8), the LRR carboxy terminus (ΔLRRCT), the NgR carboxy terminus (ΔCT) and the complete LRR domain (LRR-). (B) COS-7 cells transfected with NgR deletion mutant plasmids were stained for anti-myc immunoreactivity or tested for AP-Nogo binding. All NgR mutant proteins were expressed in COS-7 cells as shown by myc immunoreactivity. Only wtNgR and NgRΔCT-transfected COS-7 cells bound to AP-Nogo. Scale bar, 100 μm.

Figure 19:
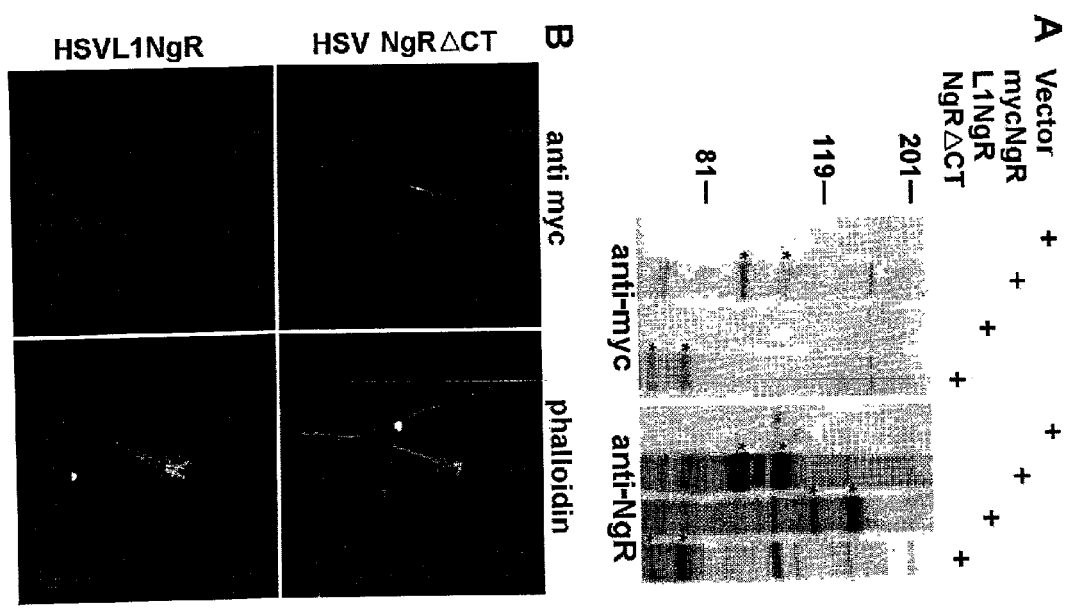

FIG. 19. Expression of HSVNgR proteins in retinal ganglion cell neurites (A) HSV plasmids encoding myc epitope-tagged wild-type NgR (mycNgR), L1NgR, and myc-tagged NgRΔCT were transfected into HEK293T cells and protein expression in cell lysates was analyzed by SDS-PAGE and immunoblotting with anti-myc and anti-NgR antibodies. All three proteins were expressed at the predicted molecular weight as demonstrated by anti-NgR immunoblotting. L1NgR encodes residues 1–451 of mouse NgR fused to the transmembrane and cytoplasmic tail of mouse L1, but lacks a myc tag. (B) Anti-myc immunostaining of infected retinal explants demonstrates expression of mycNgRΔCT in RGC neurites double stained with phalloidin. Myc-staining was negative in a phalloidin-stained neurite that was infected with HSVL1NgR.

Figure 20:
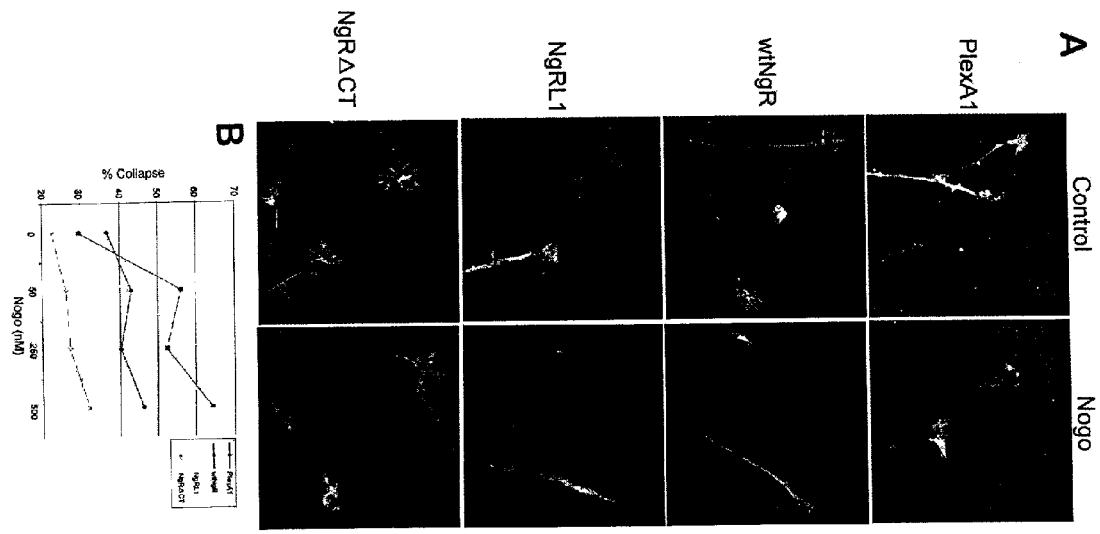

FIG. 20. NgRL1 mediates growth cone collapse in response to GST-hNogo-A(1055–1120) but NgRΔCT does not (A) E7 chick retinal explants were infected with recombinant viral preparations of PlexinA1 (PlexA1), wild-type NgR (wtNgR), NgRL1 chimeric receptor (NgRL1), or NgR carboxy terminal deletion mutant (NgRΔCT). Explants were treated with GST-hNogo-A(1055–1120) for 30 min, and stained with rhodamine-phalloidin. Cells infected with PlexA1 virus or NgRΔCT virus are insensitive to treatment with GST-hNogo-A(1055–1120), whereas wtNgR or NgRL1-infected cells collapse in response to GST-hNogo-A(1055–1120). (B) Dose curve of RGC response to varying amounts of GST-hNogo-A(1055–1120) following infection with NgR viral preparations.

Figure 21:
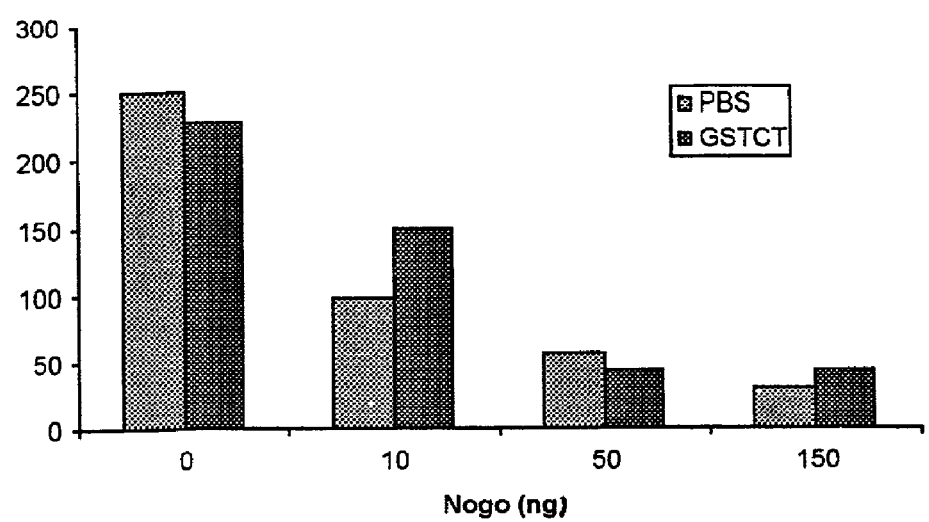

FIG. 21. GSTNgRCT does not constitutively inhibit neurite outgrowth

Neurite outgrowth of dissociated E13 DRGs plated on GST-hNogo-A(1055–1120) substrates in the presence of 100 nM GSTNgRCT or PBS as a control. GSTNgRCT does not inhibit neurite outgrowth on control PBS spots or modify the response of E13 DRGs to GST-hNogo-A(1055–1120) inhibition.

Figure 22:
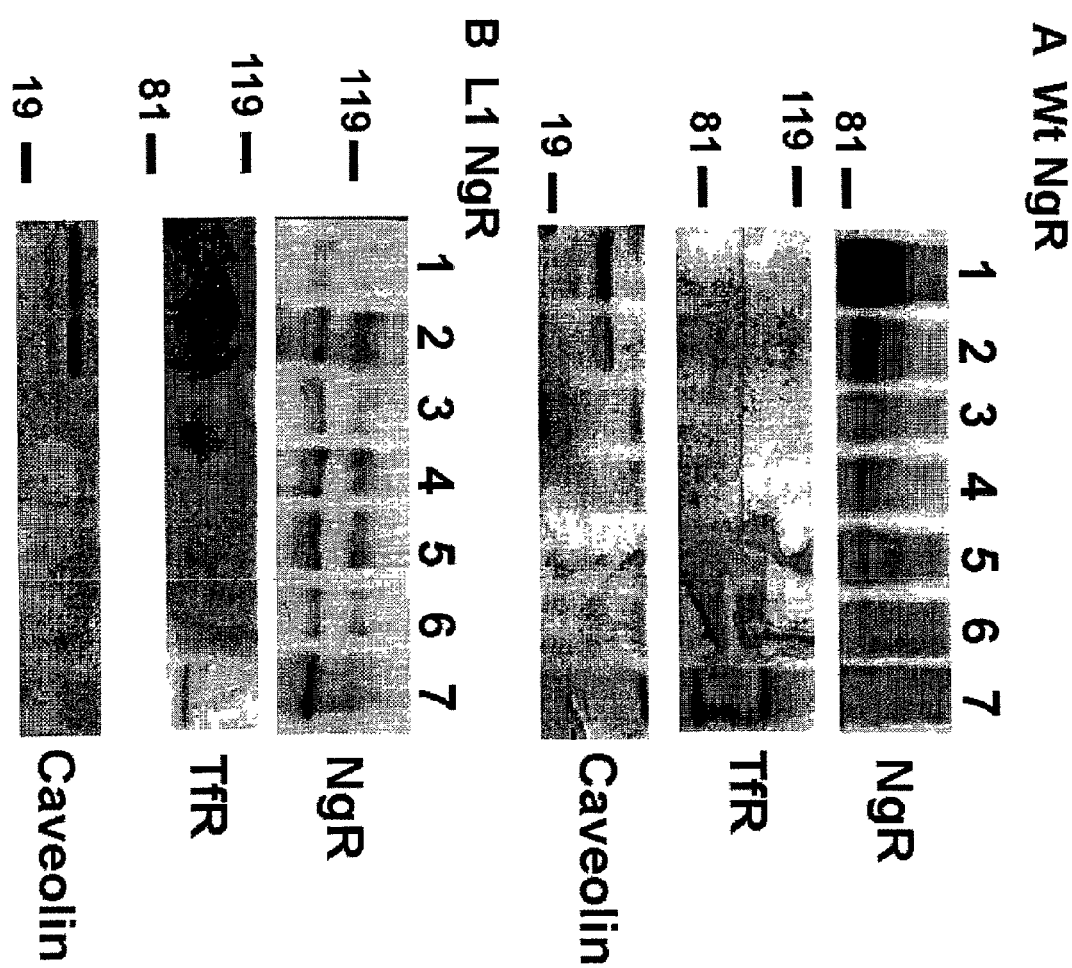

FIG. 22. Analysis of NgR subcellular localization.

Cell lysates from HBEK293T cells transfected with HSVwtNgR or HSVNgRL1 plasmids were fractionated on OptiPrep flotation gradients. Fractions were separated by SDS-PAGE and analyzed by immunoblotting blots with anti-NgR, anti-TfR, or anti-caveolin antibodies. As predicted, wtNgR is found almost exclusively in the caveolin-rich detergent insoluble fraction (A), whereas L1NgR is localized to multiple membrane fractions with a much smaller proportion in the caveolin-rich detergent insoluble fraction compared to wtNgR (B).

Figure 23:
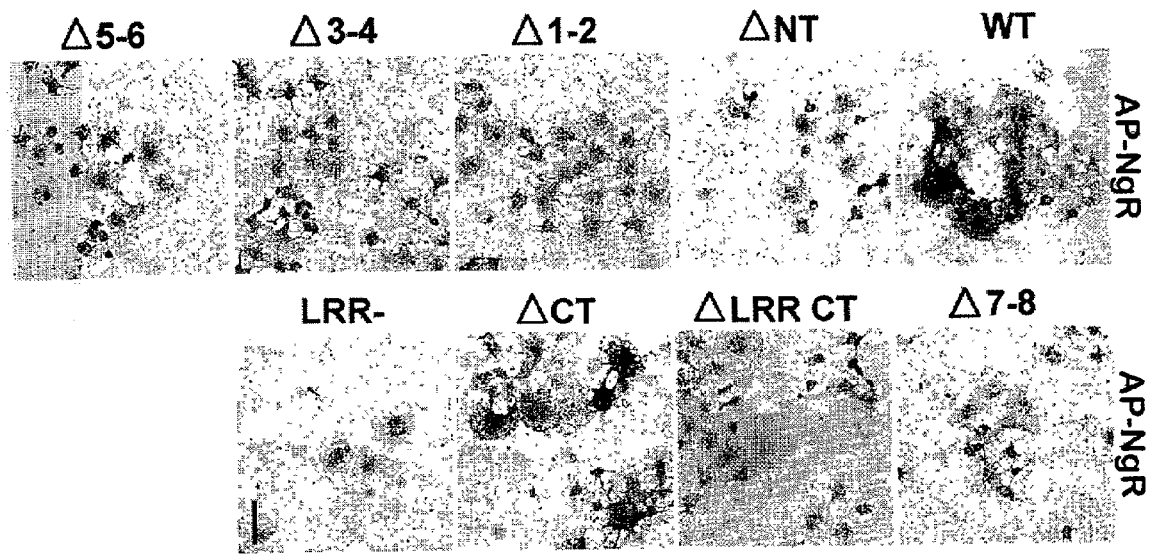

FIG. 23. mNgR binds to mNgR

COS-7 cells were transfected with wtNgR or NgR deletion mutant plasmids and tested for AP-NgR binding. wtNgR and NgRΔCT—transfected COS-7 cells bind to AP-NgR whereas other NgR deletion mutants do not. Scale bar, 100 μm.

Figure 24:
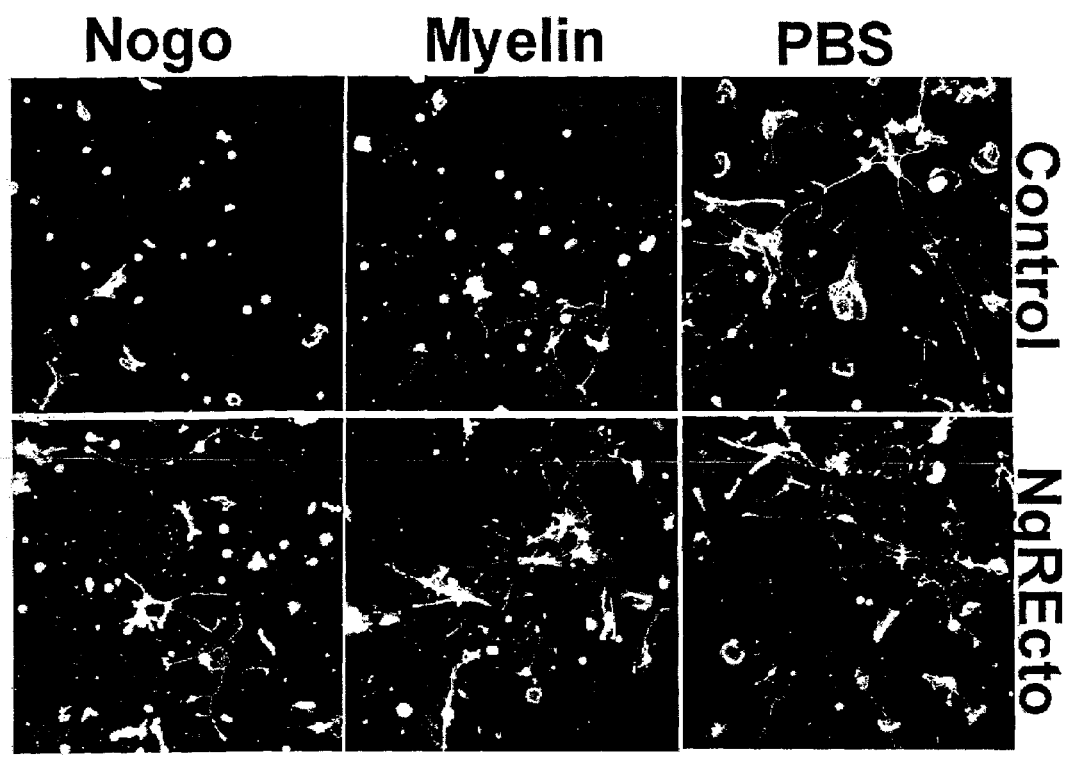

FIG. 24. The soluble ectodomain of mNgR blocks inhibition of outgrowth by soluble hNogo-A(1055–1120) and CNS myelin Chick E13 DRG neurons were cultured under standard conditions. In growth cone collapse assays, conditioned medium from HEK293T cells secreting the 1–348 as ectodomain fragment of the mNgR or control conditioned medium was added together with 100 nM GST-hNogo-A (1055–1120). In the bottom left panel, note that hNogo-A (1055–1120)-induced collapse is blocked by the soluble receptor fragment. For outgrowth assays, neurons were cultured in the presence of control or mNgR ectodomain conditioned medium together with GST-hNogo-A (1055–1120) protein (50 nM) or CNS myelin (15 μg total protein/ml). The top four panels show that CNS myelin inhibits outgrowth and that this is blocked by the presence the mNgR ectodomain protein.

DETAILED DESCRIPTION OF THE INVENTION

I. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, the term "axon" refers to a long cellular protrusion from a neuron, whereby efferent (outgoing) action potentials are conducted from the cell body towards target cells.

As used herein, the term "axonal growth" refers to an extension of the long process or axon, originating at the cell body and preceded by the growth cone.

As used herein, the term "central nervous system disease, disorder or injury" refers to any state associated with abnormal function of the central nervous system (CNS). The term includes, but is not limited to, altered CNS function resulting from physical trauma to cerebral or spinal chord tissue, viral infection, autoimmune mechanism, genetic mutation and neurodegenerative diseases or disorders.

As used herein, the term "chimeric protein" refers to any polypeptide which is not completely homologous at the amino acid level to its wild-type sequence or is encoded by a nucleic acid which is derived from splicing two distinct sources of nucleic acids. The term includes, but is not limited to, fusion proteins and proteins designed to contain one or more amino acid substitutions which distinguishes their amino acid sequence from the wild type sequence.

As used herein, the term "demyelinating disease" refers to a pathological disorder characterized by the degradation of the myelin sheath of the oligodendrocyte cell membrane.

As used herein, the term "neurite" refers to a process growing out of a neuron. As it is sometimes difficult to distinguish a dendrite from an axon in culture, the term neurite is used for both.

As used herein, the term "oligodendrocyte" refers to a neuroglial cell of the CNS whose function is to myelinate CNS axons.

As used herein, the term "polypeptide" refers to a peptide which on hydrolysis yields more than two amino acids, called tripeptides, tetrapeptides, etc. according to the number of amino acids contained in the polypeptide. The term "polypeptide" is used synonomously with the term "protein" and "peptide" throughout the specification.

II. Specific Embodiments

A. NgR Protein and Peptide Agents for the NgR Protein

The present invention provides isolated protein, allelic variants of the protein, and conservative amino acid substitutions of the protein. As used herein, the protein or polypeptide refers to a NgR protein that has the human amino acid sequence depicted in SEQ ID NO: 2 or the murine amino acid sequence depicted in SEQ ID NO: 4. The protein or polypeptide also refers to the peptides identified as NgR peptide agents that have the amino acid sequences depicted in SEQ ID NO: 8, 10, 12, 14, 16, 18 and 20. The invention also includes naturally occurring allelic variants and proteins that have a slightly different amino acid sequence than that specifically recited above. Allelic variants, though possessing a slightly different amino acid sequence than those recited above, will still have the same or similar biological functions associated with the human and murine NgR proteins and the NgR peptide agents depicted in SEQ ID NO: 2, 4, 8, 10, 12, 14, 16, 18 and 20.

As used herein, the family of proteins related to the NgR proteins refers to proteins that have been isolated from organisms in addition to humans and mice. The methods used to identify and isolate other members of the family of proteins related to the NgR proteins are described below.

The NgR proteins and peptide agents of the present invention are preferably in isolated form. As used herein, a protein or ligand is said to be isolated when physical, mechanical or chemical methods are employed to remove the protein from cellular constituents that are normally associated with the protein. A skilled artisan can readily employ standard purification methods to obtain an isolated protein or ligand.

The proteins of the present invention further include conservative variants of the proteins and ligands herein described. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

The allelic variants, the conservative substitution variants, and the members of the protein family, will have an amino acid sequence having at least seventy-five percent amino acid sequence identity with the human and murine sequences set forth in SEQ ID NO: 2, 4, 8, 10, 12, 14, 16, 18 and 20, more preferably at least eighty percent, even more preferably at least ninety percent, and most preferably at least ninety-five percent. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the proteins and peptides of the present invention include molecules comprising the amino acid sequence of SEQ ID NO: 2, 4, 8, 10, 12, 14, 16, 18 and 20; fragments thereof having a consecutive sequence of at least about 3, 4, 5, 6, 10, 15, 20, 25, 30, 35 or more amino acid residues of the NgR proteins and peptide agents; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to rabbit, rat, porcine, bovine, ovine, equine and non-human primate species, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

As described below, members of the family of proteins can be used: (1) to identify agents which modulate at least one activity of the protein, (2) in methods of identifying binding partners for the protein, (3) as an antigen to raise polyclonal or monoclonal antibodies, and 4) as a therapeutic agent.

B. Nucleic Acid Molecules

The present invention further provides nucleic acid molecules that encode the proteins and peptides comprising the amino acid sequence of SEQ ID NO: 2, 4, 8, 10, 12, 14, 16, 18 and 20 and the related proteins herein described, preferably in isolated form. As used herein, "nucleic acid" includes genomic DNA, cDNA, mRNA and antisense molecules, as well as nucleic acids based on alternative backbones or including alternative bases whether derived from natural sources or synthesized.

Homology or identity is determined by BLAST (Basic Local Alignment Search Tool) analysis using the algorithm employed by the programs blastp, blastn, blastx, tblastn and tblastx (Karlin et al., (1990) Proc. Natl. Acad. Sci. USA 87, 2264–2268 and Altschul, (1993) J. Mol. Evol. 36, 290–300, fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases see Altschul et al, (1994) Nature Genetics 6, 119–129 which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89, 10915–10919, fully incorporated by reference). Four blastn parameters were adjusted as follows: Q=10 (gap creation penalty); R=10 (gap extension penalty); wink=1 (generates word hits at every wink$^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

As used herein, "high stringency conditions" means hybridization at 42° C. in the presence of 50% formamide, followed by a first wash at 65° C. with 2×SSC containing 1% sodium SDS, followed by a second wash at 65° C. with 0.1×SSC.

As used herein, a nucleic acid molecule is said to be "isolated" when the nucleic acid molecule is substantially separated from contaminant nucleic acid encoding other polypeptides from the source of nucleic acid.

The present invention further provides fragments of the encoding nucleic acid molecule. As used herein, a fragment of an encoding nucleic acid molecule refers to a portion of the entire protein encoding sequence. The size of the fragment will be determined by the intended use. For example, if the fragment is chosen so as to encode an active portion of the protein, the fragment will need to be large enough to encode the functional region(s) of the protein. If the fragment is to be used as a nucleic acid probe or PCR primer, then the fragment length is chosen so as to obtain a relatively small number of false positives during probing/priming.

Fragments of the encoding nucleic acid molecules of the present invention (i.e., synthetic oligonucleotides) that are used as probes or specific primers for the polymerase chain reaction (PCR) or to synthesize gene sequences encoding proteins of the invention can easily be synthesized by chemical techniques, for example, the phosphotriester method of Matteucci et al., (1981) J. Am. Chem. Soc.103, 3185–3191 or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

Modifications to the primary structure by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

The NgR domain designations used herein are defined as follows:

TABLE 1

Example NgR domains

| Domain | hNgR (SEQ ID: 2) | mNgR (SEQ ID NO: 4) |
|---|---|---|
| Signal Seq. | 1–26 | 1–26 |
| LRRNT | 27–56 | 27–56 |
| LRR1 | 57–81 | 57–81 |
| LRR2 | 82–105 | 82–105 |
| LRR3 | 106–130 | 106–130 |
| LRR4 | 131–154 | 131–154 |
| LRR5 | 155–178 | 155–178 |
| LRR6 | 179–202 | 179–202 |
| LRR7 | 203–226 | 203–226 |
| LRR8 | 227–250 | 227–250 |
| LRRCT | 260–309 | 260–309 |
| CTS (CT Signaling) | 310–445 | 310–445 |
| GPI | 446–473 | 456–473 |

In some embodiments of the invention, the above domains are modified. Modification can be in a manner that preserves domain functionality. Modification can include addition, deletion, or substitution of certain amino acids. Exemplary modifications include conservative amino acid substitutions. Preferably such substitutions number 20 or fewer per 100 residues. More preferably, such substitutions number 10 or fewer per 100 residues. Further exemplary modifications include addition of flanking sequences of up to five amino acids at the N terminus and/or C terminus of one or more domains.

According to this invention, the signal sequence and GPI domains of the NgRs of this invention can be replaced by signal sequences and GPI domains of other proteins. In one embodiment of this invention, the signal sequence domain consists of #1–26 of the hNgR or #1–26 of the niNgR. The GPI domain function have been shown to anchor the proteins to lipid rafts (e.g., Tansey et al., Neuron 25:611–623 (2000)). GPI domains are known in the art, e.g., Gaudiz, et al., J. Biol. Chem. 273(40):26202–26209 (1998). According to one embodiment of the invention, the GPI domain consists of #446–473 amino acid residues of hNgR or #456–473 amino acid residues of mNgR. Biologically active variants of the GPI domain include polypeptides comprising amino acid sequences that anchor proteins to lipid rafts.

The LRRNT domain is a leucine rich repeat domain that is typically flanking the N-terminal side of the LRR1-8 domain.

Leucine rich domains are also known in the art, e.g., Kobe, B. et al., TIBS 19(10):415–421 (1994). In one embodiment of this invention, the LRR1 domain, LRR2 domain, LRR3 domain, LRR4 domain, LRR5 domain, LRR6 domain, the LRR7 domain and the LRR8 domain (collectively, also known as LRR1-8 herein) consists of the amino acid residues as recited in Table 1. The The LR1-8 shares sequence identity with several other leucine rich proteins. According to one embodiment of this invention, a LRR domain of NgR is replaced with a LRR domain of another protein.

The LRRCT domain is a leucine rich repeat domain that is typically flanking the C-terminal side of the LRR1-8 domain.. According to one embodiment of the invention, the LRRCT domain consists of #–260–309 residues of hNgR or mNgR. According to one embodiment of the invention, the LRRCT domain consists of #–260–305 residues of hNgR or mNgR.

A polypeptide comprising a LRRNT domain, a LRR1-8 domain and a LRRCT domain (collectively, also referred to as a NTLRRCT domain (SEQ ID NO:55) herein) of NgR is contemplated. Biologically active variants of NTLRRCT include polypeptides comprising the NTLRRCT domain that can bind Nogo and/or can bind to NgR. According, A CTS domain is an amino acid sequence within a NgR between the LRRCT and the GPI domain. According to one embodiment, the CTS domain can be described by the residues recited above. A CTS domain according to this invention is involved in signalling a neuron in response to a Nogo ligand binding to the NgR. A "portion of a CTS domain" is 20 or more consecutive amino acids of a CTS domain. A portion of a CTS domain can also be selected from the group consisting of 30 or more, 40 or more, and 50 or more consecutive amino acids of a CTS domain. According to one embodiment of this invention, a NgR family member is manipulated so that the CTS region or a portion thereof is deleted, mutated or blocked with another agent so that it is not functional. In one embodiment, the CTS domain consists of #310–445 amino acid residue of hNgR or mNgR, or #306–442 of hNgR (SEQ ID NO:53). According to another embodiment, amino acid sequences that have a sequence identity to #310–445 amino acid residue of hNgR or mNgR, or #306–442 of hNgR in the range of 85% or more, 90% or more, 95% or more, 99% or more sequence identity are contemplated.

C. Isolation of Other Related Nucleic Acid Molecules

As described above, the identification of the human nucleic acid molecule having SEQ ID NO: 1, 3, 7, 9, 11, 13, 15, 17 and 19 allows a skilled artisan to isolate nucleic acid molecules that encode other members of the NgR protein family in addition to the sequences herein described. Further, the presently disclosed nucleic acid molecules allow a skilled artisan to isolate nucleic acid molecules that encode other members of the family of NgR proteins and peptide agents.

Essentially, a skilled artisan can readily use the amino acid sequence of SEQ ID NO: 2, 4, 8, 10, 12, 14, 16, 18 and 20 or an immunogenic fragment thereof to generate antibody probes to screen expression libraries prepared from appropriate cells. Typically, polyclonal antiserum from mammals such as rabbits immunized with the purified protein (as described below) or monoclonal antibodies can be used to probe a mammalian cDNA or genomic expression library, such as lambda gtll library, to obtain the appropriate coding sequence for other members of the protein family. The cloned cDNA sequence can be expressed as a fusion protein, expressed directly using its own control sequences, or expressed by constructions using control sequences appropriate to the particular host used for expression of the enzyme.

Alternatively, a portion of a coding sequence herein described can be synthesized and used as a probe to retrieve DNA encoding a member of the protein family from any mammalian organism. Oligomers containing e.g., approximately 18–20 nucleotides (encoding about a six to seven amino acid stretch) can be prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

D. Recombinant DNA Molecules Containing a Nucleic Acid Molecule

The present invention further provides recombinant DNA molecules (rDNA) that contain a coding sequence. As used herein, a rDNA molecule is a DNA molecule that has been subjected to molecular manipulation. Methods for generating rDNA molecules are well known in the art, for example, see Sambrook et al., (1989) Molecular Cloning—A Laboratory Manual, Cold Spring Harbor Laboratory Press. In the preferred rDNA molecules, a coding DNA sequence is operably linked to expression control sequences and vector sequences.

The choice of vector and expression control sequences to which one of the protein family encoding sequences of the present invention is operably linked depends directly, as is well known in the art, on the functional properties desired (e.g., protein expression, and the host cell to be transformed). A vector of the present invention may be at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Examples of such vector plasmids are pUC8, pUC9, pBR322 and pBR329 (Biorad Laboratories), pPL and pKK223 (Pharmacia). Any suitable prokaryotic host can be used to express a recombinant DNA molecule encoding a protein of the invention.

Expression vectors compatible with eukaryotic cells, preferably those compatible with vertebrate cells, can also be used to form a rDNA molecules that contains a coding sequence. Eukaryotic cell expression vectors are well known in the art and are available from several commercial sources. Typically, such vectors are provided containing convenient restriction sites for insertion of the desired DNA segment. Examples of such vectors are pSVL and pKSV-10 (Pharmacia), pBPV-1, pML2d (International Biotechnologies), pTDT1 (ATCC 31255) and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., (1982) J. Mol. Anal. Genet. 1, 327–341). Alternatively, the selectable marker can be present on a separate plasmid, the two vectors introduced by co-transfection of the host cell, and transfectants selected by culturing in the appropriate drug for the selectable marker.

E. Host Cells Containing an Exogenously Supplied Coding Nucleic Acid Molecule

The present invention further provides host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Examples of useful eukaryotic host cells include Chinese hamster ovary (CHO) cells available from the ATCC as CCL61, NIH Swiss mouse embryo cells NIH-3T3 available from the ATCC as CRL1658, baby hamster kidney cells (BHK), and the like eukaryotic tissue culture cell lines.

Transformation of appropriate cell hosts with a rDNA molecule of the present invention is accomplished by well known methods that typically depend on the type of vector used and host system employed. With regard to transformation of prokaryotic host cells, electroporation and salt treatment methods can be employed (see, for example, Sambrook et al., (1989) Molecular Cloning—A Laboratory Manual, Cold Spring Harbor Laboratory Press; Cohen et al., (1972) Proc. Natl. Acad. Sci. USA 69, 2110–2114). With regard to transformation of vertebrate cells with vectors containing rDNA, electroporation, cationic lipid or salt treatment methods can be employed (see, for example, Graham et al., (1973) Virology 52, 456–467; Wigler et al., (1979) Proc. Natl. Acad. Sci. USA 76, 1373–1376).

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, (1975) J. Mol. Biol. 98, 503–517 or the proteins produced from the cell assayed via an immunological method.

F. Production of Recombinant Proteins using a rDNA Molecule

The present invention further provides methods for producing a protein of the invention using nucleic acid molecules herein described. In general terms, the production of a recombinant form of a protein typically involves the following steps:

First, a nucleic acid molecule is obtained that encodes a protein of the invention, such as the nucleic acid molecule depicted in SEQ ID NO: 1, 3, 7, 9, 11, 13, 15, 17 and 19 or nucleotides 166–1584 of SEQ ID NO: 1 and nucleotides 178–1596 of SEQ ID NO:3. If the encoding sequence is uninterrupted by introns, it is directly suitable for expression in any host.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

G. Methods to Identify Binding Partners

The present invention provides methods for use in isolating and identifying binding partners of proteins of the invention. In some embodiments, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner bound to the protein of the invention can then be removed and further analyzed. To identify and isolate a binding partner, the entire protein, for instance the entire NgR protein of either SEQ ID NO: 2 or 4 or the entire Nogo protein of SEQ ID NO: 6 can be used. Alternatively, a fragment of the protein can be used.

As used herein, a cellular extract refers to a preparation or fraction which is made from a lysed or disrupted cell. The preferred source of cellular extracts will be cells derived from human brain or spinal cord tissue, for instance, human cerebral tissue. Alternatively, cellular extracts may be prepared from any source of neuronal tissue or available neuronal cell lines, particularly olgiodendrocyte derived cell lines.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density-sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide-binding partner pairs from other constituents found in the extract. The identified binding partners can be either a single protein or a complex made up of two or more proteins. Alternatively, binding partners may be identified using the Alkaline Phosphatase fusion assay according to the procedures of Flanagan & Vanderhaeghen, (1998) Annu. Rev. Neurosci. 21, 309–345 or Takahashi et al., (1999) Cell 99, 59–69; the Far-Western assay according to the procedures of Takayama et al., (1997) Methods Mol. Biol. 69, 171–184 or Sauder et al., J. Gen. Virol. (1996) 77, 991–996 or identified through the use of epitope tagged proteins or GST fusion proteins.

Alternatively, the nucleic acid molecules of the invention can be used in a yeast two-hybrid system. The yeast two-hybrid system has been used to identify other protein partner pairs and can readily be adapted to employ the nucleic acid molecules herein described (see Stratagene Hybrizap® two-hybrid system).

H. Methods to Identify Agents that Modulate Activity

The present invention provides methods for identifying agents that modulate at least one activity of a NgR protein. The invention also provides methods for identifying agents that modulate at least one activity of a Nogo protein. Such methods or assays may utilize any means of monitoring or detecting the desired activity.

In one format, the specific activity of a NgR protein or Nogo protein, normalized to a standard unit, between a cell population that has been exposed to the agent to be tested compared to an un-exposed control cell population may be assayed. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes can be prepared by immunizing suitable mammalian hosts utilizing appropriate immunization protocols using the NgR protein, Nogo protein, NgR peptide agents or immunogenic fragments of any of the foregoing. To enhance immunogenicity, these proteins or fragments can be conjugated to suitable carriers. Methods for preparing immunogenic conjugates with carriers such as BSA, KLH or other carrier proteins are well known in the art. In some circumstances, direct conjugation using, for example, carbodiimide reagents may be effective; in other instances linking reagents such as those supplied by Pierce Chemical Co. may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using standard methods, see e.g., Kohler & Mistein, (1992) Biotechnology 24, 524–526 or modifications which effect immortalization of lymphocytes or spleen cells, as is generally known. The immortalized cell lines secreting the desired antibodies can be screened by immunoassay in which the antigen is the peptide hapten, polypeptide or protein. When the appropriate immortalized cell culture secreting the desired antibody is identified, the cells can be cultured either in vitro or by production in ascites fluid.

The desired monoclonal antibodies may be recovered from the culture supernatant or from the ascites supernatant. The intact anti-Nogo or anti-NgR antibodies or fragments thereof can be used as e.g., antagonists of binding between Nogo (ligand) and a NgR. Use of immunologically reactive fragments, such as the Fab, Fab' of F(ab')$_2$ fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin, for instance, humanized antibodies.

The antibody can therefore be a humanized antibody or human a antibody, see. e.g., in U.S. Pat. No. 5,585,089 or Riechmann et al., (1988) Nature 332, 323–327.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a non-random basis which takes into account the sequence of the target site or its conformation in connection with the agent's action. Agents can be rationally selected or rationally designed by utilizing the peptide sequences that make up these sites. For example, a rationally selected peptide agent can be a peptide whose amino acid sequence is identical to the binding domain (SEQ ID NO: 20) of Nogo which interacts with the NgR. Alternatively, it can be a fragment of the binding domain, e.g., SEQ ID NO: 8, 10, 12, 14, 16 and 18.

The agents of the present invention can be, as examples, peptides, antibodies, antibody fragments, small molecules, vitamin derivatives, as well as carbohydrates. Peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies or fragments thereof that bind to a Nogo protein or NgR protein. Antibody agents can be obtained by immunization of suitable mammalian subjects with peptides, containing as antigenic regions, those portions of the protein intended to be targeted by the antibodies.

I. High Throuphput Assays

The power of high throughput screening is utilized to the search for new compounds which are capable of interacting with the NgR protein. For general information on high-throughput screening (e.g., Devlin, (1998) High Throughput Screening, Marcel Dekker; U.S. Pat. No. 5,763,263). High throughput assays utilize one or more different assay techniques.

Immunodiagnostics and Immunoassays. These are a group of techniques used for the measurement of specific biochemical substances, commonly at low concentrations in complex mixtures such as biological fluids, that depend upon the specificity and high affinity shown by suitably prepared and selected antibodies for their complementary antigens. A substance to be measures must, of necessity, be antigenic-either an immunogenic macromolecule or a haptenic small molecule. To each sample a known, limited amount of specific antibody is added and the fraction of the antigen combining with it, often expressed as the bound:free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including: enzyme-linked immunosorbent assay (ELISA); radioimmuno-assay (RIA); fluorescent immunoassay (FIA); chemiluminescent immunoassay (CLIA); and labeling the antibody with colloidal gold particles (immuNogold).

Common assay formats include the sandwhich assay, competitive or competition assay, latex agglutination assay, homogeneous assay, microtitre plate format and the micro-particle-based assay.

Enzyme-linked immunosorbent assay (LISA). ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to "capture" the relevant antigen (or antibody) in the test solution. The antigen-antibody complex is then detected by measuring the activity of an appropriate enzyme that had previously been covalently attached to the antigen (or antibody).

For information on ELISA techniques, see, for example, Crowther, (1995) ELISA—Theory and Practice (Methods in Molecular Biology), Humana Press; Challacombe & Kemeny, (1998) ELISA and Other Solid Phase Immunoassays—Theoretical and Practical Aspects, John Wiley; Kemeny, (1991) A Practical Guide to ELISA, Pergamon Press; Ishikawa, (1991) Ultrasensitive and Rapid Enzyme Immunoassay (Laboratory Techniques in Biochemistry and Molecular Biology) Elsevier.

Colorimetric Assays for Enzymes. Colorimetry is any method of quantitative chemical analysis in which the concentration or amount of a compound is determined by comparing the color produced by the reaction of a reagent with both standard and test amounts of the compound, e.g., using a colorimeter or a spectrophotometer.

Standard colorimetric assays of beta-galactosidase enzymatic activity are well known to those skilled in the art (see, for example, Norton et al., (1985) Mol. Cell. Biol. 5, 281–290). A colorimetric assay can be performed on whole cell lysates using O-nitrophenyl-beta-D-galactopyranoside (ONPG, Sigma) as the substrate in a standard colorimetric beta-galactosidase assay (Sambrook et al., (1989) Molecular Cloning—A Laboratory Manual, Cold Spring Harbor Laboratory Press. Automated colorimetric assays are also available for the detection of beta-galactosidase activity (see e.g. U.S. Pat. No. 5,733,720).

Immunofluorescence Assays. Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

For general information on immunofluorescent techniques, see, for example, Knapp et al., (1978) Immunofluorescence and Related Staining Techniques, Elsevier; Allan, (1999) Protein Localization by Fluorescent Microscopy—A Practical Approach (The Practical Approach Series) Oxford University Press; Caul, (1993) Immunofluorescence Antigen Detection Techniques in Diagnostic Microbiology, Cambridge University Press. For detailed explanations of immunofluorescent techniques applicable to the present invention, see U.S. Pat. No. 5,912,176; U.S. Pat. No. 5,869,264; U.S. Pat. No. 5,866,319; and U.S. Pat. No. 5,861,259.

J. Uses for Agents that Modulate Activity

As provided in the Examples, the Nogo and NgR proteins and nucleic acids, such as the proteins having the amino acid sequence of SEQ ID NO: 2, 4 or 6, are expressed in myelin derived from axon and dendrites. Agents that modulate or up- or down-regulate the expression of the Nogo or NgR protein or agents such as agonists or antagonists of at least one activity of the Nogo or NgR protein may be used to modulate biological and pathologic processes associated with the protein's function and activity. The invention is particularly useful in the treatment of human subjects.

Pathological processes refer to a category of biological processes which produce a deleterious effect. For example, expression of a protein of the invention may be associated with inhibition of axonal regeneration following cranial, cerebral or spinal trauma, stroke or a demyelinating disease. Such demyelinating diseases include, but are not limited to, multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Merzbacher disease, Spongy degeneration, Alexander's disease, Canavan's disease, metachromatic leukodystrophy and Krabbe's disease. As used herein, an agent is said to modulate a pathological process when the agent reduces the degree or severity of the process. For instance, a demyelinating disease may be prevented or disease progression modulated by the administration of agents which reduce, promote or modulate in some way the expression or at least one activity of a protein of the invention.

In one example, administration of the Nogo peptide agents depicted in SEQ ID NO: 8, 10, 12, 14, 16, 18 and 20 can be used to treat a demyelinating disease associated with Nogo or the NgR protein. In another example, cells which express the peptide agents of the invention may be transplanted to a site spinal cord injury to facilitate axonal growth throughout the injured site. Such transplanted cells would provide a means for restoring spinal cord function following injury or trauma.

In yet another example, administration of soluble NgR protein that binds to Nogo can be used to treat a demyelinating disease associated with Nogo or the NgR protein. This agent can be used to prevent the binding of Nogo to cell bound NgR and act as an antagonist of Nogo. Soluble receptors have been used to bind cytokines or other ligands to regulate their function (Thomson, (1998) Cytokine Handbook, Academic Press). A soluble receptor occurs in solution, or outside of the membrane. Soluble receptors may occur because the segment of the molecule which spans or associates with the membrane is absent. This segment is commonly referred to in the art as the transmembrane domain of the gene, or membrane binding segment of the protein. Thus, in some embodiments of the invention, a soluble receptor includes a fragment or an analog of a membrane bound receptor. Preferably, the fragment contains at least six, e.g., ten, fifteen, twenty, twenty-five, thirty, forty, fifty, sixty, or seventy amino acids, provided it retains its desired activity.

In other embodiments of the invention, the structure of the segment that associates with the membrane is modified (e.g., DNA sequence polymorphism or mutation in the gene) so the receptor is not tethered to the membrane, or the receptor is inserted, but is not retained within the membrane. Thus, a soluble receptor, in contrast to the corresponding membrane bound form, differs in one or more segments of the gene or receptor protein that are important to its association with the membrane.

The agents of the present invention can be provided alone, or in combination, or in sequential combination with other agents that modulate a particular pathological process. For example, an agent of the present invention can be administered in combination with anti-inflammatory agents following stroke as a means for blocking further neuronal damage and inhibition of axonal regeneration. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. For example, an agent may be administered locally to a site of injury via microinfusion. Typical sites include, but are not limited to, damaged areas of the spinal cord resulting from injury or damaged sites in the brain resulting from a stroke. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents which modulate expression or at least one activity of a protein of the invention. While individual needs vary, determination of optimal ranges of effective amounts of each component is within the skill of the art. Typical dosages comprise 1 pg/kg to 100 mg/kg body weight. The preferred dosages for systemic administration comprise 100 ng/kg to 100 mg/kg body weight. The preferred dosages for direct administration to a site via microinfusion comprise 1 ng/kg to 1 μg/kg body weight.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol and dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient. Suitable formulations for oral administration include hard or soft gelatin capsules, pills, tablets, including coated tablets, elixirs, suspensions, syrups or inhalations and controlled release forms thereof.

In practicing the methods of this invention, the agents of this invention may be used alone or in combination, or in combination with other therapeutic or diagnostic agents. In certain preferred embodiments, the compounds of this invention may be co-administered along with other compounds typically prescribed for these conditions according to generally accepted medical practice, such as anti-inflammatory agents, anticoagulants, antithrombotics, including platelet aggregation inhibitors, tissue plasminogen activators, urokinase, prourokinase, streptokinase, aspirin and heparin. The compounds of this invention can be utilized in vivo, ordinarily in mammals, such as humans, sheep, horses, cattle, pigs, dogs, cats, rats and mice, or in vitro.

K. Peptide Mimetics.

This invention also includes peptide mimetics which mimic the three-dimensional structure of Nogo and block Nogo binding at the NgR. Such peptide mimetics may have significant advantages over naturally-occurring peptides, including, for example: more economical production, greater chemical stability, enhanced pharmacological properties (half-life, absorption, potency, efficacy, etc.), altered specificity (e.g., a broad-spectrum of biological activities), reduced antigenicity, and others.

In one form, mimetics are peptide-containing molecules that mimic elements of protein secondary structure. (see, for example, Johnson et al., (1993) Peptide Turn Mimetics, in Biotechnology and Pharmacy, Pezzuto et al., (editors) Chapman and Hall). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

In another form, peptide analogs are commonly used in the pharmaceutical industry as non-peptide drugs with properties analogous to those of the template peptide. These types of non-peptide compounds are also referred to as "peptide mimetics" or "peptidomimetics" (Fauchere, (1986) Adv. Drug Res. 15, 29–69; Veber & Freidinger, (1985) Trends Neurosci. 8, 392–396; Evans et al., (1987) J. Med. Chem. 30, 1229–1239, which are incorporated herein by reference) and are usually developed with the aid of computerized molecular modeling.

Peptide mimetics that are structurally similar to therapeutically useful peptides may be used to produce an equivalent therapeutic or prophylactic effect. Generally, peptide mimetics are structurally similar to a paradigm polypeptide (i.e., a polypeptide that has a biochemical property or pharmacological activity), such as the extracellular domain of Nogo, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$— and —$CH_2SO$—, by methods known in the art and further described in the following references; Weinstein, (1983) Chemistry and Biochemistry of Amino Acids, Peptides and Proteins, Marcel Dekker; Morley, (1980) Trends Pharmacol. Sci. 1, 463–468 (general review); Hudson et al., (1979) Int. J. Pept. Protein Res. 14, 177–185 (—$CH_2NH$—, $CH_2CH_2$—); Spatola et al., (1986) Life Sci. 38, 1243–1249 (—$CH_2$—S); Hann, (1982) J. Chem. Soc. Perkin Trans. 1, 307–314 (—CH—CH—, cis and trans); Almquist et al., (1980) J. Med. Chem. 23, 1392–1398 (—$COCM_2$—); Jennings-White et al., (1982) Tetrahedron Lett. 23, 2533 (—$COCH_2$—); Holladay et al., (1983) Tetrahedron Lett. 24, 4401–4404 (—$C(OH)CH_2$—); and Hruby, (1982) Life Sci. 31, 189–199 (—$CH_2S$—); each of which is incorporated herein by reference.

Labeling of peptide mimetics usually involves covalent attachment of one or more labels, directly or through a spacer (e.g., an amide group), to non-interfering position(s) on the peptide mimetic that are predicted by quantitative structure-activity data and molecular modeling. Such non-interfering positions generally are positions that do not form direct contacts with the macromolecule(s) (e.g., are not contact points in Nogo-NgR complexes) to which the peptide mimetic binds to produce the therapeutic effect. Derivitization (e.g., labeling) of peptide mimetics should not substantially interfere with the desired biological or pharmacological activity of the peptide mimetic.

Nogo peptide mimetics can be constructed by structure-based drug design through replacement of amino acids by organic moieties (see, for example, Hughes, (1980) Philos. Trans. R. Soc. Lond. 290, 387–394; Hodgson, (1991) Biotechnol. 9, 19–21; Suckling, (1991) Sci. Prog. 75, 323–359).

The use of peptide mimetics can be enhanced through the use of combinatorial chemistry to create drug libraries. The design of peptide mimetics can be aided by identifying amino acid mutations that increase or decrease binding of Nogo at the NgR. Approaches that can be used include the yeast two hybrid method (see Chien et al., (1991) Proc. Natl. Acad. Sci. USA 88, 9578–9582) and using the phage display method. The two hybrid method detects protein-protein interactions in yeast (Fields et al., (1989) Nature 340, 245–246). The phage display method detects the interaction between an immobilized protein and a protein that is expressed on the surface of phages such as lambda and M13 (Amberg et al., (1993) Strategies 6, 2–4; Hogrefe et al., (1993) Gene 128, 119–126). These methods allow positive and negative selection for protein-protein interactions and the identification of the sequences that determine these interactions.

For general information on peptide synthesis and peptide mimetics, see, for example; Jones, (1992) Amino Acid and Peptide Synthesis, Oxford University Press; Jung, (1997) Combinatorial Peptide and Nonpeptide Libraries: A Handbook John Wiley; Bodanszky et al., (1993) Peptide Chemistry—A Practical Textbook, Springer Verlag.

L. Transgenic Animals

The term "animal" as used herein includes all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA. The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals. Transgenic animals containing mutant, knock-out, modified genes or gene constructs to over-express or conditionally express a polypeptide encoded by the cDNA sequences of SEQ ID NO: 1 or 3 or related sequences are encompassed in the invention.

To be expressed, a coding sequence should be operably linked to a regulatory region. Regulatory regions, such as promoters, may be used to increase, decrease, regulate or designate to certain tissues or to certain stages of development the expression of a gene. The promoter need not be a naturally occurring promoter. The "transgenic non-human animals" of the invention are produced by introducing "transgenes" into the germline of the non-human animal. The methods enabling the introduction of DNA into cells are generally available and well-known in the art. Different methods of introducing transgenes could be used. Generally, the zygote is the best target for microinjection. In the mouse, the male pronucleus reaches the size of approximately twenty microns in diameter, which allows reproducible injection of one to two picoliters of DNA solution. The use of zygotes as a target for gene transfer has a major advantage. In most cases, the injected DNA will be incorporated into the host gene before the first cleavage (Brinster et al., (1985) Proc. Natl. Acad. Sci. USA 82, 4438–4442). Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is a preferred method for incorporating transgenes in practicing the invention.

Retroviral infection can also be used to introduce a transgene into a non-human animal. The developing non-human embryo can be cultured in vitro to the blastocyst stage. During this time, blastomeres may be targets for retroviral infection. Efficient infection of the blastomeres is obtained by enzymatic treatment to remove the zona pellucida. The viral vector system used to introduce the transgene is typically a replication-defective retrovirus carrying the transgene (Jahner et al., (1985) Proc. Natl. Acad. Sci. USA 82, 6927–6931; Van der Putten et al., (1985) Proc. Natl. Acad. Sci. USA 82, 6148–6152). Transfection is easily and efficiently obtained by culturing the blastomeres on a monolayer of virus-producing cells (Van der Putten et al., (1985) Proc. Natl. Acad. Sci. USA 82, 6148–6152; Stewart et al., (1987) EMBO J. 6, 383–388). Alternatively, infection can be performed at a later stage. Virus or virus-producing cells can be injected into the blastocoele (Jahner et al., (1982) Nature 298, 623–628). Most of the founder animals will be mosaic for the transgene since incorporation occurs only in a subset of the cells which formed the transgenic non-human animal. Furthermore, the founder animal may contain retroviral insertions of the transgene at a variety of positions in the genome; these generally segregate in the offspring. In addition, it is also possible to introduce transgenes into the germ line, albeit with low efficiency, by intrauterine retroviral infection of the midgestation embryo (Jahner et al., (1982) Nature 298, 623–628).

A third type of target cell for transgene introduction is the embryonal stem cell (ES). ES cells are obtained from pre-implantation embryos cultured in vitro (Evans et al., (1981) Nature 292, 154–156; Bradley et al., (1984) Nature 309, 255–256; Gossler et al., (1986) Proc. Natl. Acad. Sci. USA 83, 9065–9069). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal.

The methods for evaluating the presence of the introduced DNA as well as its expression are readily available and well-known in the art. Such methods include, but are not limited to DNA (Southern) hybridization to detect the exogenous DNA, polymerase chain reaction (PCR), polyacrylamide gel electrophoresis (PAGE) and Western blots to detect DNA, RNA and protein. The methods include immunological and histochemical techniques to detect expression of a NgR gene.

As discussed above, a nucleic acid of the invention can be transfected into a host cell using a vector. Preferred vectors are plasmids and viral vectors, such as retroviruses. Viral vectors may be used to produce a transgenic animal according to the invention. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents.

Preferably, the replication defective virus retains the sequences of its genome which are necessary for encapsidating the viral particles. The retroviruses are integrating viruses which infect dividing cells. The retrovirus genome includes two LTRs, an encapsidation sequence and three coding regions (gag, pol and env). The construction of recombinant retroviral vectors has been described (see, for example, Bernstein et al., (1985) Genet. Eng. 7, 235; McCormick, (1985) Biotechnol. 3, 689–691). In recombinant retroviral vectors, the gag, pol and env genes are generally deleted, in whole or in part, and replaced with a heterologous nucleotide sequence of interest. These vectors can be constructed from different types of retrovirus, such as, HIV, MoMuLV (murine Moloney leukemia virus), MSV (murine Moloney sarcoma virus), HaSV (Harvey sarcoma virus); SNV (spleen necrosis virus); RSV (Rous sarcoma virus) and Friend virus.

In general, in order to construct recombinant retroviruses containing a nucleotide sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO9002806) and the GP+envAm-12 cell line (WO8907150). In addition, the recombinant retroviral vectors can contain modifications within the LTRs for suppressing transcriptional activity as well as extensive encapsidation sequences which may include a part of the gag gene (Bender et al., (1987) J. Virol. 61, 1639–1646). Recombinant retroviral vectors are purified by standard techniques known to those having ordinary skill in the art.

In one aspect the nucleic acid encodes antisense RNA molecules. In this embodiment, the nucleic acid is operably linked to suitable regulatory regions (discussed above) enabling expression of the nucleotide sequence, and is introduced into a cell utilizing, preferably, recombinant vector constructs, which will express the antisense nucleic acid once the vector is introduced into the cell. Examples of suitable vectors includes plasmids, adenoviruses, adeno-associated viruses (see, for example, U.S. Pat. No. 4,797,368, U.S. Pat. No. 5,139,941), retroviruses (see above), and herpes viruses. For delivery of a therapeutic gene the vector is preferably an adeno-associated virus.

Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type two or type five human adenoviruses (Ad 2 or Ad 5) or adenoviruses of animal origin (see WO9426914). Those adenoviruses of animal origin which can be used within the scope of the present invention include adenoviruses of canine, bovine, murine, ovine, porcine, avian, and simian origin.

The replication defective recombinant adenoviruses according to the invention can be prepared by any technique known to the person skilled in the art. In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Recombinant adenoviruses are recovered and purified using standard molecular biological techniques, which are well known to one of ordinary skill in the art.

A number of recombinant or transgenic mice have been produced, including those which express an activated oncogene sequence (U.S. Pat. No. 4,736,866); express Simian SV 40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess a bovine growth hormone gene (Clutter et al., (1996) Genetics 143, 1753–1760) or are capable of generating a fully human antibody response (Zou et al., (1993) Science 262, 1271–1274).

While mice and rats remain the animals of choice for most transgenic experimentation, in some instances it is preferable or even necessary to use alternative animal species. Transgenic procedures have been successfully utilized in a variety of non-murine animals, including sheep, goats, chickens, hamsters, rabbits, cows and guinea pigs (see Aigner et al., (1999) Biochem. Biophys. Res. Commun. 257, 843–850; Castro et al., (1999) Genet. Anal. 15, 179–187; Brink et al., (2000) Theriogenology 53, 139–148; Colman, (1999) Genet. Anal. 15, 167–173; Eyestone, (1999) Theriogenology 51, 509–517; Baguisi et al., (1999) Nat. Biotechnol. 17, 456–461; Prather et al., (1999) Theriogenology 51, 487–498; Pain et al., (1999) Cells Tissues Organs 165, 212–219; Fernandez et al., (1999) Indian J. Exp. Biol. 37, 1085–1092; U.S. Pat. No. 5,908,969; U.S. Pat. No. 5,792,902; U.S. Pat. No. 5,892,070; U.S. Pat. No. 6,025,540).

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

Key for Sequence Listing

| SEQ ID NO: | Description |
| --- | --- |
| SEQ ID NO: 1 | human NgR nucleotide sequence |
| SEQ ID NO: 2 | human NgR amino acid sequence |
| SEQ ID NO: 3 | mouse NgR nucleotide sequence |
| SEQ ID NO: 4 | mouse NgR amino acid sequence |
| SEQ ID NO: 5 | human NogoA nucleotide sequence |
| SEQ ID NO: 6 | human NogoA amino acid sequence |
| SEQ ID NO: 7 | a nucleotide sequence coding for amino acid residues #1054–1078 of a human NogoA |
| SEQ ID NO: 8 | amino acid residues #1064–1088 of human NogoA |
| SEQ ID NO: 9 | a nucleotide sequence coding for amino acid residues #1064–1088 of a human NogoA |
| SEQ ID NO: 10 | amino acid residues #1064–1088 of human NogoA |
| SEQ ID NO: 11 | a nucleotide sequence coding for amino acid residues #1064–1088 of a human NogoA |
| SEQ ID NO: 12 | amino acid residues #1064–1088 of a human NogoA |
| SEQ ID NO: 13 | a nucleotide sequence coding for amino acid residues #1084–1108 of a human NogoA |
| SEQ ID NO: 14 | amino acid residues #1084–1108 of a human NogoA |
| SEQ ID NO: 15 | a nucleotide sequence coding for amino acid residues #1095–1119 of a human NogoA |
| SEQ ID NO: 16 | amino acid residues #1095–1119 of a human NogoA |
| SEQ ID NO: 17 | a nucleotide sequence coding for amino acid residues #1055–1094 of a human NogoA |
| SEQ ID NO: 18 | amino acid residues #1055–1094 of a human NogoA |
| SEQ ID NO: 19 | a nucleotide sequence coding for amino acid residues #1054–1119 of a human NogoA |
| SEQ ID NO: 20 | amino acid residues #1054–1119 of a human NogoA |
| SEQ ID NO: 21 | a nucleotide sequence coding for amino acid residues #1055–1120 of a human NogoA |
| SEQ ID NO: 22 | amino acid residues #1055–1120 of a human NogoA |
| SEQ ID NO: 23 | a nucleotide sequence coding for amino acid residues #1055–1079 of a human NogoA |
| SEQ ID NO: 24 | amino acid residues #1055–1079 of a human NogoA |
| SEQ ID NO: 25 | a nucleotide sequence coding for amino acid residues #1055–1084 of a human NogoA |
| SEQ ID NO: 26 | amino acid residues #1055–1084 of a human NogoA |
| SEQ ID NO: 27 | a nucleotide sequence coding for amino acid residues #1055–1089 of a human NogoA |
| SEQ ID NO: 28 | amino acid residues #1055–1089 of a human NogoA |
| SEQ ID NO: 29 | a nucleotide sequence coding for amino acid residues #1060–1094 of a human NogoA |
| SEQ ID NO: 30 | amino acid residues #1060–1094 of a human NogoA |
| SEQ ID NO: 31 | a nucleotide sequence coding for amino acid residues #1065–1094 of a human NogoA |
| SEQ ID NO: 32 | amino acid residues #1065–1094 of a human NogoA |
| SEQ ID NO: 33 | a nucleotide sequence coding for amino acid residues #1070–1084 of a human NogoA |
| SEQ ID NO: 34 | amino acid residues #1070–1084 of a human NogoA |
| SEQ ID NO: 35 | a nucleotide sequence coding for amino acid residues #1085–1109 of a human NogoA |
| SEQ ID NO: 36 | amino acid residues #1085–1109 of a human NogoA |
| SEQ ID NO: 37 | ALRR-NT5' primer |
| SEQ ID NO: 38 | NgR3X primer |
| SEQ ID NO: 39 | MycNgR305 primer |
| SEQ ID NO: 40 | MycNgR primer |
| SEQ ID NO: 41 | 2NgRt313 primer |
| SEQ ID NO: 42 | TM/GPI5' primer |
| SEQ ID NO: 43 | DEL LRR1 primer |
| SEQ ID NO: 44 | DEL LRR2 primer |
| SEQ ID NO: 45 | DEL LRR3 primer |
| SEQ ID NO: 46 | DEL LRR4 primer |
| SEQ ID NO: 47 | DEL LRR5 primer |
| SEQ ID NO: 48 | DEL LRR6 primer |
| SEQ ID NO: 49 | DEL LRR7 primer |
| SEQ ID NO: 50 | DEL LRR8 primer |

-continued

| SEQ ID NO: | Description |
|---|---|
| SEQ ID NO: 51 | 3DLRR CT primer |
| SEQ ID NO: 52 | 5 DLRRCT primer |
| SEQ ID NO: 53 | amino acid residues #306–442 of a human NgR |
| SEQ ID NO: 54 | amino acid residues #306–473 of a human NgR |
| SEQ ID NO: 55 | amino acid residues #27–309 of a human NgR |

EXAMPLES

Example 1

Identification of Nogo as a Member of the Reticulon Family of Proteins

Adult mammalian axon regeneration is generally successful in the periphery but dismally poor in the CNS. However, many classes of CNS axons can extend for long distances in peripheral nerve grafts (Benfy & Aguayo (1982) Nature 296, 150–152). Comparison of CNS and peripheral nervous system (PNS) myelin has revealed that CNS white matter is selectively inhibitory for axonal outgrowth (Schwab & Thoenen (1985) J. Neurosci. 5, 2415–2423). Several components of CNS white matter, NI35, NI250 (Nogo) and MAG, with inhibitory activity for axon extension have been described (Wang et al., (1999) Transduction of inhibitory signals by the axonal growth cone, in Neurobiology of Spinal Cord Injury, Kalb & Strittmatter (editors) Humana Press; Caroni & Schwab, (1988) J. Cell Biol. 106, 1281–1288; Spillmann et al., (1998) J. Biol. Chem. 73, 19283–19293; McKerracher et al., (1994) Neuron 13, 805–811; Mukhopadhyay et al., (1994) Neuron 13, 757–767.) The IN-1 antibody raised against NI35 and NI250 (Nogo) has been reported to allow moderate degrees of axonal regeneration and functional recovery after spinal cord injury (Bregman et al., (1995) Nature 378, 498–501; Thallmair et al., (1998) Nature Neurosci. 1, 24–31). The present invention identifies Nogo as a member of the Reticulon protein family.

Nogo is expressed by oligodendrocytes but not by Schwann cells, and associates primarily with the endoplasmic reticulum. The 66 amino acid lumenal-extracellular domain of Nogo (SEQ ID NO: 20) inhibits axonal extension and collapses dorsal root ganglion growth cones. Other Reticulon proteins are not expressed by oligodendrocytes, and the 66 amino acid lumenal-extracellular domain from other Reticulon proteins does not inhibit axonal regeneration. These data provide a molecular basis to assess the contribution of Nogo to the failure of axonal regeneration in the adult CNS.

For expression and protein purification of recombinant Nogo-A, the full length sequence (KIAA0886) was generously provided by the Kazusa DNA Research Institute. The full length coding sequence was amplified by the polymerase chain reaction (PCR) and ligated into the pCDNA3.1-MycIis vector (Invitrogen) to generate a plasmid encoding Nogo-A fused at the carboxyl terminus to the Myc epitope (Nogo-A-Myc). Alternatively, the coding sequence was amplified using primers that encode an in-frame Myc epitope immediately amino terminal to the first residue and a stop codon at the carboxyl terminus (Myc-Nogo-A). The Nogo-C-MycHis and Rtn1C-MycHis expression vectors were derived in the same fashion except that an adult rat brain cDNA library was used as template for a PCR reaction with primers was based on the Nogo-C or Rtn1C sequences (Van de Velde et al., (1994) J. Cell. Sci. 107, 2403–2416). These plasmids were transfected into COS-7 or HEK293T by the Lipofectamine (Gibco-BRL) or the FuGENE 6 (Boehringer Mannheim) method.

A portion of Nogo-A encoding the 66 amino acid lumenal-extracellular fragment of Nogo-A was amplified by PCR and ligated into the pGEX-2T plasmid to yield a prokaryotic expression vector for the GST-Nogo fusion protein. Similar regions of Rtn1, Rtn2 and Rtn3 were amplified by nested PCR using an adult rat brain cDNA library as template and ligated to pGEX-2T. E. coli transformed with these plasmids were induced with IPTG. Soluble, native GST fusion proteins were purified using a glutathione-resin and contained approximately 75% GST and 25% full length GST-Nogo or GST-Rtn protein. The majority of the GST-Nogo protein was not extractable from under non-denaturing conditions, but an 8 M urea extract dialyzed against PBS contained over 98% pure GST-Nogo.

Myc immunoreactivity is detectable with an apparent size in the 225 kDa range under reducing conditions (data not shown). Thus, the cDNA directs the expression of a protein with appropriate electrophoretic mobility and the amino acid sequence to be Nogo which was termed human Nogo-A (hNogo-A).

The conserved carboxyl tail of the Rtn family proteins contains two hydrophobic domains separated by a 66 amino acid residue hydrophilic segment. None of the sequences contain a signal peptide. The predicted topology for these proteins is for the amino and carboxyl termini to reside in the cytosol, and for the conserved region to associate with the lipid bilayer. For Rtn1-A, there is experimental evidence demonstrating that the polypeptide behaves as an integral membrane protein, and that the hydrophobic segments of the conserved domain are responsible for this behavior (Van de Velde et al., (1994) J. Cell. Sci. 107, 2403–2416). Myc-tagged Nogo is also associated with particulate fractions and is extracted by detergent but not high ionic strength (data not shown).

When overexpressed in kidney cells, the Rtn1 protein is localized primarily to endoplasmic reticulum (ER) in a finely granulated pattern, hence the Reticulon name (Van de Velde et al., (1994) J. Cell. Sci. 107, 2403–2416). There is a di-lysine ER retention motif at the carboxyl terminus of Nogo and most Rtn proteins (Van de Velde et al., (1994) J. Cell. Sci. 107, 2403–2416; Jackson et al., (1991) EMBO J. 9, 3153–3162). In neurons, Rtn1 is expressed throughout processes and is concentrated in growth cones (Senden et al., (1996) Eur. J. Cell. Biol. 69, 197–213). Its localization in transfected kidney cells has led to the suggestion that Rtn1 might regulate protein sorting or other aspects of ER function (Van de Velde et al., (1994) J. Cell. Sci. 107, 2403–2416). Both the A and C splice forms of Nogo exhibit a reticular distribution when expressed in COS-7 cells, similar to that of Rtn1-C.

Example 2

Polyclonal Antibodies Against Nogo

The predicted intra-membrane topology of the two hydrophobic domains of Nogo indicates that the 66 amino acid residues between these segments is localized to the lumenal/extracellular face of the membrane. To explore this further, an antiserum directed against the 66 amino acid domain was generated.

For antibody production and immunohistology, anti-Myc immunoblots and immunohistology with the 9E10 antibody were obtained as described in Takahashi et al., (1998) Nature Neurosci., 1, 487–493 & Takahashi et al., (1999) Cell, 99, 59–69. The GST-Nogo fusion protein was employed as an immunogen to generate an anti-Nogo rabbit antiserum. Antibody was affinity-purified and utilized at 3 µg/ml for immunohistology and 1 µg/ml for immunoblots. To assess the specificity of the antiserum, staining was conducted in the presence of GST-Nogo protein at 0.1 mg/ml. For live cell staining, cells were incubated in primary antibody dilutions at 4° C. for one hour in Hanks balanced salt solution with 0.05% BSA and 20 mM Na-Hepes (pH 7.3). After fixation, bound antibody was detected by incubation with fluorescently labeled secondary antibodies.

The antibody detects a low level of surface expression of this epitope, while the Myc epitope at the carboxyl terminus of expressed Nogo is not detected unless cells are permeablized. This surface staining was attributed to a minority of Nogo protein associated with the plasma membrane rather than the ER membrane. This data supports a topographic model wherein the amino and carboxyl termini of the protein reside in the cytoplasm and 66 amino acid of the protein protrude on the lumenal-extracellular side of the ER or plasma membrane.

Example 3

Nogo Expression in the Central Nervous System

If Nogo is a major contributor to the axon outgrowth inhibitory characteristics of CNS myelin as compared to PNS myelin (Caroni & Schwab, (1988) J. Cell Biol. 106, 1281–1288; Spillmann et al., (1998) J. Biol. Chem. 73, 19283–19293; Bregman et al., (1995) Nature 378, 498–501), then Nogo should be expressed in adult CNS myelin but not PNS myelin. Northern blot analysis of Nogo expression was performed using probes derived from the 5' Nogo-A/B-specific region and from the 3' Nogo common region of the cDNA. A single band of about 4.1 kilobase was detected with the 5' probe in adult rat optic nerve total RNA samples, but not sciatic nerve samples. The results indicate that the Nogo-A clone is a full length cDNA, and are consistent with a role for Nogo as a CNS-myelin-specific axon outgrowth inhibitor. Northern blot analysis with a 3' probe reveals that optic nerve expresses high levels of the Nogo-A mRNA and much lower levels of Nogo-B and Nogo-C. Whole brain expresses both Nogo-A and Nogo-C, but a number of peripheral tissues (including sciatic nerve) express little or no Nogo. Nogo-C/Rtn4-C expression has been demonstrated in skeletal muscle and adipocytes, as well as in brain (Morris et al., (1991) Biochim. Biophys. Acta 1450, 68–76). Within the Rtn family, optic nerve expression appears to be selective for Nogo, with no detectable expression of Rtn 1 or Rtn 3. Rtn 2 has not been examined.

In situ hybridization reveals Nogo mRNA in cells with the morphology of oligodendrocytes in adult rat optic nerve and pyramidal tract. Within the brain, Nogo expression is also detected in certain neuronal populations. In contrast to Nogo, Rtn1 and Rtn3 are not expressed in optic nerve but mRNA is detected in certain neuronal populations. Nogo protein localization was analyzed in spinal cord cultures treated with PDGF and low serum to induce oligodendrocyte differentiation, using the anti-Nogo antibody and the oligodendrocyte-specific O4 monoclonal antibody. In living cells, both the lumenal-extracellular 66 amino acid loop of Nogo and the O4 antigen are detected on the surface of oligodendrocytes. Approximately half of O4-positive cells in these cultures exhibit Nogo surface staining.

Example 4

Nogo-Mediated Growth Cone Collapse

For all experiments involving cell culture, the following methods were employed. The culture of embryonic chick E10 and E12 dorsal root ganglion explants and dissociated neurons utilized methods described for E7 dorsal root ganglion cultures (Takahashi et al., (1998) Nature Neurosci. 1, 487–493; Takahashi et al., (1999) Cell 99, 59–69; Goshima et al., (1995) Nature 376, 509–514; Jin & Strittmatter, (1997) J. Neurosci. 7, 6256–6263). NGF-differentiated PC 12 cells were cultured as described (Strittmatter et al., (1994) J. Neurosci. 14, 2327–2338). Embryonic spinal cord explants (rat E10 or chick E5) were cultured for 7–14 days in the presence of PDGF-AA to induce differentiation of some cells into mature oligodendrocytes (Vartanian et al., (1999) Proc. Natl. Acad. Sci. USA 96, 731–735). The procedure for growth cone collapse assays is identical to that for analysis of Sema3A-induced growth cone collapse (Takahashi et al., (1998) Nature Neurosci. 1, 487–493; Takahashi et al., (1999) Cell 99, 59–69; Goshima et al., (1995) Nature 376, 509–514; Jin & Strittmatter, (1997) J. Neurosci. 17, 6256–6263). The method for analysis of total neurite outgrowth has also been described (Goshima et al., (1995) Nature 376, 509–514; Jin & Strittmatter, (1997) J. Neurosci. 17, 6256–6263; Strittmatter et al., (1994) J. Neurosci. 14, 2327–2338). In outgrowth assays, proteins and peptides were added one hour after plating to minimize any effect on the total number of adherent cells. To test the effect of substrate-bound GST or GST-Nogo, the protein solutions were dried on poly-L-lysine coated glass, washed and then coated with laminin. For E12 cultures, the neuronal identity of cells was verified by staining with anti-neurofilament antibodies (2H3, Develomental Studies Hybridoma Bank) and neurites were traced by observation of rhodamine-phalloidin staining of F-actin in processes.

The expression of recombinant Nogo in HEK293T cells allows a rigorous test of whether this protein has axon outgrowth inhibiting effects. Washed membrane fractions from vector- or hNogo-A-Myc-transfected HEK293T cells were added to chick E12 dorsal root ganglion explant cultures. Growth cone morphology was assessed after a thirty minute incubation at 37° C. by fixation and rhodamine-phalloidin staining.

The control HEK membranes have no detectable effect on growth cone morphology. The Nogo-A-containing membrane fractions induced collapse of a majority of dorsal root ganglion growth cones. This growth cone collapse indicates an axon outgrowth inhibiting activity, and Nogo inhibition of axon extension is also demonstrable (see below). The Nogo-C form also exhibits collapse activity, indicating that the shared carboxyl terminus of the protein including the hydrophobic segments and the 66 amino acid lumenal-extracellular domain contains functionally important residues. Additional inhibitory activity in the amino terminal region of Nogo-A is not excluded by these studies. The sensitivity of more immature explant cultures from E10 chick embryos or from E15 rat embryos (data not shown) is substantially less. The developmental regulation of sensitivity is consistent with experiments using partially purified Nogo (Bandtlow et al., (1997) Eur. J. Neurosci. 9, 2743–2752).

Within the growth cone collapsing Nogo-C protein, the hydrophilic 66 lumenal-extracellular domain seems more likely to interact with the surface of dorsal root ganglion neurons than do the membrane-embedded hydrophobic domains. To test this hypothesis, the 66 amino acid region of hNogo was expressed in and purified from E. coli. A majority of the GST-Nogo fusion protein accumulates in inclusion bodies, but can be recovered by urea extraction. This restricted region of Nogo possesses potent (EC50=50 nM) growth cone collapsing activity for chick E12 dorsal root ganglion neurons (data not shown). The urea-extracted protein preparation is likely to present only a small fraction of the Nogo sequence in an active conformation. Therefore, 10% of GST-Nogo that is soluble in E. coli was purified using a glutathione-Sepharose resin. This preparation is even more potent than the urea-extracted protein as a collapsing factor, acutely altering growth cone morphology at concentrations as low as 1 nM.

The nanomolar potency is on a par with most known physiologic regulators of axon guidance. Axon outgrowth from dorsal root ganglion neurons and NGF-differentiated PC12 cells is also blocked by this soluble GST-Nogo protein in nM concentrations (data not shown). When GST-Nogo is bound to substrate surfaces, axonal outgrowth from dorsal root ganglion neurons or PC12 cells is reduced to undetectable levels. These are selective effects on axon outgrowth rather than cell survival since GST-Nogo does not reduce the number of neurofilament-positive adherent cells (137±24% of GST-treated cultures) nor significantly alter the number of apoptotic nuclei identified by DAPI staining (4.0±1.7% in control cultures and 5.2±1.1% in GST-Nogo-treated specimens).

Oligodendrocytes appear to express Nogo selectively amongst the Rtn proteins. To explore the selectivity of Nogo s role in the inhibition of axonal regeneration, the axon outgrowth inhibiting activity of other Rtn proteins was considered. The predicted lumenal-extracellular 66 amino acid fragments of Rtn1, Rtn2 and Rtn3 were expressed as GST fusion proteins and purified in native form. At concentrations in which the Nogo fragment collapses a majority of E12 dorsal root ganglion growth cones, the other Rtn proteins do not alter growth cone morphology (data not shown). Thus, the axon regeneration inhibiting activity is specific for Nogo in the Rtn family.

Example 5

NgR Peptide Agents

To further define the active domain of Nogo, 25 amino acid residue peptides corresponding to segments of the 66 amino acid sequence were synthesized. The peptide corresponding to residues 31–55 of the extracellular fragment of Nogo exhibits growth cone collapsing (FIG. 2) and outgrowth inhibiting (data not shown) activities at concentrations of 4 µM. While this sequence may provide the core of the inhibitory domain, the 66 amino acid fragment is clearly required for fill potency. Interestingly, this is the region within the 66 amino acid domain sharing the least similarity to other Rtn proteins, consistent with the other family members being inactive as axon regeneration inhibitors. Indeed, the Rtn1 31–55 amino acid lumenal-extracellular peptide exerts no growth cone collapse activity (data not shown).

The aforementioned experimental data identifies Nogo as an oligodendrocyte-specific member of the Rtn family and demonstrates that a discrete domain of Nogo can inhibit axon outgrowth. Other Rtn proteins do not possess this activity. The expression of Nogo in oligodendrocytes but not Schwann cells therefore contributes to the failure of axonal regeneration in the adult mammalian CNS as compared to the adult PNS. The relative contribution of Nogo as compared to other CNS myelin components to the non-permissive nature of CNS white matter can now be characterized at a molecular level.

While the current experimental data is consistent with a role for Nogo in blocking adult CNS axonal regeneration after pathologic injury, this may also be related to the physiologic role of Nogo in non-pathologic states. Based on localization studies, other Rtn proteins are thought to play a role in ER function (Van de Velde et al., (1994) J. Cell. Sci. 107, 2403–2416). A majority of Nogo is distributed in a reticular pattern in COS-7 cells and only a minority seems to be accessible at the cell surface.

Example 6

Inhibition of Nogo Activity

The previous examples have shown that a 66 amino acid region near the carboxyl terminus of Nogo inhibits axon outgrowth and is expressed at the cell surface. Shorter twenty-five amino acid segments of this domain are either inert as outgrowth inhibitors or of much lower potency (GrandPré et al., (2000) Nature 403, 439–444). The 31–55 region from this 66 amino acid segment has weak growth cone collapse and axon outgrowth inhibiting activity. To block Nogo action in vivo, a competitive antagonist of Nogo which binds to the same receptor site but does not exert a biological effect in its own right would be highly desirable. Various fragments of the 66 amino acid region were tested as blockers of Nogo-mediated axon growth inhibition. Two assays have been used for this purpose. The first is the growth cone collapse assay and the second is a binding assay.

Figure 2A:
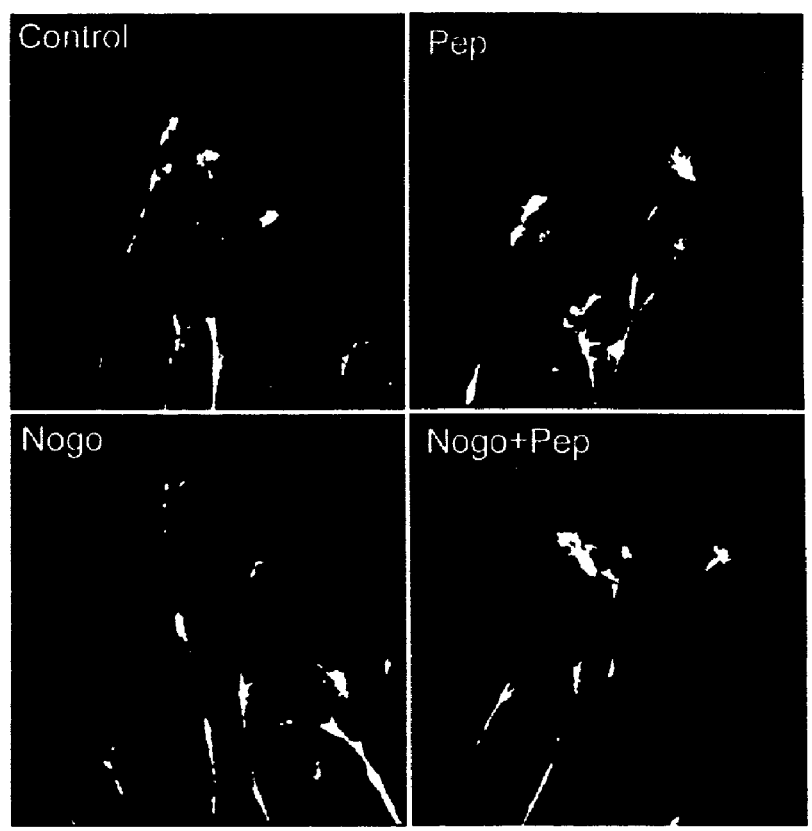
FIG. 2—Nogo fragments antagonize Nogo and CNS myelin action (a) is a photograph of chick E12 dorsal root ganglion explants that were cultured and growth cone collapse assessed as described in FIG. 4. Cultures were exposed to the following preparations for thirty minutes before fixation and staining with rhodamine-phalloidin: buffer only (Control); 15 nM GST-Nogo); 1 µM each of Pep1, Pep2 and Pep3 (Pep); 15 nM GST-Nogo plus 1 µM each of Pep1, Pep2 and Pep3 (Nogo+Pep). Note that growth cone collapse by Nogo is blocked by peptide addition. Pep1, residues 1–25 of the extracellular domain; Pep2, 11–35; and Pep3, 21–45. (b) is a graph quantifying the results from growth cone collapse assays as in (a). Individual peptides were included at 4 µM, and the peptide 1–3 mixture was 1 µM of each peptide. CNS myelin was prepared as described and the indicated total myelin protein concentrations were included in the cultures. All results are the means±s.e.m. calculated from four to seven determinations. Those values significantly different from the corresponding values with the same concentration of Nogo or myelin but without peptide are indicated (asterisk, $p<0.05$, Student's two-tailed t test).
Figure 2B:
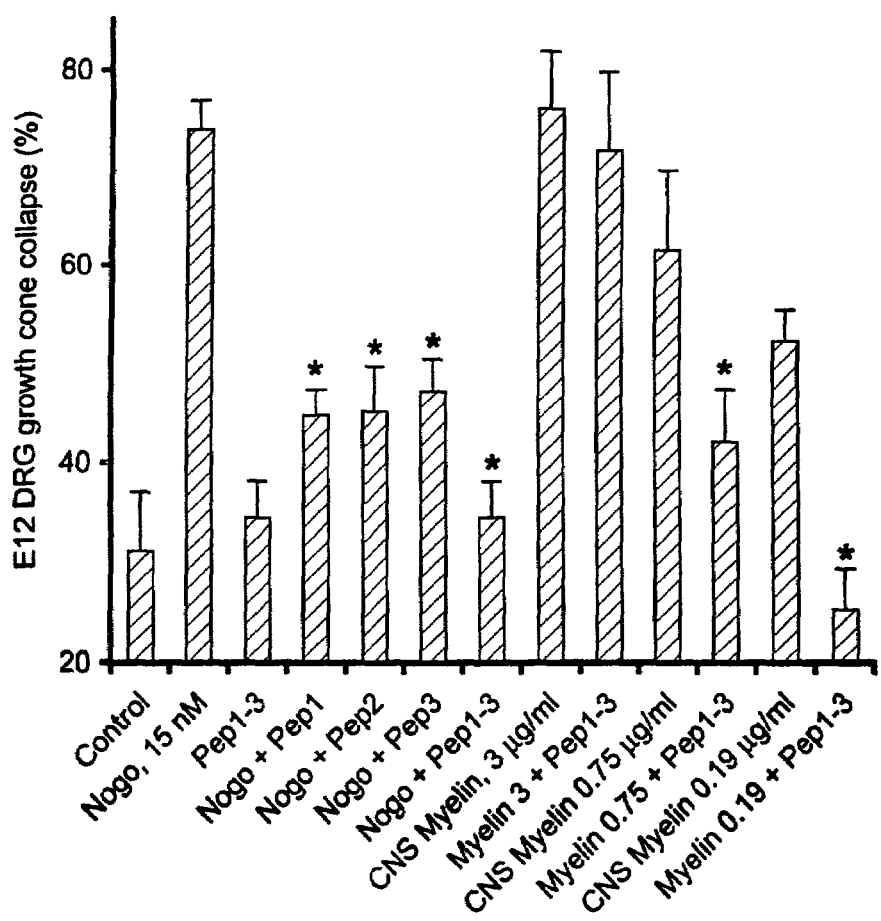

In the growth cone collapse assay, the response to Nogo was measured in the presence of various potential antagonistic peptides. Three of the twenty-five amino acid peptides (1–25, 11–35 and 21–45) from the 66 amino acid region possess blocking activity at µM concentrations (FIG. 2). The combination of all three peptides does not alter growth cone morphology under basal conditions but totally prevents collapse by 15 nM GST-Nogo. The same mixture of peptides is also capable of blocking low dose CNS myelin induced growth cone collapse. This blockade supports the hypothesis that Nogo is a primary inhibitory component of CNS myelin. Furthermore, the blockade has properties expected for competitive antagonism, being ineffective at high doses of CNS myelin.

Figure 3A:
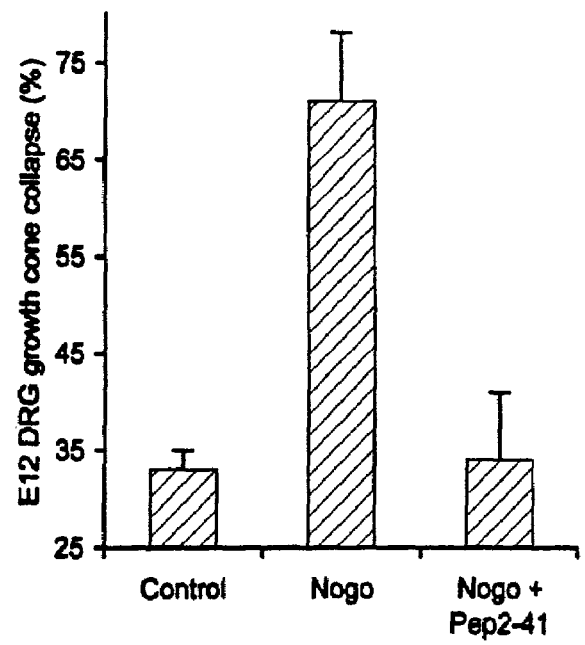
FIG. 3—Nogo antagonist Pep2-41
Figure 3B:
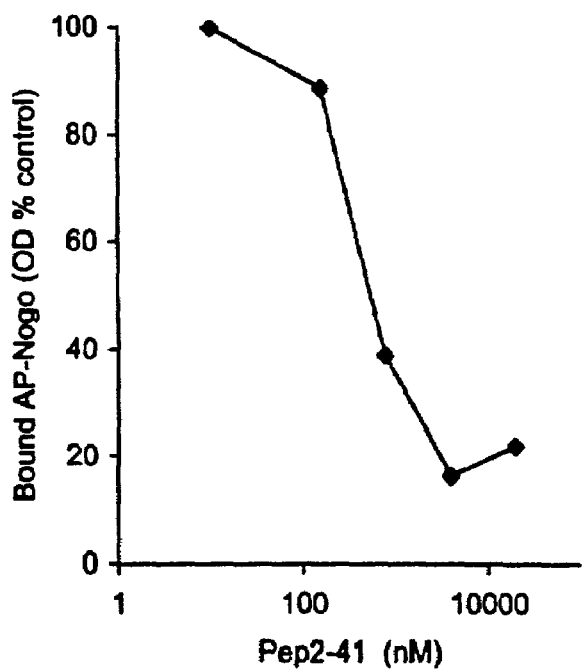

To develop an antagonist with higher specificity and potency, a longer fragment of Nogo has been tested. Preferentially, such a peptide itself has no axon outgrowth inhibiting activity on its own while competitively blocking Nogo action. The 2-41 fragment of Nogo is acetylated at the carboxy terminus and amidated at the amino terminous and is the highest potency blocker of Nogo defined to date. Pep2-41 abolishes GST-Nogo-induced growth cone collapse and possesses an apparent $K_i$ of 150 nM in the binding assay (FIG. 3). The 2-41 fragment also blocks the ability of both purified Nogo-66 protein and crude CNS myelin to inhibit neurite outgrowth in cultured neurons (FIG. 4).

Example 7

Identification of the NgR

A Nogo binding assay was developed which utilizes a method widely used in examining semaphorin and ephrin axonal guidance function (Flanagan & Vanderhaeghen, (1998) Annu. Rev. Neurosci. 21, 309–345; Takahashi et al., (1999) Cell 99, 59–69). It involves fusing a secreted placental alkaline phosphatase (AP) moiety to the ligand in question to provide a biologically active receptor binding agent which can be detected with an extremely sensitive colorimetric assay. For Nogo, an expression vector was created encoding a signal peptide, a His6 tag for purification, AP and the 66 amino acid active domain of Nogo. The fusion protein can be purified from the conditioned medium of transfected cells in milligram amounts (FIG. 5). This protein is biologically active as a growth cone collapsing agent, with an $EC_{50}$ of 1 nM. AP-Nogo is actually slightly more potent than GST-Nogo perhaps because the protein is synthesized in eukaryotic rather than a prokaryotic cell. Initial studies have revealed saturable, high affinity sites on axons. Binding is blocked by GST-Nogo and by the antagonistic 25 amino acid peptides, consistent with competitive binding to a neuronal receptor site. Since the apparent $K_d$ (3 nM) for these sites in close to the $EC_{50}$ of AP-Nogo in the collapse assay, the sites are likely to be physiologically relevant NgRs.

This assay was utilized for expression cloning of a NgR. Pools of a mouse adult brain cDNA expression library representing 250,000 independent clones were transfected into non-neuronal COS-7 cells. Non-transfected COS-7 cells do not bind AP-Nogo, but transfection with two pools of 5,000 clones exhibited a few cells with strong AP-Nogo binding. Single cDNA clones encoding a Nogo biding site were isolated by sib-selection from each of the two positive pools. The two independently isolated clones are identical to one another except for a 100 bp extension of the 5' untranslated region in one clone. Transfection of these clones into COS-7 cells yields a binding site with an affinity for AP-Nogo identical to that observed in E13 dorsal root ganglion neurons; the $K_d$ for binding is about 3 nM (FIG. 6). AP alone does not bind with any detectable affinity to these transfected cells, indicating that the affinity is due to the 66 amino acid derived from Nogo. Furthermore, GST-Nogo displaces AP-Nogo from these sites.

This cDNA encodes a novel 473 amino acid protein. There is no reported cDNA with significant homology in GenBank. The predicted protein contains a signal peptide followed by eight leucine-rich repeat regions, a unique domain and a predicted GPI anchorage site (FIG. 7). A human homologue of the murine cDNA was identified that shares 89% amino acid identity. The existence of this cDNA was predicted from the murine cDNA structure and analysis of human genomic sequence deposited in GenBank as part of the Human Sequencing Project. The exons of the human cDNA are distributed over 35 kilobases and the cDNA was not previously recognized in the genomic sequence. The protein structure is consistent with a cell surface protein capable of binding Nogo. The GPI-linked nature of the protein suggests that there may be a second receptor subunit that spans the plasma membrane and mediates Nogo signal transduction.

Example 8

Tissue Distribution of NgR

The distribution of the mRNA for this NgR is consistent with a role for the protein in regulating axonal regeneration and plasticity in the adult CNS. Northern analysis shows a single band of 2.3 kilobases in the adult brain, indicating that the isolated NgR clone is full length (FIG. 8). Low levels of this mRNA are observed in heart and kidney but not in other peripheral tissues. In the brain, expression is widespread and those areas richest in gray matter express the highest levels of the mRNA.

Example 9

Biological Effects of Different Nogo Domains

Figure 1A:
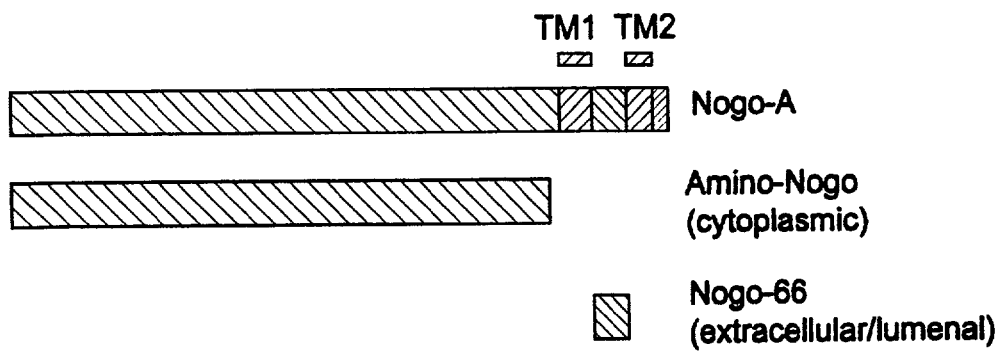
FIG. 1—Comparison of Nogo domains (a) is a schematic diagram which summarizes features of the Nogo proteins utilized in this study. (b) is a photograph of NIH-3T3 fibroblasts cultured on surfaces coated with Amino-Nogo, GST-Nogo-66 or no protein and stained for filamentous actin (scale bar, 40 µm). (c) is a photograph of chick E12 dorsal root ganglions cultured on surfaces coated with Amino-Nogo, GST-Nogo-66 or no protein (substrate-bound) or with 100 nM Nogo protein (soluble) (scale bar, 40 µm). (d) is a photograph of a gel and an immunoblot where purified Amino-Nogo-Myc-His protein was subjected to SDS-PAGE and stained with Commassie Brilliant Blue (CBB) or immunoblotted with anti-Myc antibodies (Myc) (molecular weight markers of 200, 116, 97, 65 & 45 kDa are at left). (e) is a graph displaying experimental data where the percentage of 3T3 fibroblasts with an area greater than 1200 µm$^2$ (spread) was measured from experiments as in (b) on Nogo-coated surfaces (black) or with soluble 100 nM Nogo preparations (blue) (AM, Amino-Nogo; AM+Myc, Amino-Nogo preincubated with anti-Myc antibody; AM+Myc+Mo, AM+Myc preincubated with anti-mouse IgG antibody; Myc+Mo, anti-Myc antibody plus anti-murine IgG antibody). (f) is a graph displaying experimental data where the percentage of spread COS-7 cells was determined after culture on Nogo-coated surfaces or with soluble 100 nM Nogo preparations. (g) is a graph displaying experimental data where the effects of purified preparations of GST-Nogo-66 or Amino-Nogo on growth cone morphology was assessed in E12 dorsal root ganglion cultures at the indicated concentrations after thirty minutes. This demonstrates that GST-Nogo-66 is two orders of magnitude more potent than Amino-Nogo in this assay. (h) is a graph displaying experimental data where the neurite outgrowth per cell in E13 dorsal root ganglion cultures was quantitated from experiments as in (c) on Nogo-coated surfaces or with soluble 100 nM Nogo preparations. (i) is a graph displaying experimental data where the effects of Nogo preparations on neurite outgrowth in cerebellar granule neurons was measured.
Figure 1G:
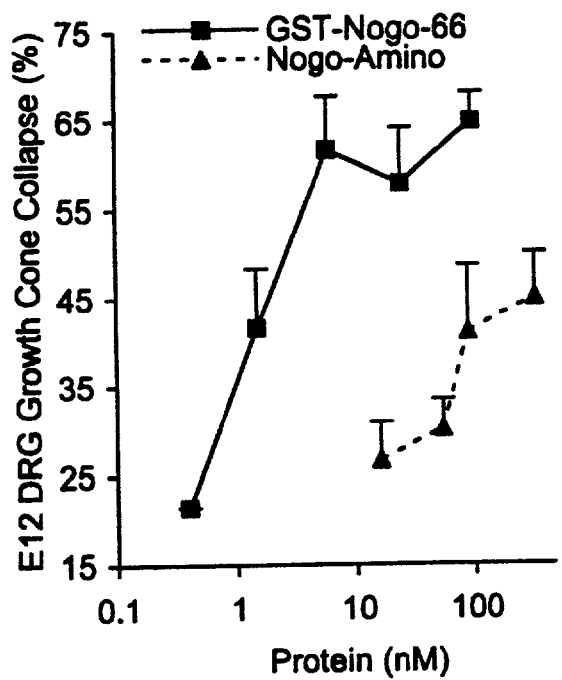
Figure 1B:
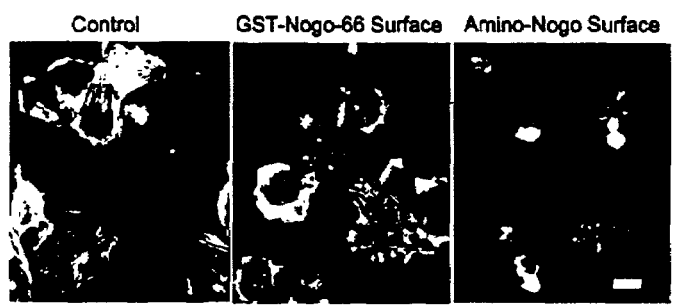

Assays of Nogo-A function have included growth cone collapse, neurite outgrowth, and fibroblast spreading with substrate-bound and soluble protein preparations (Caroni & Schwab, (1988) J. Cell Biol. 106, 1281–1288; GrandPré et al., (2000) Nature 403, 439–444; Chen et al., (2000) Nature 403, 434–439; Prinjha et al., (2000) Nature 403, 483–484). In assays of 3T3 fibroblast morphology, substrate-bound Nogo-66 does not inhibit spreading (FIG. 1b,e). Since NI250 preparations and full length Nogo-A are non-permissive for 3T3 spreading, it was necessary to consider whether different domains of Nogo might subserve this in vitro activity. To facilitate a comparison of different Nogo-A domains, the acidic amino terminal 1040 amino acid fragment (Amino-Nogo) was expressed as a Myc-his tagged protein in HBEK293T cells (FIG. 1d). The Nogo protein is present in cytosolic fractions. Surfaces coated with purified Amino-Nogo protein fail to support 3T3 fibroblast spreading (FIG. 1b,e). Similar results were observed for a kidney-derived cell line, COS-7 (FIG. 1f). Therefore, the amino terminal domain appears to account for the effects of full-length Nogo-A on fibroblasts. The Nogo-66 domain is specific for neurons; it does not affect non-neuronal cells.

Figure 1C:
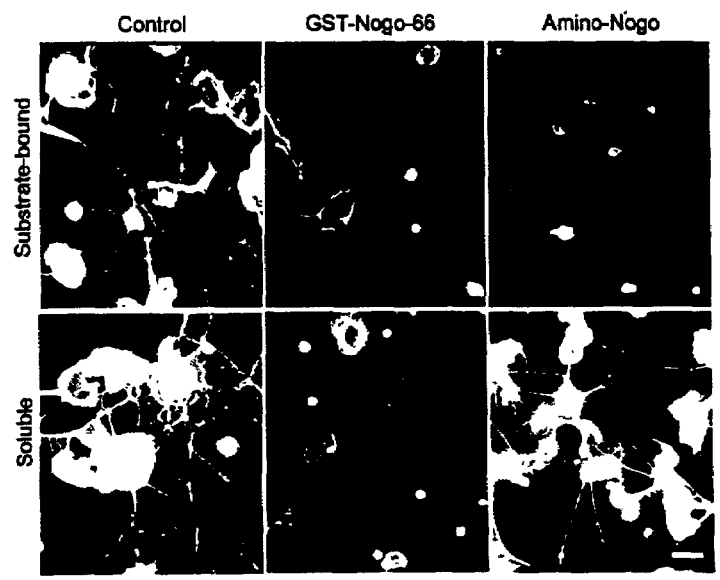
Figure 1D:
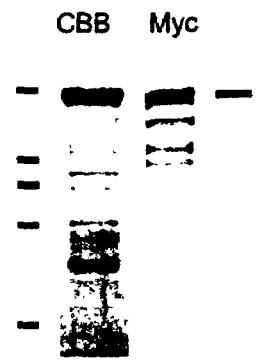

Dorsal root ganglion cultures were also exposed to Amino-Nogo protein (FIG. 1c,g–i). As for 3T3 fibroblasts, the fibroblast-like cells in the dorsal root ganglion culture do not spread on this substrate. Furthermore, axonal outgrowth is reduced to low levels on Amino-Nogo coated surfaces. Thus, while the Nogo-66 effects are neural-specific, the inhibitory action of the Amino-Nogo domain is more generalized. When presented in soluble form at 100 nM, the Nogo-66 polypeptide collapses chick E12 dorsal root ganglion growth cones and nearly abolishes axonal extension, as described previously (GrandPré et al., (2000) Nature 403, 439–444). In marked contrast, the soluble Amino-Nogo protein appears inactive, and does not significantly modulate dorsal root ganglion growth cone morphology or dorsal root ganglion axonal extension or non-neuronal cell spreading (FIG. 1c,g–i).

Figure 1E:
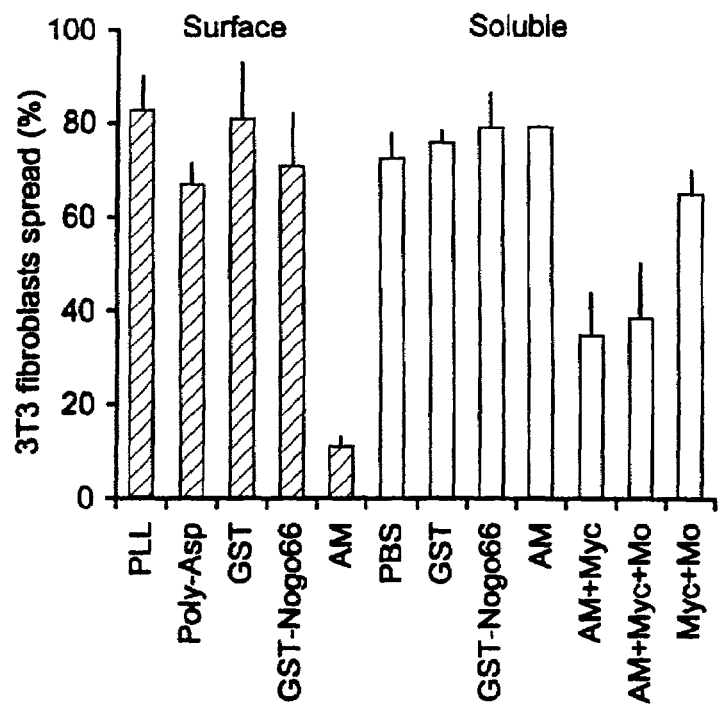
Figure 1F:
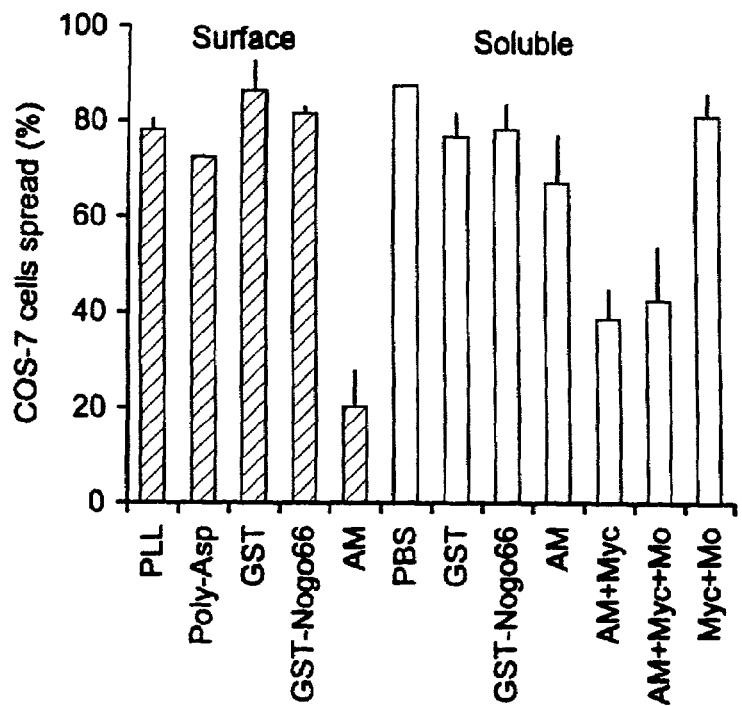
Figure 1H:
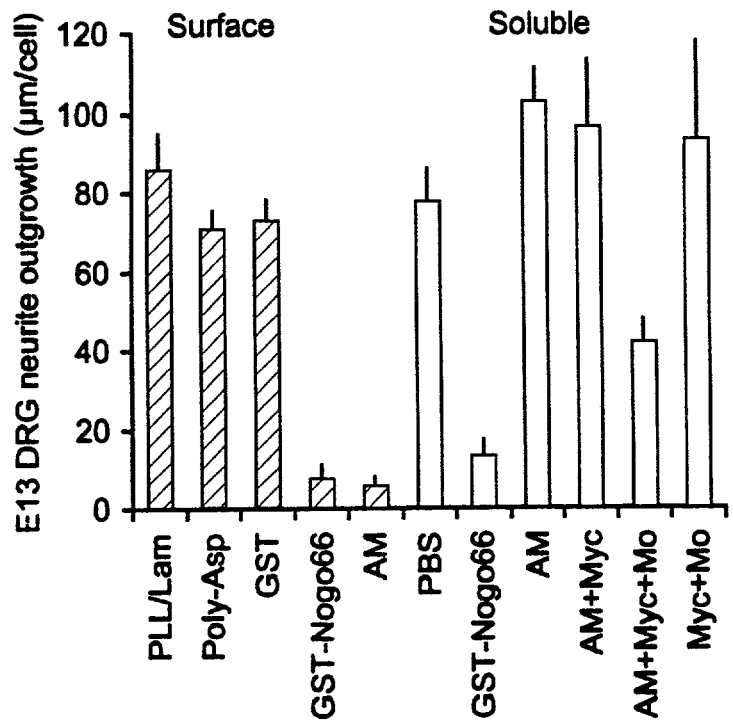
Figure 1I:
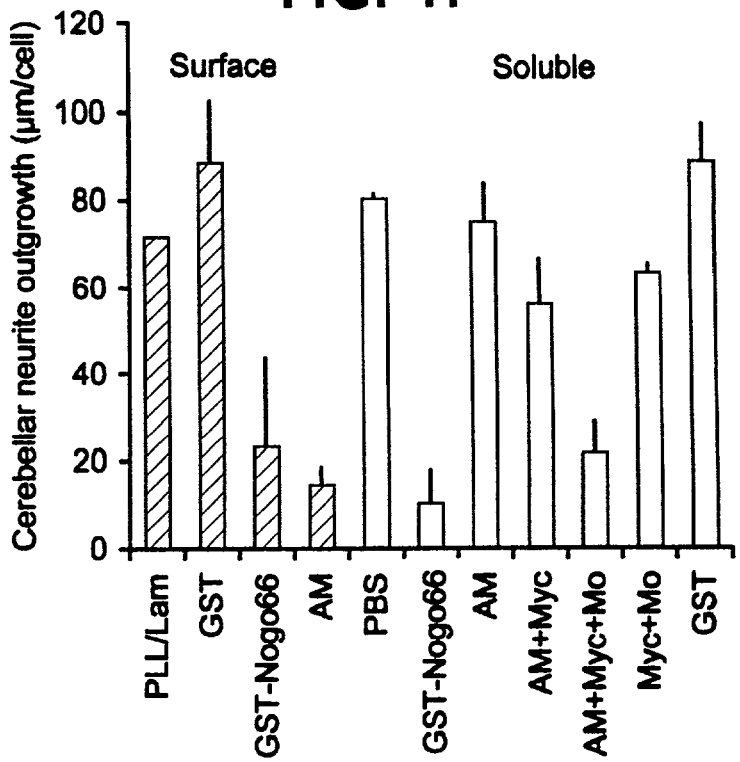

In the experiments of Walsh and colleague (Prinjha et al., (2000) Nature 403, 483–484), cerebellar granule neurons were studied and soluble Amino-Nogo was presented as an Fc fusion protein, presumably in dimeric form. Therefore, it was necessary to consider whether these differences might explain the inactivity of soluble Amino-Nogo. Mouse P4 cerebellar granule neurons respond to Nogo preparations is a fashion indistinguishable from chick E13 dorsal root ganglion neurons (FIG. 1i). Amino-Nogo dimerized with anti-Myc antibody inhibits 3T3 and COS-7 spreading (FIG. 1e,f) and tends to reduce cerebellar axon outgrowth (FIG.

1*i*). When further aggregated by the addition of anti-Mouse IgG antibody, Amino-Nogo significantly reduces both dorsal root ganglion and cerebellar axon outgrowth (FIG. 1*h,i*). While the Amino-Nogo protein is quite acidic, electrostatic charge alone does not account for its inhibitory effects since poly-Asp does not alter cell spreading or axonal outgrowth (FIG. 1*e,f,h*). Thus, the Nogo-66 domain is a potent and neuron-specific inhibitor, while the intracellular Amino-Nogo domain inhibits multiple cell types and appears to function only in an aggregated state.

Example 10

Localization of NgR

To further characterize the expression of the Nogo-66 receptor protein an antiserum to a GST-NgR fusion protein was developed. This antiserum detects an 85 kDa protein selectively in Nogo-66 receptor-expressing HEK293T cells (FIG. 9*a*), and specifically stains COS-7 cells expressing Nogo-66 receptor (FIG. 9*b*). Immunohistologic staining of chick embryonic spinal cord cultures localizes the protein to axons, consistent with mediation of Nogo-66-induced axon outgrowth inhibition. Nogo-66 receptor expression is not found in the O4-positive oligodendrocytes that express Nogo-66. Immunoreactive 85 kDa protein is expressed in Nogo-66-responsive neuronal preparations from chick E13 dorsal root ganglion, but to a much lesser degree in weakly responsive tissue from chick E7 dorsal root ganglion and chick E7 retina (FIG. 9*a*). Overall, the pattern of Nogo-66 expression is consistent with the protein mediating Nogo-66 axon inhibition.

This antibody is also effective in localizing the Nogo-66 receptor protein in tissue sections (FIG. 9*c*). While it is clear from in situ hybridization studies that the protein is expressed in multiple classes of neurons, immunohistology reveals the protein at high levels in CNS white matter in profiles consistent with axons. Protein is detectable at lower levels in neuronal soma and neuropil. This provides further support for the proposed function of this protein in mediating interactions with oligodendrocytes.

Example 11

NgR Mediates Nogo-66 Responses

Figure 10A:
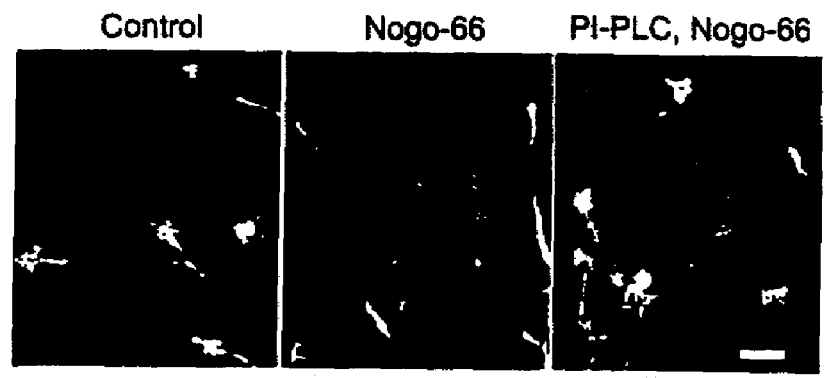
Figure 10D:
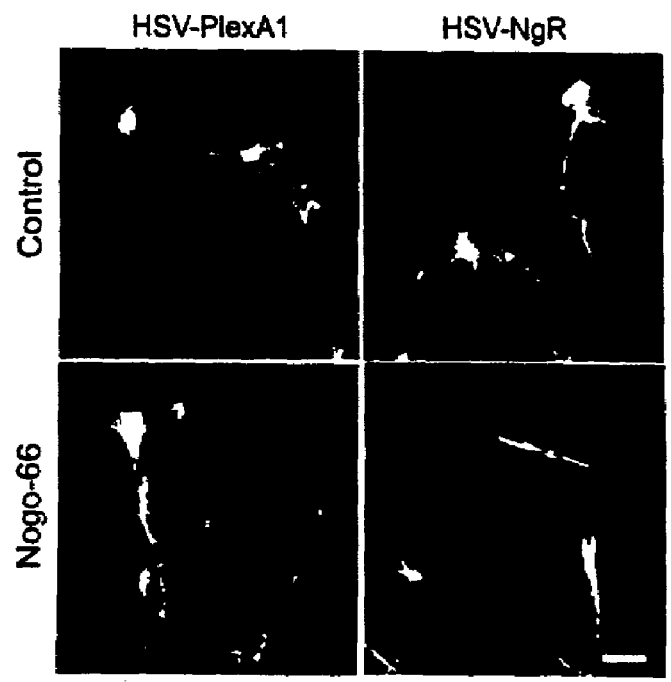
Figure 10E:
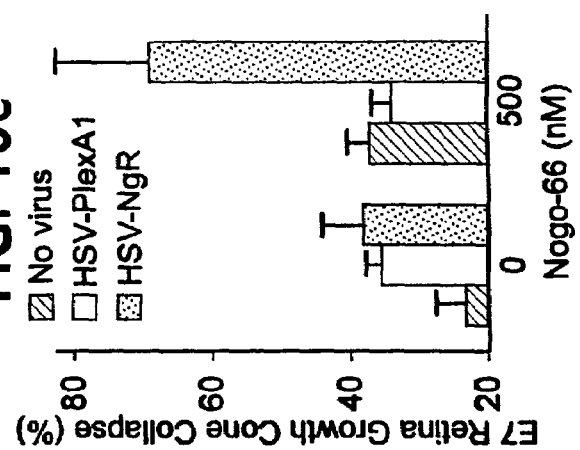
Figure 10C:
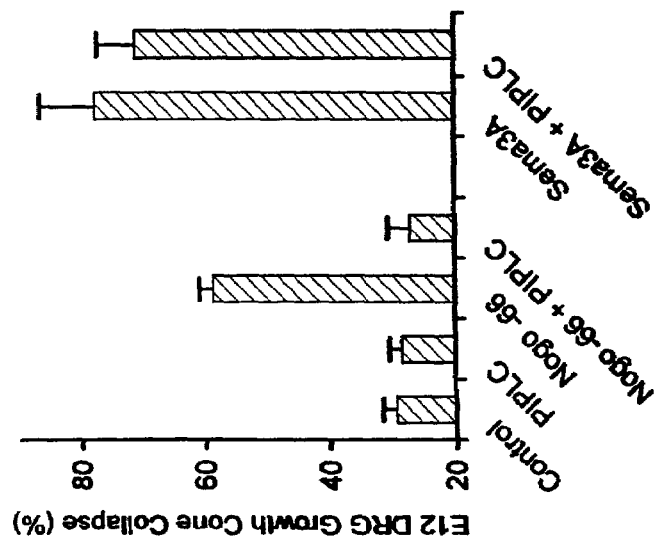
Figure 10B:
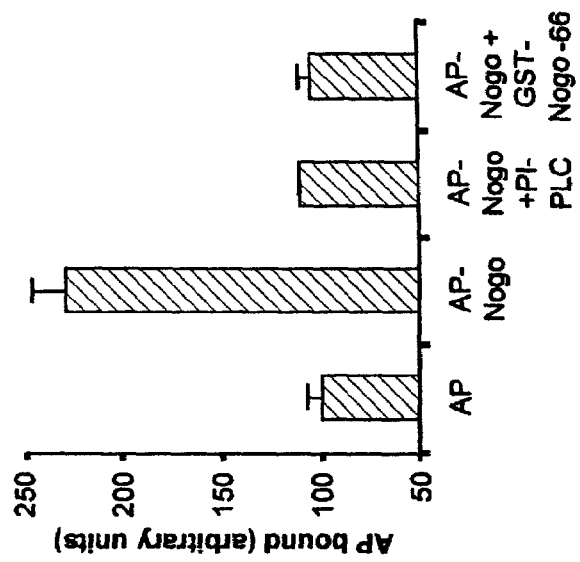

The Nogo-66 receptor protein is necessary for Nogo-66 action and not simply a binding site with a function unrelated to inhibition of axonal outgrowth. A first prediction is that phosphoinositol specific-Phospholipase C (PI-PLC) treatment to remove glycophosphatidylinositol (GPI)-linked proteins from the neuronal surface will render neurons insensitive to Nogo-66. This prediction holds true for chick E13 dorsal root ganglion neurons; PI-PLC treatment abolishes both AP-Nogo binding and GST-Nogo-66-induced growth cone collapse (FIG. 10*a–c*). As a control, Sema3A responses in the parallel cultures are not altered by PI-PLC treatment. Of course, PI-PLC treatment is expected to remove a number of proteins from the axonal surface so this result leaves open the possibility that other GPI-linked proteins are mediating the Nogo-66 response in untreated cultures.

To demonstrate that the Nogo-66 receptor is capable of mediating Nogo-66 inhibition of axon outgrowth, the protein was expressed in neurons lacking a Nogo-66 response. Both dorsal root ganglion and retinal neurons from E7 chick embryos were examined. The Nogo responses in the dorsal root ganglion neurons from this developmental stage are weak but slight responses can be detected in some cultures (data not shown). E7 retinal ganglion cell growth cones are uniformly insensitive to Nogo-66-induced growth cone collapse (FIG. 10*e*), do not bind AP-Nogo (data not shown) and do not exhibit 85 kDa anti-Nogo-66 receptor immunoreactive protein (FIG. 9*a*). Expression of NgR in these neurons by infection with recombinant HSV preparations renders the retinal ganglion cell axonal growth cones sensitive to Nogo-66-induced collapse. Infection with a control PlexinA1-expressing control HSV preparation does not alter Nogo responses. Taken together, these data indicate that the NgR identified here participates in Nogo-66 inhibition of axon regeneration.

Example 12

Structural Analysis of Nogo-66 Receptor

The Nogo-66 receptor structure was examined to determine which regions mediate Nogo-66 binding. The protein is simply divided into the leucine rich repeat and the non-leucine rich repeat region. Deletion analysis clearly shows that the leucine rich repeats are required for Nogo-66 binding but the remainder of the protein is not necessary (FIG. 11). Within the leucine rich repeat domain, two domains have been separately deleted. This is predicted to maintain the overall leucine rich repeat domain structure, and a similar approach has been utilized for the leutropin receptor. It is apparent that the Nogo-66 binding requires all eight leucine rich repeats, and suggests that a significant segment of the planar surface created by the linear beta sheets of the leucine rich repeats. The leucine rich repeat-amino terminous and leucine rich repeat-carboxy terminous conserved cysteine rich regions at each end of the leucine rich repeats are also required for Nogo-66 binding, presumably these are necessary to generate appropriate leucine rich repeat conformation.

Example 13

Blockade of Nogo by Soluble NgR Ectodomain Protein

One method for blocking a signal transduction cascade initiated by Nogo-66 binding to the NgR is to provide excess soluble ectodomain of the receptor. A secreted fragment of the NgR protein has been produced in HEK293T cells. The cDNA encoding amino acid residues 1–348 of the murine NgR were ligated into a eukaryotic expression vector and that DNA was transfected into HEK293T cells. Conditioned medium from these cells contains high levels of this NgR fragment (NgR-ecto), as demonstrated by immunoblots with an anti-NgR antibody. The conditioned medium contains approximately 1 mg of NgR-ecto protein per liter. In the AP-Nogo binding assay to COS-7 cells expressing full length NgR or to dorsal root ganglion neurons, the addition of NgR-ecto conditioned medium reduces the binding of 0.5 nM AP-Nogo-66 by 80%. Complex formation between soluble NgR-ecto and Nogo-66 prevents binding to cell surface receptors.

For some receptor systems, such soluble receptor ligand complexes can block signaling by creating an ineffective interaction. For example, the soluble ectodomain of Trk serves to block neurotrophin signaling and has been extensively used for this purpose (Shelton et al., (1995) J. Neurosci. 15, 477–491). Alternatively, the Nogo-66/NgRecto soluble complex may bind to and stimulate the presumed second transmembrane NgR subunit. There is precedence for this type of effect from studies of GDNF family receptors (Cacalano et al., (1998) Neuron 21, 53–62). The Nogo-66/NgR-ecto complex does not cause growth cone collapse in those neurons (chick E7 retinal ganglion cells) which lack the Nogo-66 receptor but containing other components of the Nogo signaling pathway. This indicates that NgR-ecto functions as a blocker of Nogo-66 signaling.

In direct tests, the NgR-ecto protein protects axons from the inhibitory effects of Nogo-66. NgR-ecto prevents Nogo-66-induced growth cone collapse and blocks Nogo-66-induced inhibition of neurite outgrowth from chick E13 DRG neurons (FIG. 12). Furthermore, the presence of NgR-ecto protein blocks the ability of CNS myelin to inhibit axonal outgrowth in vitro (FIG. 12). These data demonstrate that a NgR-ecto protein can promote axonal regeneration in vivo.

Example 14

Regions in the Luminal/Extracellular Domain of Nogo Necessary for NgR Binding

Portions of the luminal/extracellular domain of Nogo were tested to determine the amino acid sequences responsible for conveying inhibitory activity. To accomplish this, five 25 residue peptides, consisting of overlapping segments of the luminal/extracellular sequence fused to AP were constructed for testing in binding, growth cone collapse and neurite outgrowth assays.

Figure 5C:
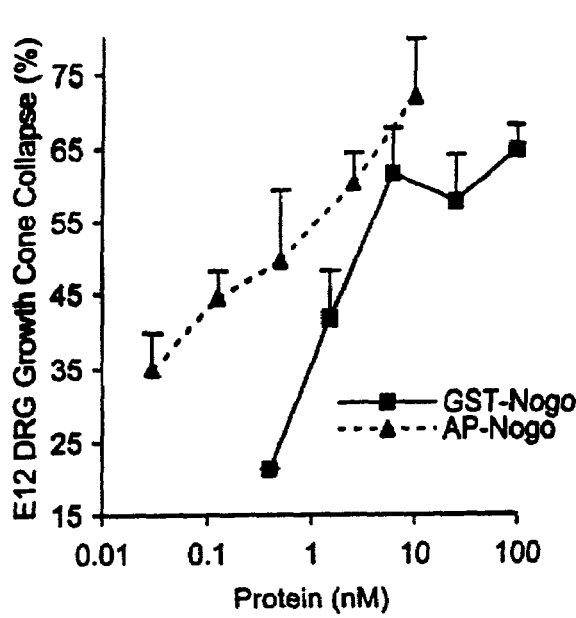
Figure 5D:
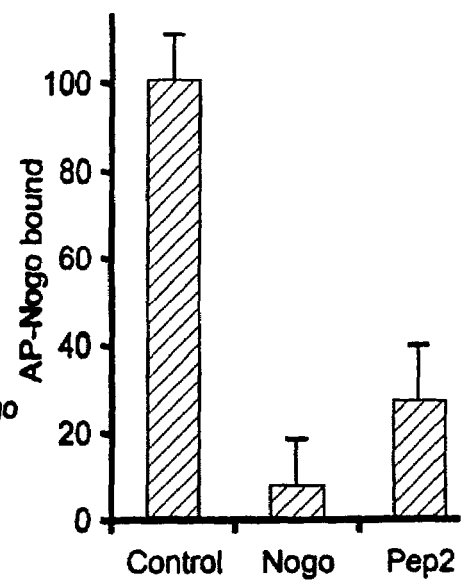
Figure 5E:
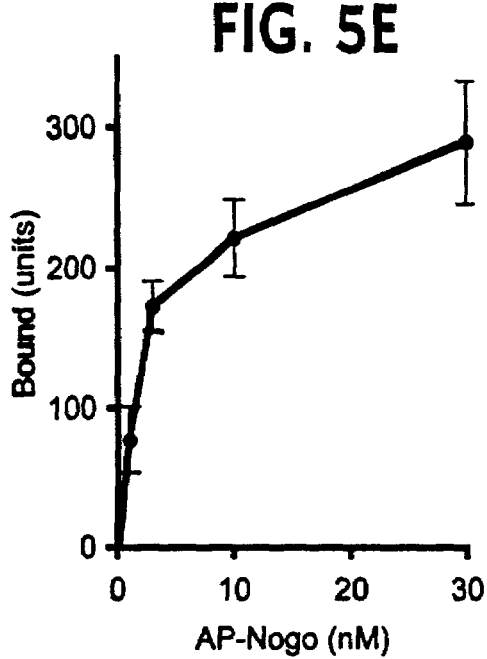
Figure 5F:
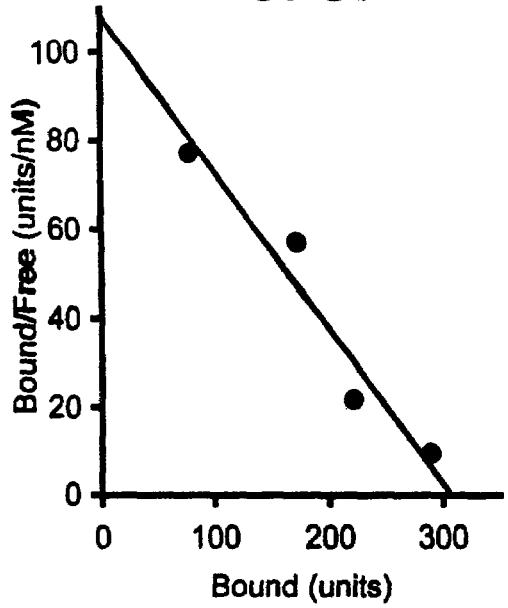

To generate AP-fusion proteins, PCR from cDNA of human Nogo-A was used to obtain inserts encoding residues #1055–1094, 1055–1089, 1055–1084, 1055–1079, 1060–1094, 1065–1094 or 1070–1094 of hNogoA (designated 1–40, 1–35, 1–30, 1–25, 6–40, 11–40, 16–40 in FIG. 5a). See FIG. 13a for the amino acid sequence of each. The inserts were excised and subcloned into the mammalian expression vector pcAP-6. Approximately 60 hours after constructs were transfected into 293T cells, conditioned medium was collected. The concentration of soluble AP-fused proteins within the conditioned medium or the presence of AP-fusion proteins within the conditioned medium from these cells was verified by measuring AP activity with the substrate p-nitro-phenyl phosphate, pNPP, or by western, respectively.

To determine if AP-fused deletion mutants of Nogo-66 bind mouse NgR ("mNgR"), COS-7 cells were transfected with a plasmid encoding the mouse NgR sequence ligated into pcDNA3.1. 48 hours after transfection, cells were washed with HBH (Hanks balanced salt solution containing 20 mM sodium Hepes, pH 7.05, and 1 mg ml$^{-1}$ bovine serum albumin) and then incubated with condition medium containing one of the AP-fusion proteins described above for 2 hours at 37° C. Cells were then washed, fixed, and left in HBH at 67° C. for 14–16 h to inactivate endogenous AP. AP-fusion protein binding to NgR expressing COS-7 cells was detected with the substrates NBT and BCIP (FIG. 13b).

Using this assay, AP fused Nogo-66 has been shown to bind COS7 cells expressing NgR with a $K_d$ of approximately 7 nM. Equally high affinity binding to NgR expressing cells, but not to non-transfected cells, was obtained with an AP-fusion protein consisting of residues 1–40 of the Nogo-66 sequence (designated 140-AP in FIG. 14a).

FIG. 14b graphically depicts the binding of 140-AP to COS-7 cells expressing mNgR as measured as a function of 140-AP concentration. A plot of the bound/free versus free 140-AP indicates that the Kd of 140-AP binding to mNgR in this assay is 8 nM. See FIG. 14c.

AP-fusion proteins 1–35 and 6–40 also demonstrated binding to mNgR transfected cells (FIG. 13b). Application of AP to these cells does not result in any detectable binding indicating that binding is the result of the Nogo-66 derived residues that were tested. Subsequent experiments (data not shown) have demonstrated that peptides having residues 1–35 and 1–34 bind strongly and almost equivalently to mNgR, whereas peptides having residues 1–33 bound mNgR approximately 50% less compared to the strong binders. Peptides having residues 1–31 and 1–30 exhibited almost no binding to NgR. Further, peptides having residues 2–40 of the hNogoA(#1055–1120) bound mNgR well whereas peptides having residues 10–40 had no binding and peptides having 6–40 had intermediate binding. Taken together, the data indicates that there are two regions of the hNogoA(#1055–1120) sequence that contain residues necessary for binding:residues 2–10 and 31–34, i.e., sequences IYKGVIQAI and EELV.

Example 15

Activity of Fragments of the Luminal/Extracellular Domain of Nogo

Tests were conducted to determine if the NgR binding observed with various fragments of the luminal/extracellular domain of Nogo was correlated with inhibitory activity. E12 chick DRG growth cone collapse and neurite outgrowth assays that have been described previously were used to determine the inhibitory activity of the fragments.

Briefly, for growth cone collapse, DRG explants were plated on plastic chamber slides precoated with 100 μg ml$^{-1}$ poly-$_L$-lysine and 10 μg ml$^{-1}$ laminin. Cultures were grown 14–16 h prior to treatment.

For neurite outgrowth assays, plastic chamber slides were coated with 100 μg ml$^{-1}$ poly-$_L$-lysine, washed, and dried. 3 μl drops of PBS containing GST-Nogo-66 were spotted and dried. Slides were then rinsed and coated with 10 μg ml fs24$^{-1}$ laminin before addition of dissociated E12 chick DRGs. AP-fusion proteins were added at the time of cell plating. Cultures were grown for 5–7 h after which neurite outgrowth was assessed.

Out of the AP fusion proteins that bind NgR, only the AP fusion proteins containing residues #1085–1109 of hNogoA were active in these assays (data not shown) thus indicating that residues within this region are critical to the inhibitory activity of the luminal/extracellular domain of Nogo. However, the activity of the AP fusion protein containing residues #1085–1109 of hNogoA was considerably less than the larger #1055–1120 fragment. These findings indicate that regions outside of residues #1085–1109, but within residues #1055–1120 of hNogoA may be crucial for high affinity binding of the residues #1055–1120 of hNogoA to NgR.

To determine the activity of AP-fusion proteins of Example 14, conditioned medium containing AP-fusion proteins were added to cultures at a final concentration of 20 nM. FIGS. 15a and b show that AP fused to residues #1055–1120 of NogoA is a potent growth-cone-collapsing agent (designated AP-Ng-66 in FIG. 15a and 1–66 in FIG. 15b). Other AP-fusion proteins containing residues #1055–1094, 1055–1089 or 1060–1094 (designated as 1–40, 1–35 or 6–40, respectively in FIG. 15b) did not induce growth cone collapse in this assay.

Although these fusion proteins bind to COS7 cells expressing NgR with high affinity, they fail to induce significant growth cone collapse in E12 chick DRG explant cultures. These peptides exhibit a desireable characteristic for blockers of Nogo activity—i.e., they themselves do not have inhibitory activity. The fusion of AP with residues #1055–1094 of hNogoA is a good example of a fusion protein that binds with high affinity to COS7 cells expressing NgR, but fails to mediate growth cone collapse. Taken together, these data suggest that high affinity binding to NgR can be dissociated from activation of an inhibitory signal through NgR.

Example 16

Synthetic Peptide 140 is an Antagonist Against Nogo-66 Activity (a) Growth Cone Collapse For further testing, a synthetic peptide containing amino acid residues #1055–1094 of hNgR, acetylated at the carboxy terminus and amidated at the amino terminus was used [hereinafter "Peptide 140"]. As was shown with the AP-fused version of this peptide, application of Peptide 140 does not induce significant growth cone collapse in E12 chick DRG explant cultures. Antagonist of Nogo-66 inhibitory activity may act by competing for, and thereby blocking NgR binding sites. To determine the antagonistic activity of Peptide 140, the above synthetic form of the peptide was added to E12 chick DRG explant cultures approximately 10 min before application of various concentrations of GST-NogoA (residues #1055–1120), TPA or Sema3A. 30 min later, cultures were fixed and growth cone collapse was assessed following staining with rhodamine-phalloidin. See FIG. 16a.

In this assay, Peptide 140 significantly blocks growth cone collapse induced by residues #1055–1120 fused to GST. Importantly, when Peptide 140 is applied to these cultures in conjunction with other growth cone collapsing agents, TPA or Sema3A, there is no significant reduction in collapse. These findings indicate that the antagonistic activity of Peptide 140 is selective for Nogo inhibitory activity. See FIG. 16b–d.

(b) Neurite Outgrowth Activity

Peptide 140 was tested for its ability to neutralize neurite outgrowth inhibition caused by the addition of GST fused to residues #1055–1120 of hNogoA (designated Nogo-66 in FIG. 16e). Plastic chamber slides were coated with 100 μg ml$^{-1}$ poly-$_L$-lysine, washed, and dried. 3 μl drops of PBS containing GST-hNogoA(residues #1055–1120) were spotted and dried. Slides were then rinsed and coated with 10 μg ml fs24$^{-1}$ laminin before addition of dissociated E12 chick DRGs. Peptide 140 was added at the time of cell plating. Cultures were grown for 5–7 h after which neurite outgrowth was assessed.

While GST-hNogoA(residues #1055–1120) dramatically reduces growth in these cultures, application of Peptide 140 alone has no observable effect on neurite outgrowth from these cells. See FIG. 16e. However, when cells are grown in the presence of both Peptide 140 and GST-hNogoA(residues #1055–1120), extensive outgrowth is observed. Importantly, challenging GST-hNogoA(residues #1055–1120)-induced activity with a scrambled version of Peptide 140 [acetyl-SYVKEYAPIFAGKSR-GEIKYQSEIHEAQVRSDELVQSLN-amide] does not result in blockade of outgrowth inhibition. Taken together, these studies suggest that Peptide 140 can be used as a functional antagonist of inhibitory activity of the luminal/extracellular domain of Nogo. See FIG. 16e.

Example 17

Peptide 140 can Neutralize the Inhibitory Activity of CNS Myelin at Low Concentrations, but not High Concentrations of CNS Myelin Inhibitory molecules associated with CNS myelin include MAG, chondroitin sulfate proteoglycans, and Nogo. Currently, the relative contribution of each of these molecules to the non-permissiveness of CNS myelin is largely unknown. To this end, standard in vitro assays were used to determine whether Peptide 140 can neutralize the inhibitory activity of CNS myelin (FIG. 17).

To determine the antagonistic activity of Peptide 140 against CNS myelin, the above synthetic peptide was added approximately 10 min before application of CNS myelin. 30 min later, cultures were fixed and growth cone collapse was assessed following staining with rhodamine-phalloidin. For neurite outgrowth assays, plastic chamber slide were coated with 100 μg ml$^{-1}$ poly-$_L$-lysine, washed, and dried. 3 μl drops of PBS containing CNS myelin were spotted and dried. Slides were then rinsed and coated with 10 μg ml fs24$^{-1}$ laminin before addition of dissociated E12 chick DRGs. Peptide 140, or the scrambled version of Peptide 140, was added at the time of cell plating. Cultures were grown for 5–7 h after which neurite outgrowth was assessed.

When applied to E12 chick DRG explant cultures, purified CNS myelin potently mediates growth cone collapse. The addition of both Peptide 140 and CNS myelin to these cultures reveals that at higher concentrations of myelin, the peptide had no effect on inhibitory activity. This result was not necessarily unexpected given that CNS myelin is known to contain inhibitory molecules other than Nogo. However, at the lowest myelin concentrations tested, Peptide 140 reduces myelin induced growth cone collapse to control levels. These data suggest that Nogo may be the only active inhibitor at low concentrations of myelin (and may therefore be the most potent inhibitor present in CNS myelin).

In addition to mediating growth cone collapse, CNS myelin dramatically reduces neurite outgrowth when applied to dissociated E12 chick DRG cultures. Addition of Peptide 140 to these cultures results in a partial neutralization of this inhibitory activity when CNS myelin is presented as a bound inhibitor (FIG. 17). For example, neurite outgrowth on a 20 ng spot of myelin increases from 35% to 65% (as compared with control outgrowth) following treatment with Peptide 140. Maximal activity of Peptide 140 is obtained at approximately 250 nM and is progressively lost with higher dilutions of the peptide. The scrambled version of Peptide 140 is ineffective at blocking CNS myelin induced neurite outgrowth inhibition. Taken together, these data suggest that Nogo is an important contributor to the inhibitory activity of CNS myelin. Further, much of the activity of Nogo-A may be attributable to the Nogo-66 inhibitory domain.

Peptide 140 significantly reduces myelin induced growth cone collapse and can partially restore neurite outgrowth in cultures grown on bound CNS myelin. Thus, Nogo can be a potent inhibitory molecule in CNS myelin.

There has been reports that neutralization of Nogo activity with the monoclonal antibody IN-1, raised against a myelin fraction enriched in Nogo-A, can partially block the inhibitory activity of CNS myelin both in vitro and in vivo. However, interpretation of the results of these studies is complicated by the presence of two inhibitory domains in Nogo-A (at residues #1055–1120 and the N-terminus of hNogoA) and a lack of information regarding the epitope of Nogo-A recognized by the IN-1 antibody. Further, using IN-1 to probe a Western blot of proteins extracted from spinal cord reveals binding to Nogo-A but also to a number of other unidentified protein species indicating that the antibody is not highly selective for Nogo-A. In contrast, a peptides derived from the luminal/extracellular domain of Nogo according to this invention selectively block hNogoA activity.

Example 18

NgR LRR Domains are Required for Binding to Nogo

To define residues critical for binding to Nogo-66 [hereinafter, hNogo-A(1055–1120)], mouse NgR (hereinafter mNgR) deletion mutants were generated and tested for their ability to bind hNogo-A(1055–1120). The amino acid sequence of mNgR contains a signal sequence, an amino-terminal region (NT), eight leucine-rich repeat (LRR) domains (LRR 1-8), a LRR carboxy-terminal domain (RRCT), a unique carboxy terminal domain (CT), and a GPI anchor domain. A series of mNgR mutant proteins with specific regions deleted was created using PCR-based site-directed mutagenesis (FIG. 1A).

The mNgR (WTNgR) and mNgR deletion mutants were ligated into the vector pSecTag2Hygro (Invitrogen, Buringame, Calif.). The vector adds to each of the proteins a secretion signal, a C-terminal polyhistidine (6×His) tag, and a C-terminal epitope recognized by the anti-His (C-term) antibody. wtNgR encodes residues 1 to 473 of mNgR (Fournier et al., Nature 409:341–346, 2001).

The $NgR_ANT$ construct encodes residues 58 to 473 of mNgR. The $NgR_ANT$ construct was made by using the primers $_\Delta LRR$-NT5 (5'-tgggatccgaacaaaaactcatctca-gaagaggatctgtctagccagcgaatcttcctgcatggc-3') and NgR3X (5'-ttctcgaggtcagcagggcccaagcactgtcc-3') to amplify a sequence from the wtNgR-pSecTag2Hygro plasmid. The amplified sequence was ligated into the XhoI/BamHI of pSecTag2.

The NgLRR-construct encodes residues 306 to 473 of mNgR. The NgLRR construct was made by using the primers, MycNgR305 (5'-tgggatccgaacaaaaactcatctca-gaagaggatctgctagagggctgtgctgtggcttca-3') and NgR3X (above) to amplify a sequence from the from the wtNgR-pSecTag2Hygro plasmid. The amplified sequence was ligated into the XhoI/BamHI of pSecTag2.

The $NgR_ACT$ construct encodes residues 26 to 305 and 443 to 473 of mNgR, thereby including the LRR and GPI regions of mNgR. Primers MycNgR (tgggatccgaacaaaaact-catctcagaagaggatctgccatgccctggtgcttgtgtgtgct) and 2NgRt313 (ttgcggccgctgaagccacagcacagccctctag) were used to amplify a sequence from the wtNgR-pSecTag2Hygro plasmid. Primers TM/GPI5 (5'-ttgcggccgctgagggt-tcaggggctctgcctgct-3') and NgR3X (above) were used to amplify a sequence from the wtNgR-pSecTag2Hygro plasmid. The amplified sequences were ligated together at the NotI site and then ligated into the BamHI/XhoI sites of pSecTag2.

The mNgR LLR deletions and $NgR_ALRRCT$ deletion mutants were generated using ExSite™ PCR-based site-directed mutagenesis kit (Stratagene, La Jolla, Calif.). Generally, the primers described below were used to amplify a sequence from the wtNgR pSecTag2 plasmid. The ends of the amplified products were ligated together. The resulting constructs were transfected into COS-7 cells.

The $NgR_A1$–2 construct encodes residues 1 to 56 and residues 106 to 473 of mNgR. The primers used for making the $NgR_A1$–2 construct were DEL LRR (5'PO4) (5'-ggctgg-gatgccagtgggcacagc-3') and DEL LRR2 (5'-ctcctggagcaac-tagatcttagt-3'). The $NgR_A3$–4 construct encodes residues 1 to 105 and residues 155 to 473 of mNgR. The primers used for making the $NgR_A3$–4 constructs were DEL LRR3 (5'PO4) (5'-ggtcagaccagtgaaggcagcagc-3') and DEL LRR4 (5'-gctct-gcagtacctctacctacaa-3'). The $NgR_A5$–6 construct encodes residues 1 to 153 and residues 203 to473 of mNgR. The primers used for making the $NgR_A5$–6 construct were DEL LRR5 (5'PO4) (5'-tgctagtccacggaataggccggg-3') and DEL LRR6 (5' PO4) (5'-agtcttgaccgcctcctcttgcac-3'). The $NgR_A7$–8 construct encodes residues 1 to 202 and residues 251 to 473 of mNgR. The primers used to make the $NgR_A7$–8 construct were DEL LRR7 (5'PO4) (5'-gtgcaggc-cacggaaagcgtgctc-3') and DEL LRR8 (5'-tctctgcagtacctgc-gactcaat-3'). The $NgR_ALRRCT$ construct encodes residues 1 to 259 and residues 311 to 473 of mNgR. The primers used to make the $NgR_ALRRCT$ construct were 3DLRR CT (5'-gtggcttcaggacccttccgtcccatc-3') and 5 DLRRCT (5'PO4) (5'-gtcattgagtcgcaggtactgcagagacct-3'). Expression of the mNgR mutants in COS-7 cells was verified by SDS-PAGE and immunoblotting (data not shown).

A vector encoding AP-hNogo-A(1055–1120) was constructed as described in Fournier et al., supra). The vector encoding AP-NgR was made by ligating the mNgR coding sequence from residues 27–451 in frame with the signal sequence-6×His-placental alkaline phosphatase (AP) sequence of the vector known as pAP-6 (Nakamura et al., Neuron 2: 1093–1100, 1988).

AP-hNogo-A(1055–1120) was prepared by transfecting the expression plasmid into HEK293T cells and, after four days, collecting the conditioned medium and purifying the secreted AP-hNogo-A(155–1120) protein by Ni2+ affinity chromatography as described (Nakamura et al., supra).

To determine whether mNgR or mNgR deletion mutants bound to hNogo-A(1055–1120), wtNgR or mNgR deletion mutants were transfected into COS-7 cells. Forty-eight hours after the transfection, the transfected COS-7 cells were washed with hanks balanced salt solution containing 20 mM sodium HEPES, pH 7.05, and 1 mg/ml bovine serum albumin (BSA) [hereinafter "HBH"]. Cells were then incubated for 2 hours at 23° C. with a conditioned medium enriched with purified AP-hNogo-A(1055–1120) diluted in HBH. AP-fusion protein was detected as previously described for AP-Sema3A (Takahashi et al., Nature Neurosci. 1:487–493, 1998).

wtNgR and $NgR_ACT$ transfected COS-7 cells bound to AP-hNogo-A(1055–1120), but the other deletion mutants did not (FIG. 18B). The AP-hNogo-A(1055–1120) binding pattern indicates that multiple residues within the NgR LRR region are required for AP-Nogo binding. Because the $NgR_A1$–2, $NgR_A3$–4, $NgR_A5$–6, and $NgR_A7$–8 deletions remove entire LRR domains it is unlikely that the entire tertiary structure of mNgR is disrupted.

Example 19

The Effect of NgRCT on Mediating NgR-Dependent Inhibition

Because the mouse NgRCT domain was determined to be dispensable for hNogo-A(1055–1120) binding, the ability of $NgR_ACT$ to mediate Nogo-dependent inhibition was examined. HSVNgR constructs transfected into HEK293T cells mediated the expression of mNgR proteins of the predicted molecular weight, as determined by SDS-PAGE and anti-Myc and anti-NgR immunoblotting (FIG. 19A). Day E7 chick retinal ganglion cells (RGCs) were grown for 12 hr, then further incubated for 24 hr with HSVNgR preparations. Explants were fixed with 4% paraformaldehyde with 0.1 M $PO_4$ and 20% sucrose and stained with phalloidin or with anti-myc antibodies. HSVNgR protein expression was detected in axons of infected (RGC) cultures (FIG. 19B).

Growth cone collapse in response to GST-hNogo-A (1055–1120) was investigated in infected RGC cultures. Retinal explants infected with recombinant viral preparations of PlexinA1 (PlexA1), wild-type NgR (wtNgR), NgRL1 chimeric receptor in which the GPI domain has been replaced by the transmembrane region and cytoplasmic tail from the mouse adhesion protein L1(NgRL1), or NgR carboxy terminal deletion mutant (NgR$_\Delta$CT) for 12 hr. Following infection, the cells were treated for 30 min with 0, 50, 250, or 500 nM GST-hNogo-A(1055–1120) (Grand-Pre et al., Nature 403: 439–444, 2000), fixed with 4% paraformaldehyde with 0.1 M $PO_4$ and 20% sucrose, and stained with phalloidin. As shown in FIG. 20, cells infected with the control PlexA1 virus did not respond to GST-hNogo-A(1055–1120), whereas cells infected with wtNgR underwent growth cone collapse in response to GST-hNogo-A(1055–1120). Cells infected with NgR$\Delta$CT were insensitive to GST-hNogo-A(1055–1120). The CT region of NgR is therefore required for effective NgR inhibitory signaling.

Example 20

The Effect of the CT Domain Alone on NgR Inhibitory Signaling

As NgR is a GPI linked protein tethered to the plasma membrane, it is likely that a second protein exists in a NgR signaling complex that is responsible for transducing Nogo signals within the cell. One possibility is that the CT domain of NgR may bind to a transducing component and initiate an intracellular signaling cascade upon ligand binding. This possibility would be consistent with the signaling incompetence of NgR$_\Delta$CT. If so, it is also possible that the NgR CT region may be capable of constitutive inhibitory activity. To test this possibility, a GSTNgRCT fusion protein was produced by PCR amplifying the CT region of NgR (amino acids 310–450) and ligating the fragment into the BamHI/EcoRI site of pGEX2T. The fusion protein was expressed and tested in a neurite outgrowth assay. E13 chick dorsal root ganglion (DRG) cells were dissociated and plated in the presence or absence of 100 mM soluble GSTNgRCT and assayed for neurite outgrowth lengths. In this assay, GST-hNogo-A(1055–1120) has been shown to inhibit neurite outgrowth (Fournier et al., supra). Soluble GSTNgRCT did not alter neurite outgrowth lengths, nor did it attenuate or enhance the response of dissociated E13 DRGs to GST-hNogo-A(1055–1120) substrates (FIG. 21).

Example 21

The NgR GPI Domain is not Required for NgR Signaling

To test the possibility that the GPI anchor has a role in mediating inhibitory Nogo signaling, a chimeric NgR molecule was constructed and assessed for its ability to correctly localize within the cell. HSVL1NgR contains a HSVNgR fusion in which the NgR GPI domain is replaced with the transmembrane domain of L1. HEK293T cells were cultured in 6-mm dishes and transfected with HSVwtNgR or HSVL1NgR. After 48 hr, cells were rinsed with PBS and lysed on ice with 375 µl precooled buffer containing 50 mM Tris-HCl (pH 7.4), 150 mM NaCl, 5 mM EDTA, and 0.1% Triton X-100, (hereinafter "TNEX"), and 10 mM NaF and a protease inhibitor cocktail (Roche Diagnostics, Mannheim, Germany). Cells were homogenized by passing the ice-cold lysates through a 27 G needle 10 times. Extracts were adjusted to 35% OptiPrep (Gibco BRL) by adding 525 µl of 60% OptiPrep/0.1% Triton X-100, then placed in an ultracentrifuge tube and overlayed with 8.75 ml of 30% OptiPrep in TNEX and 1 ml of TNEX. After centrifugation (4 hr, 200,000×g, 4° C.), seven fractions were collected, precipitated with trichloroacetic acid, washed with acetone, air dried, and resuspended in Laemlli sample buffer. Fractions were analyzed by 8% SDS-PAGE and immunoblotting with the NgR antibody (Fournier et al., supra). Transferrin receptor (TfR) was detected with an anti-TfP monoclonal antibody; caveolin was detected with anti-caveolin rabbit polyclonal antibody.

As expected for a GPI-anchored protein, wtNgR localized mainly to caveolin-rich lipid raft fractions (FIG. 22). A much smaller proportion of the chimeric L1NgR was localized to the lipid raft fraction. Expression of the wild-type HSVNgR or HSVNgRL1 chimeric protein in HEK293T cells results in an altered distribution of HSVNgRL1.

Example 22 mNgR Binds mNgR

NgR was tested for the ability to self-associate. For this study, mNgR [hereinafter, wtNgR or WT] and mNgR deletion mutants (see FIG. 18A) were transfected into COS-7 cells. Forty-eight hours after the transfection, the transfected COS-7 cells were washed with HBH. Cells were then incubated for 2 hours at 23° C. with a conditioned medium containing AP-hNogo-A(1055–1120) fusion protein diluted in HBH. AP-fusion protein was detected as previously described for AP-Sema3A (Takahashi et al., Nature Neurosci. 1:487–493, 1998). Similar to the AP-Nogo binding profile, AP-NgR bound to wtNgR and NgR$_\Delta$CT (FIG. 23). Nogo treatment had little, if any, effect on the NgR-NgR interaction (data not shown). Other NgR deletion mutants did not bind AP-NgR. The same NgR domains are required for GST-hNogo-A(1055–1120) binding and NgR oligomerization Example 23

Soluble NgR Antagonizes Nogo and Myelin-Dependent Inhibition

Although the role of the GPI anchor may be to regulate NgR cellular compartmentalization, another possible role for the GPI linkage is to provide a NgR cleavage site. Cleaving NgR could serve to affect hNogo-A(1055–1120) signaling by rendering a neuron insensitive to hNogo-A (1055–1120) and by releasing soluble NgR that could then act on adjacent cells to modulate hNogo-A(1055–1120) signaling. To determine if soluble mNgR modulates hNogo-A(1055–1120)-dependent inhibition, a soluble mNgR was generated by inserting a truncated cDNA encoding mNgR residues 1–348 in frame with a myc-His carboxy tag into pcDNA3.1. The resulting plasmid expressing mNgREcto was transfected into HEK293T cells, and conditioned media containing mNgREcto protein was collected. To test the effect of mNgREcto on Nogo signaling, E13 dissociated DRGs were plated in the presence of bNogo-A(1055–1120) or myelin. The inhibitors were presented in either soluble or substrate-bound forms. For neurite outgrowth assays on hNogo-A(1055–1120) or myelin substrates, Permanox chamber slides were coated with 100 μ, fs24 g ml$^{-1}$ poly-L-Lysine, washed, and then 3-μl drops of phosphate-buffered saline (hereinafter "PBS") containing 0, 10, 50, or 150 ng of GST-hNogo-A(1055–1120) or myelin were spotted and dried. GST-hNogo-A(1055–1120) and myelin were prepared as previously described (GrandPre et al., supra; Fournier et al., J. Cell Biol. 149:411–421, 2000). After three PBS washes, slides were coated with 10 μg ml$^{-1}$ laminin. Laminin was then aspirated and dissociated E13 chick DRG neurons were added. After 6–8 hr of outgrowth, cultures were fixed and neurite outgrowth lengths were assessed. For blockade experiments with NgREcto, spots were incubated with HEK293T cell conditioned media or NgREcto-transfected-HEK293T cell conditioned media following for 1 hr following the laminin coating step and before the addition of dissociated neurons. As shown in FIG. 24, following blockage with NgREcto, neurite outgrowth inhibition by Nogo or myelin substrates was partially reversed. Thus, soluble fragments of NgR might serve physiologically or pharmacologically to reduce GST-hNogo-A(1055–1120) inhibition of axonal regeneration.

To test the signaling capability of NgRLI, recombinant HSVL1NGR preparations were produced and used to infect E7 RGCs. Infected RGCs were treated with GST-hNogo-A (1055–1120) and growth cone collapse was assessed (FIG. 20). At high concentrations of GST-hNogo-A(1055–1120), NgRL1 transduces Nogo signals as efficiently as wtNgR. However, at 50 nM GST-hNogo-A(1055–1120), wtNgR is capable of signaling whereas NgRL1 infected RGCs are not responsive to GST-hNogo-A(1055–1120). This indicates that NgRL1 is capable of mediating inhibitory signals in response to Nogo, however less efficiently than wtNgR. When transfected HBEK293T cells were treated with GST-hNogo-A(1055–1120), the membrane fractionation profile of wtNgR and L1Ngr remained the same (data not shown) suggesting that Nogo does not modulate NgR localization to lipid raft compartments in HEK293T cells. It is however possible that ligand binding to NgR modifies signaling within the compartment as is the case for ephrins (Davy et al., Genes Dev., 13:3125–3135, 1999) or recruits unknown signaling partners to a lipid raft complex. Because the intracellular signals induced by Nogo have not been elucidated, it remains to be determined if ligand binding effects signaling events at caveolar microdomains.

Throughout the specification, the word "comprise," or variations such as "comprises" or "comprising," will be understood to imply the inclusion of a stated integer or group of integers but not the exclusion of any other integer or group of integers.

Although the present invention has been described in detail with reference to examples above, it is understood that various modifications can be made without departing from the spirit of the invention. Therefore, it will be appreciated that the scope of this invention is encompassed by the embodiments of the inventions recited herein and the specification rather than the specific examples which are exemplified below. All cited patents and publications referred to in this application are herein incorporated by reference in their entirety. The results of part of the experiments disclosed herein have been published (GrandPré et al., (2000) Nature 403, 439–444) after the filing date of U.S. Provisional Application 60/175,707 from which this application claims priority, this publication herein incorporated by reference in its entirety.

What is claimed:

1. An isolated polypeptide comprising an amino acid sequence that is at least 80% identical to amino acids 27–309 of SEQ ID NO:2, wherein said polypeptide inhibits NOGO-receptor-mediated neurite outgrowth inhibition.

2. The polypeptide of claim 1, wherein said amino acid sequence is at least 90% identical to amino acids 27–309 of SEQ ID NO:2.

3. The polypeptide of claim 2, wherein said amino acid sequence is at least 95% identical to amino acids 27–309 of SEQ ID NO:2.

4. The polypeptide of claim 3, wherein said polypeptide comprises amino acids 27 to 309 of SEQ IID NO:2.

5. A composition comprising the polypeptide of claim 1 and a pharmaceutically acceptable carrier.

6. An isolated polypeptide consisting essentially of amino acids 27 to 309 of SEQ ID NO:2, except for it 20 conservative amino acid substitutions, wherein said polypeptide inhibits NOGO-receptor-mediated neurite outgrowth inhibition.

7. A composition comprising the polypeptide of claim 6 and a pharmaceutically acceptable carrier.

8. An isolated soluble polypeptide comprising an ectodomain fragment of SEQ ID NO:2, wherein said polypeptide inhibits NOGO-receptor-mediated neurite outgrowth inhibition.

9. The soluble polypeptide of claim 8, comprising amino acids 27 to 309 of SEQ ID NO:2.

10. The soluble polypeptide of claim 9, comprising amino acids 1 to 348 of SEQ ID NO:2.

11. A composition comprising the polypeptide of claim 8 and a pharmaceutically acceptable carrier.

12. An isolated polypeptide fragment consisting of at least 35 consecutive amino acids of amino acids 1 to 445 of SEQ ID NO:2, wherein said polypeptide fragment inhibits NOGO-receptor-mediated neurite outgrowth inhibition.

13. The polypeptide fragment of claim 12, consisting essentially of amino acids 27 to 445 of SEQ ID NO:2.

14. The polypeptide fragment of claim 13, consisting essentially of amino acids 27 to 309 of SEQ ID NO:2.

15. The polypeptide fragment of claim 12, consisting essentially of amino acids 1 to 348 of SEQ ID NO:2.

16. The polypeptide fragment of claim 15, consisting essentially of amino acids 1 to 309 of SEQ ID NO:2.

17. A composition comprising the polypeptide fragment of claim 12 and a pharmaceutically acceptable carrier.

18. An isolated polypeptide comprising amino acids 27 to 309 of SEQ ID NO:2, fused to a heterologous polypeptide; wherein said polypeptide inhibits NOGO-receptor-mediated neurite outgrowth inhibition.

19. The polypeptide of claim 18, wherein said heterologous polypeptide is Glutathione S-transferase (GST).

20. The polypeptide of claim 18, wherein said heterologous polypeptide is a Histidine tag (His tag).

21. The polypeptide of claim 18, wherein said heterologous polypeptide is alkaline phosphatase (AP).

22. A composition comprising the polypeptide of claim 18 and a pharmaceutically acceptable carrier.

23. An isolated polypeptide comprising (a) an amino acid sequence that is at least 80% identical to amino acids 27–309 of SEQ ID NO:2; and (b) a heterologous polypeptide fused thereto, wherein said polypeptide inhibits NOGO-receptor-mediated neurite outgrowth inhibition.

24. The polypeptide of claim 23, wherein said amino acid sequence of (a) is at least 90% identical to amino acids 27–309 of SEQ ID NO:2.

25. The polypeptide of claim 24, wherein said amino acid sequence of (a) is at least 95% identical to amino acids 27–309 of SEQ ID NO:2.

26. A composition comprising the polypeptide of claim 24 and a pharmaceutically acceptable carrier.

27. An isolated polypeptide consisting essentially of an amino acid sequence at least 80% identical to amino acids 1 to 348 of SEQ ID NO:2, wherein said polypeptide inhibits NOGO receptor-mediated neurite outgrowth inhibition.

28. The polypeptide of claim 27, wherein said amino acid sequence is at least 90% identical to amino acids 1 to 348 of SEQ ID NO:2.

29. The polypeptide of claim 28, wherein said amino acid sequence is at least 95% identical to amino acids 1 to 348 of SEQ ID NO:2.

30. The polypeptide of claim 29, wherein said amino acid sequence consists essentially of amino acids It 348 of SEQ ID NO:2.

31. A composition comprising the polypeptide of claim 28, and a pharmaceutically acceptable carrier.

32. An isolated polypeptide comprising amino acids 1 to 348 of SEQ ID NO:2, fused to a heterologous polypeptide; wherein said polypeptide inhibits NOGO-receptor-mediated neurite outgrowth inhibition.

33. The polypeptide of claim 32, wherein said wherein said heterologous polypeptide is Glutathione S-transferase (GST).

34. The polypeptide of claim 32, wherein said heterologous polypeptide is a Histidine tag (His tag).

35. The polypeptide of claim 32, wherein said heterologous polypeptide is alkaline phosphatase (AP).

36. A composition comprising the polypeptide of claim 32 and a pharmaceutically acceptable carrier.

37. An isolated polypeptide comprising: (a) an amino acid sequence that is at least 80% identical to amino acids 1 to 348 of SEQ ID NO:2; and (b) a heterologous polypeptide fused thereto, wherein said polypeptide inhibits NOGO-receptor-mediated neurite outgrowth inhibition.

38. The polypeptide of claim 37, wherein said amino acid sequence of (a) is at least 90% identical to amino acids I to 348 of SEQ ID NO:2.

39. The polypeptide of claim 38, wherein amino acid sequence of (a) is at least 95% identical to amino acids 1 to 348 of SEQ ID NO:2.

40. A composition comprising the polypeptide of claim 39 and a pharmaceutically acceptable carrier.

41. An isolated soluble ectodomain fragment of NgR comprising at least 35 consecutive amino acids of amino acids 1 to 348 of SEQ IID NO:2, wherein said ectodomain fragment inhibits NOGO-receptor-mediated neurite outgrowth inhibition.

42. The polypeptide of claim 41, wherein said amino acid sequence is at least 90% identical to amino acids 27–445 of SEQ ID NO:2.

43. The polypeptide of claim 42, wherein said amino acid sequence is at least 95% identical to amino acids 27–445 of SEQ ID NO:2.

44. The polypeptide of claim 43, wherein said polypeptide consists essentially of amino acids 27 to 445 of SEQ ID NO:2.

45. A composition comprising the polypeptide of claim 41 and a pharmaceutically acceptable carrier.

46. An isolated polypeptide consisting essentially of an amino acid sequence that is at least 80% identical to amino acids 27–445 of SEQ ID NO:2, wherein said polypeptide inhibits NOGO-receptor-mediated neurite outgrowth inhibition.

47. The polypeptide of claim 45, wherein said amino acid sequence is at least 90% identical to amino acids 1–309 of SEQ ED NO:2.

48. The polypeptide of claim 46, wherein said amino acid sequence is at least 95% identical to amino acids 1–309 of SEQ ID NQ:2.

49. The polypeptide of claim 46, wherein said polypeptide consists essentially of amino acids It 309 of SEQ IID NO:2.

50. A composition comprising the polypeptide of claim 41 and a pharmaceutically acceptable carrier.

\* \* \* \* \*

UNITED STATES PATENT AND TRADEMARK OFFICE
CERTIFICATE OF CORRECTION

PATENT NO.         : 7,119,165 B2
APPLICATION NO. : 09/972599
DATED                  : October 10, 2006
INVENTOR(S)        : Strittmatter It is certified that error appears in the above-identified patent and that said Letters Patent is hereby corrected as shown below:

In column 97, claim 4, please delete "wherein said polypeptide comprises amino acids 27 to 309 of SEQ 1ID NO:2." and insert therein -- wherein said polypeptide comprises amino acids 27 to 309 of SEQ ID NO:2. --.

In column 97, claim 6, please delete "except for it 20 conservative amino acid substitutions" and insert therein -- except for 1 to 20 conservative amino acid substitutions --.

In column 99, claim 26, please delete "A composition comprising the polypeptide of claim 24 and a pharmaceutically acceptable carrier." and insert therein -- A composition comprising the polypeptide of claim 23 and a pharmaceutically acceptable carrier. --.

In column 99, claim 30, please delete "wherein said amino acid sequence consists essentially of amino acids It 348 of SEQ ID NO:2." and insert therein -- wherein said amino acid sequence consists essentially of amino acids 1 to 348 of SEQ ID NO:2. --.

In column 99, claim 31, please delete "A composition comprising the polypeptide of claim 28" and insert therein -- A composition comprising the polypeptide of claim 27 --.

In column 99, claim 33, please delete "wherein said wherein said heterologous polypeptide is Glutathione S-transferase (GST)." and insert therein -- wherein said heterologous polypeptide is Glutathione S-transferase (GST). --.

In column 100, claim 40, please delete "A composition comprising the polypeptide of claim 39 and a pharmaceutically acceptable carrier" and insert therein -- A composition comprising the polypeptide of claim 37 and a pharmaceutically acceptable carrier --.

In column 100, claim 41, please delete "An isolated soluble ectodomain fragment of NgR comprising at least 35 consecutive amino acids of amino acids 1 to 348 of SEQ 1ID NO:2, wherein said ectodomain fragment inhibits NOGO-receptor-mediated neurite outgrowth inhibition." and insert therein -- An isolated polypeptide consisting essentially of an amino acid sequence that is at least 80% identical to amino acids 27-445 of SEQ ID NO:2, wherein said polypeptide inhibits NOGO-receptor-mediated neurite outgrowth inhibition. --.

UNITED STATES PATENT AND TRADEMARK OFFICE
CERTIFICATE OF CORRECTION

PATENT NO.       : 7,119,165 B2
APPLICATION NO.  : 09/972599
DATED            : October 10, 2006
INVENTOR(S)      : Strittmatter It is certified that error appears in the above-identified patent and that said Letters Patent is hereby corrected as shown below:

In column 100, claim 46, please delete "An isolated polypeptide consisting essentially of an amino acid sequence that is at least 80% identical to amino acids 27-445 of SEQ ID NO:2" and insert therein -- An isolated polypeptide consisting essentially of an amino acid sequence that is at least 80% identical to amino acids 1-309 of SEQ ID NO:2 --.

In column 100, claim 47, please delete "The polypeptide of claim 45" and insert therein -- The polypeptide of claim 46 --.

In column 100, claim 48, please delete "The polypeptide of claim 46" and insert therein -- The polypeptide of claim 47 --.

In column 100, claim 49, please delete "The polypeptide of claim 46" and insert therein -- The polypeptide of claim 47 --.

In column 100, claim 50, please delete "A composition comprising the polypeptide of claim 41 and a pharmaceutically acceptable carrier." and insert therein -- A composition comprising the polypeptide of claim 46 and a pharmaceutically acceptable carrier. --.

Signed and Sealed this

Ninth Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,119,165 B2
APPLICATION NO. : 09/972599
DATED : October 10, 2006
INVENTOR(S) : Strittmatter It is certified that error appears in the above-identified patent and that said Letters Patent is hereby corrected as shown below:

In column 97, claim 4, lines 53-54, please delete "wherein said polypeptide comprises amino acids 27 to 309 of SEQ 1ID NO:2." and insert therein -- wherein said polypeptide comprises amino acids 27 to 309 of SEQ ID NO:2. --.

In column 97, claim 6, lines 58-59, please delete "except for it 20 conservative amino acid substitutions" and insert therein -- except for 1 to 20 conservative amino acid substitutions --.

In column 99, claim 26, lines 18-19, please delete "A composition comprising the polypeptide of claim 24 and a pharmaceutically acceptable carrier." and insert therein -- A composition comprising the polypeptide of claim 23 and a pharmaceutically acceptable carrier. --.

In column 99, claim 30, lines 30-32, please delete "wherein said amino acid sequence consists essentially of amino acids It 348 of SEQ ID NO:2." and insert therein -- wherein said amino acid sequence consists essentially of amino acids 1 to 348 of SEQ ID NO:2. --.

In column 99, claim 31, lines 33-34, please delete "A composition comprising the polypeptide of claim 28" and insert therein -- A composition comprising the polypeptide of claim 27 --.

In column 99, claim 33, lines 39-41, please delete "wherein said wherein said heterologous polypeptide is Glutathione S-transferase (GST)." and insert therein -- wherein said heterologous polypeptide is Glutathione S-transferase (GST). --.

In column 100, claim 40, lines 12-13, please delete "A composition comprising the polypeptide of claim 39 and a pharmaceutically acceptable carrier" and insert therein -- A composition comprising the polypeptide of claim 37 and a pharmaceutically acceptable carrier --.

In column 100, claim 41, lines 14-18, please delete "An isolated soluble ectodomain fragment of NgR comprising at least 35 consecutive amino acids of amino acids 1 to 348 of SEQ 1ID NO:2, wherein said ectodomain fragment inhibits NOGO-receptor-mediated neurite outgrowth inhibition." and insert therein -- An isolated polypeptide consisting essentially of an amino acid sequence that is at least 80% identical to amino acids 27-445 of SEQ ID NO:2, wherein said polypeptide inhibits NOGO-receptor-mediated neurite outgrowth inhibition. --.

UNITED STATES PATENT AND TRADEMARK OFFICE
CERTIFICATE OF CORRECTION

PATENT NO. : 7,119,165 B2
APPLICATION NO. : 09/972599
DATED : October 10, 2006
INVENTOR(S) : Strittmatter It is certified that error appears in the above-identified patent and that said Letters Patent is hereby corrected as shown below:

In column 100, claim 46, lines 31-33, please delete "An isolated polypeptide consisting essentially of an amino acid sequence that is at least 80% identical to amino acids 27-445 of SEQ ID NO:2" and insert therein -- An isolated polypeptide consisting essentially of an amino acid sequence that is at least 80% identical to amino acids 1-309 of SEQ ID NO:2 --.

In column 100, claim 47, line 36, please delete "The polypeptide of claim 45" and insert therein -- The polypeptide of claim 46 --.

In column 100, claim 48, line 39, please delete "The polypeptide of claim 46" and insert therein -- The polypeptide of claim 47 --.

In column 100, claim 49, line 42, please delete "The polypeptide of claim 46" and insert therein -- The polypeptide of claim 47 --.

In column 100, claim 50, lines 44-45, please delete "A composition comprising the polypeptide of claim 41 and a pharmaceutically acceptable carrier." and insert therein -- A composition comprising the polypeptide of claim 46 and a pharmaceutically acceptable carrier. --.

This certificate supersedes the Certificate of Correction issued December 9, 2008.

Signed and Sealed this

Thirtieth Day of December, 2008

JON W. DUDAS
*Director of the United States Patent and Trademark Office*